United States Patent
Dominguez et al.

(10) Patent No.: US 10,907,197 B2
(45) Date of Patent: Feb. 2, 2021

(54) PROBES FOR IMAGING HUNTINGTIN PROTEIN

(71) Applicant: CHDI Foundation, Inc., New York, NY (US)

(72) Inventors: Celia Dominguez, Los Angeles, CA (US); John Wityak, Carlsbad, CA (US); Jonathan Bard, New York, NY (US); Christopher John Brown, Abingdon (GB); Michael Edward Prime, Swindon (GB); Derek Alexander Weddell, Didcot (GB); Daryl Simon Walter, Abingdon (GB); Paul Richard Giles, Abingdon (GB); Ian James Wigginton, Didcot (GB); Malcolm George Taylor, Newport-on-Tay (GB); Sébastien René Gabriel Galan, Abingdon (GB); Peter David Johnson, Abingdon (GB); Thomas Martin Krülle, Oxford (GB); Inaki Morao, Abingdon (GB); Daniel Clark-Frew, Wantage (GB)

(73) Assignee: CHDI Foundation, Inc., New York, NY (US)

( * ) Notice: Subject to any disclaimer, the term of this patent is extended or adjusted under 35 U.S.C. 154(b) by 0 days.

(21) Appl. No.: 15/507,217

(22) PCT Filed: Aug. 28, 2015

(86) PCT No.: PCT/US2015/047427
§ 371 (c)(1),
(2) Date: Feb. 27, 2017

(87) PCT Pub. No.: WO2016/033460
PCT Pub. Date: Mar. 3, 2016

(65) Prior Publication Data
US 2017/0292150 A1     Oct. 12, 2017

Related U.S. Application Data

(60) Provisional application No. 62/043,617, filed on Aug. 29, 2014.

(51) Int. Cl.
| | |
|---|---|
| C07D 253/08 | (2006.01) |
| C07D 401/04 | (2006.01) |
| C07D 473/00 | (2006.01) |
| C12Q 1/6823 | (2018.01) |
| A61K 51/04 | (2006.01) |

(52) U.S. Cl.
CPC ........ C12Q 1/6823 (2013.01); A61K 51/0419 (2013.01); A61K 51/0453 (2013.01); A61K 51/0455 (2013.01); C07D 253/08 (2013.01); C07D 401/04 (2013.01); C07D 473/00 (2013.01)

(58) Field of Classification Search
None
See application file for complete search history.

(56) References Cited

U.S. PATENT DOCUMENTS

| | | | |
|---|---|---|---|
| 3,985,755 A | * 10/1976 | Narayanan | C07D 409/14 546/271.7 |
| 6,770,642 B2 | 8/2004 | Cole et al. | |
| 2006/0018825 A1 | 1/2006 | Kudo et al. | |
| 2008/0267879 A1 | 10/2008 | Elmaleh et al. | |
| 2008/0299041 A1 | 12/2008 | Jeong et al. | |
| 2009/0123373 A1 | 5/2009 | Wang et al. | |
| 2009/0163464 A1 | 6/2009 | Black et al. | |
| 2010/0209345 A1 | 8/2010 | Katsifis et al. | |
| 2011/0085985 A1 | 4/2011 | Barrow et al. | |
| 2011/0160543 A1 | 6/2011 | Parsey et al. | |
| 2011/0182812 A1 | 7/2011 | Szardenings et al. | |
| 2012/0094996 A1 | 4/2012 | Fernandez et al. | |
| 2012/0263646 A1 | 10/2012 | Catoen et al. | |
| 2017/0056535 A1 | 3/2017 | Dominguez et al. | |
| 2017/0281804 A1 | 10/2017 | Dominguez et al. | |
| 2017/0283436 A1 | 10/2017 | Dominguez et al. | |

(Continued)

FOREIGN PATENT DOCUMENTS

| | | |
|---|---|---|
| JP | 2011-168515 | 9/2011 |
| WO | WO 2004/083195 | 9/2004 |

(Continued)

OTHER PUBLICATIONS

Giordanetto, Fabrizio. Discovery of novel class 1 phosphatidylinositide 3-kinases (PI3K) fragment inhibitors through structure-based virtual screening. Bioorganic & Medical Chemistry Letters. 21 (2011) 829-835.*

(Continued)

Primary Examiner — Samantha L Shterengarts
(74) Attorney, Agent, or Firm — Sheppard Mullin Richter & Hampton LLP

(57) ABSTRACT

Provided are imaging agents comprising a compound of Formula (I), or a pharmaceutically acceptable salt thereof, and methods of their use.

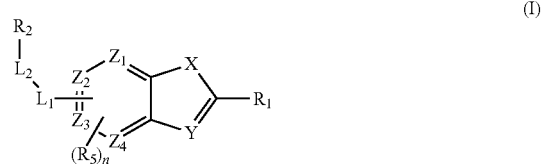

(I)

12 Claims, No Drawings

(56) References Cited

U.S. PATENT DOCUMENTS

| | | |
|---|---|---|
| 2017/0283439 A1 | 10/2017 | Dominguez et al. |
| 2019/0167821 A1 | 6/2019 | Dominguez et al. |
| 2020/0102328 A1 | 4/2020 | Dominguez et al. |

FOREIGN PATENT DOCUMENTS

| | | |
|---|---|---|
| WO | WO 2005/040337 | 5/2005 |
| WO | WO 2010/051196 | 5/2010 |
| WO | WO 2010/112093 | 10/2010 |
| WO | WO 2011/119565 | 9/2011 |

OTHER PUBLICATIONS

Database Registry Chemical Abstracts Service, Columbus, Ohio, Accession No. RN 293738-20-2, Entered STN: Oct. 9, 2000.*
Database Registry Chemical Abstracts Service, Columbus, Ohio, Accession No. RN 1367836-32-5, Entered STN: Apr. 13, 2012.*
Extended European Search Report and Opinion dated Apr. 9, 2018 for EP Application No. 15836157.6. 15 pages.
Extended European Search Report and Opinion dated May 2, 2018 for EP Application No. 15836321.8. 11 pages.
International Preliminary Report on Patentability dated Feb. 28, 2017 for PCT/US2015/047427. 6 pages.
International Preliminary Report on Patentability dated Mar. 7, 2017 for PCT/US2015/047407. 6 pages.
International Search Report and Written Opinion dated Dec. 7, 2015 for PCT/US2015/047427. 13 pages.
International Search Report and Written Opinion dated Dec. 7, 2015 for PCT/US2015/047407. 8 pages.
Mathis, et al. Synthesis and evaluation of 11C-labeled 6-substituted 2-arylbenzothiazoles as amyloid imaging agents. J Med Chem. Jun. 19, 2003;46(13):2740-54.
Serdons, et al. Synthesis and evaluation of three 18F-labeled aminophenylbenzothiazoles as amyloid imaging agents. J Med Chem. Nov. 26, 2009;52(22):7090-102.
Zeng, et al. 9Fluorine-18 radiolabeled heterocycles as PET tracers for imaging β-amyloid plaques in Alzheimer's disease. Curr Top Med Chem. 2013;13(8):909-19.
Zhang, et al. 11C-AC-5216: A Novel PET Ligand for Peripheral Benzodiazepine Receptors in the Primate Brain. J. Nucl. Med. 2007; 48:1853-1861.
Auld, et al. A Basis for Reduced Chemical Library Inhibition of Firefly Luciferase Obtained from Directed Evolution. J. Med. Chem. 2009, 52, 5, 1450-1458.
Cole, et al. Specific estrogen sulfotransferase (SULT1E1) substrates and molecular imaging probe candidates. PNAS. Apr. 6, 2010; 107 (14):6222-6227.
Database Registry Chemical Abstracts Service, Columbus, Ohio, Accession No. RN 61382-21-6, Entered STN: Nov. 16, 1984.
Database Registry Chemical Abstracts Service, Columbus, Ohio, Accession No. RN 349609-85-4, Entered STN: Aug. 1, 2001.
Database Registry Chemical Abstracts Service, Columbus, Ohio, Accession No. RN 1122521-71-4, Entered STN: Mar. 17, 2009.
Database Registry Chemical Abstracts Service, Columbus, Ohio, Accession No. RN 1485220-77-6, Entered STN: Dec. 13, 2013.
Database Registry Chemical Abstracts Service, Columbus, Ohio, Accession No. RN 332042-92-9, Entered STN: Apr. 23, 2001.
Dudkin. Bioisosteric Equivalence of Five-Membered Heterocycles. Chemistry of Heterocyclic Compounds, 2012, 48 (1), pp. 27-32.
Song Youtao. 1.2 Amyloid deposition disease. "Molecular chaperones and protein misfolding", Liaoning Science and Technology Press, Mar. 2012, the 1st edition, pp. 6-10.
Supporting Information for Cole, et al. Specific estrogen sulfotransferase (SULT1E1) substrates and molecular imaging probe candidates. PNAS. Apr. 6, 2010; 107 (14):6222-6227.

* cited by examiner

PROBES FOR IMAGING HUNTINGTIN PROTEIN

CROSS REFERENCE TO RELATED APPLICATIONS

This application is a U.S. National Stage Application under 35 U.S.C. § 371 of PCT Application No. PCT/US2015/047427, filed Aug. 28, 2015, which claims priority to U.S. Provisional Application No. 62/043,617, filed Aug. 29, 2014, which is incorporated herein by reference for all purposes.

The advent of molecular imaging approaches such as positron emission tomography (PET) and single photon emission computed tomography (SPECT) has enabled measurements of molecular and cellular mechanisms throughout the body in preclinical and clinical settings. Such measurements have widespread diagnostic utility and their use for evaluation of treatment responses and to assist drug development is expanding rapidly. The recent introduction of high-resolution molecular imaging technology is considered by many experts as a major breakthrough that will potentially lead to a revolutionary paradigm shift in health care and revolutionize clinical practice.

PET involves the administration to a subject of a positron-emitting radionuclide tracer followed by detection of the positron emission (annihilation) events in the body. The radionuclide tracer is typically composed of a targeting molecule having incorporated therein one or more types of positron-emitting radionuclides.

Many new molecular probes labeled with positron-emitting radionuclides and associated PET imaging assays are under development to target, detect, visualize, and quantify various extracellular and intracellular molecules and processes associated with diseases such as cancer, heart disease, and neurological disorders. For instance, several types of agents have been synthesized and evaluated for imaging amyloid β (Aβ) plaques in patients with Alzheimer's disease (AD) including, arylbenzothiazoles, stilbenes, imidazopyridines, pyridylbenzothiazoles, pyridylbenzoxazoles and pyridylbenzofurans (Swahn et al., *Bioorganic & Medicinal Chemistry Letters*, 20 (2010) 1976-1980). Furthermore, styrylbenzimidazole (SBIM) derivatives have been developed as agents for imaging neurofibrillary tangles (NFT), composed of hyperphosphorylated tau protein, in patients with AD. In binding experiments using recombinant tau and amyloid $\beta_{1-42}$ ($A\beta_{1-42}$) aggregates, 4-[(E)-2-(6-iodo-1H-benzimidazol-2-yl)ethenyl]-N,N-dimethylaniline (SBIM-3) showed higher affinity for the tau aggregates than $A\beta_{1-42}$ aggregates (ratio of $K_d$ values was 2.73). In in vitro autoradiography and fluorescent staining, [$^{125}$I]SBIM-3 (or SBIM-3) bound NFT in sections of AD brain tissue. In biodistribution experiments using normal mice, all [$^{125}$I] SBIM derivatives showed high initial uptake into (3.20-4.11% ID/g at 2 minutes after the injection) and rapid clearance from (0.12-0.33% ID/g at 60 minutes after the injection) the brain (Matsumura et al., *Bioorganic & Medicinal Chemistry*, 21 (2013) 3356-3362).

Huntington's disease (HD) is an inherited progressive neurodegenerative disorder, characterized by motor, cognitive, and psychiatric deficits as well as neurodegeneration and brain atrophy beginning in the striatum and the cortex and extending to other subcortical brain regions. It belongs to a family of neurodegenerative diseases caused by mutations in which an expanded CAG repeat tract results in long stretches of polyglutamine (polyQ) in the encoded protein. This family also includes dentatorubral-pallidoluysian atrophy (DRPLA), spinal and bulbar muscular atrophy (SBMA) and the spinocerebellar ataxias (SCAs). Apart from their polyQ repeats, the proteins involved are unrelated, and although they are all widely expressed in the central nervous system and peripheral tissues, they lead to characteristic patterns of neurodegeneration. In HD, the selective neurodegeneration of the γ-aminobutyric acid-releasing spiny-projection neurons of the striatum is predominant, although loss of neurons in many other brain regions has also been reported. In the unaffected population, the number of CAG repeats in the $IT_{15}$ gene that encodes the HD protein huntingtin (HTT protein) varies from 6 to 35; repeats of 36 or more define an HD allele. The length of the CAG expansion is inversely correlated with age of disease onset, with cases of juvenile onset characterized by expansions of more than 60 repeats. HD has a prevalence of 5-10 cases per 100,000 worldwide, which makes it the most common inherited neurodegenerative disorder. HTT protein is a 348-kDa multidomain protein that contains a polymorphic glutamine/proline-rich domain at its amino-terminus. The longer polyQ domain seems to induce conformational changes in the protein, which causes it to form intracellular aggregates that, in most cases, manifest as nuclear inclusions. However, aggregates can also form outside the nucleus. HTT protein is present in the nucleus, cell body, dendrites and nerve terminals of neurons, and is also associated with a number of organelles including the Golgi apparatus, endoplasmic reticulum and mitochondria.

Several clinical trials are investigating means to alleviate or reduce symptoms and slow progression in clinically diagnosed HD. Consistent with other medical conditions, treatments might be ideally initiated at or before the earliest signs of disease. There are at least two primary challenges to the design of clinical trials for pre-HD: selection of participants who are most likely to show measurable change over the course of a clinical trial, and development of outcome measures that are sensitive to interventions and can demonstrate variation over the natural history of pre-HD. In order to meet these and other challenges to preventive clinical trials, indicators of very early disease are required.

In view of the central role of the accumulation of aggregated forms of HTT protein in the pathogenesis of HD, there is a need for molecular probes that bind to such abnormalities with high sensitivity and specificity, for molecular imaging in the living subject using PET. The compounds described herein meet this and other needs.

Provided is an imaging agent comprising a compound of Formula I, or a pharmaceutically acceptable salt thereof,

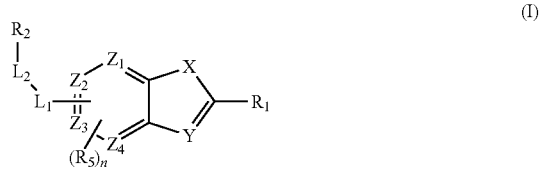

wherein
X is chosen from ($CR_3$=$CR_3$), O, NH, and S;
Y is chosen from $CR_3$ and N;
where for each occurrence, $R_3$ is independently chosen from hydrogen, halo, cyano, and lower alkyl;
$Z_1$, $Z_2$, $Z_3$, and $Z_4$ are independently chosen from CH and N, provided that at least two of $Z_1$, $Z_2$, $Z_3$, and $Z_4$ are CH;

R₁ is chosen from aryl, heteroaryl, and heterocycloalkyl, each of which is optionally substituted with one or two groups independently chosen from alkynyl, heteroaryl, cyano, optionally substituted amino, halo, and lower alkyl optionally substituted with optionally substituted amino;

$L_1$ is chosen from C(O)O, O and NR₄ or $L_1$ is absent;

R₄ is chosen from hydrogen and lower alkyl;

$L_2$ is $(CH_2)_m$ where m is 0, 1, or 2; and

R₂ is chosen from hydrogen, hydroxyl, lower alkyl, lower haloalkyl, halo, and lower alkoxy, R₅ is chosen from lower alkyl, lower alkoxy, and halo; and n is 0 or 1; or R₂ and R₅, taken together with any intervening atoms forms a 5- to 7-membered heterocycloalkyl ring, wherein the compound of Formula I, or a pharmaceutically acceptable salt thereof, is labeled with one or more positron-emitting radionuclides.

Also provided is a method of generating diagnostic images in an individual comprising administering an effective amount of an imaging agent described herein to an individual, and generating an image of at least a part of said individual.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH₂ is attached through the carbon atom.

As used herein the terms "group", "radical" or "fragment" refer to a functional group or fragment of a molecule attached to a bond or other fragments of molecules.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

When a moiety is defined as being optionally substituted, it may be substituted as itself or as part of another moiety. For example, if $R^x$ is defined as "$C_{1-6}$ alkyl or $OC_{1-6}$ alkyl, wherein $C_{1-6}$ alkyl is optionally substituted with halogen", then both the $C_{1-6}$ alkyl group alone and the $C_{1-6}$ alkyl that makes up part of the $OC_{1-6}$ alkyl group may be substituted with halogen.

The term "alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbons is named, all geometric isomers having that number of carbons are intended to be encompassed; thus, for example, "butyl" is meant to include n-butyl, sec-butyl, isobutyl and tert-butyl; "propyl" includes n-propyl and isopropyl. "Lower alkyl" refers to alkyl groups having 1 to 6 carbons.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having 1 to 6 carbons. By "cycloalkoxy" is meant a cycloalkyl group that is likewise attached through an oxygen bridge.

"Alkynyl" refers to an unsaturated branched or straight-chain alkyl group having the indicated number of carbon atoms (e.g., 2 to 8 or 2 to 6 carbon atoms) and at least one carbon-carbon triple bond derived by the removal of two molecules of hydrogen from adjacent carbon atoms of the corresponding alkyl. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl). "Lower alkynyl" refers to alkynyl groups having 2 to 6 carbons.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl" regardless of the point of attachment (e.g., both quinolin-5-yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond derived by the removal of one molecule of hydrogen from adjacent carbon atoms of the corresponding cycloalkyl. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group.

The term "halo" includes fluoro, chloro, bromo, and iodo, and the term "halogen" includes fluorine, chlorine, bromine, and iodine.

"Haloalkyl" includes straight and branched carbon chains having the indicated number of carbon atoms (e.g., 1 to 6 carbon atoms) substituted with at least one halogen atom. In instances wherein the haloalkyl group contains more than one halogen atom, the halogens may be the same (e.g., dichloromethyl) or different (e.g., chlorofluoromethyl). Examples of haloalkyl groups include, but are not limited to, chloromethyl, dichloromethyl, trichloromethyl, fluoromethyl, difluoromethyl, trifluoromethyl, chlorofluoromethyl, 2-fluoroethyl, 2,2-difluoroethyl, 2,2,2-trifluoroethyl, 1,2-difluoroethyl, 2-chloroethyl, 2,2-dichloroethyl, 2,2,2-trichloroethyl, 1,2-dichloroethyl, pentachloroethyl, and pentafluoroethyl.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,3,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzimidazole, benzotriazole, benzofuran, benzoxazole, benzisoxazole, benzoxadiazole, benzothiophene, benzothiazole, benzisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H-[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic).

Examples of monocyclic heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation $C_1$-$C_4$ alkyl), cycloalkyl, cycloalkenyl, aryl, heterocycloalkyl, heterocycloalkenyl, and heteroaryl, unless otherwise expressly defined, refer respectively to alkyl, cycloalkyl, cycloalkenyl, aryl, heterocycloalkyl, heterocycloalkenyl, and heteroaryl, wherein one or more (such as up to 5, for example, up to 3) hydrogen atoms are replaced by a substituent independently chosen from:

—$R^a$, —$OR^b$, —O($C_1$-$C_2$ alkyl)O— (e.g., methylenedioxy-), —$SR^b$, guanidine (—NHC(=NH)NH$_2$), guanidine wherein one or more of the guanidine hydrogens are replaced with a $C_1$-$C_4$ alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^aCONR^bR^a$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl;

$R^b$ is chosen from H, $C_1$-$C_6$ alkyl, aryl, and heteroaryl; and $R^c$ is chosen from hydrogen and $C_1$-$C_4$ alkyl; or $R^b$ and $R^c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —$C_1$-$C_4$ alkyl-O—$C_1$-$C_4$ alkyl, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —N($C_1$-$C_4$ alkyl)($C_1$-$C_4$ alkylheteroaryl), —NH($C_1$-$C_4$ alkylphenyl), cyano, nitro, oxo (as a substitutent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "substituted amino" refers to the group —NHR$^d$ or —NR$^d$R$^d$ where each R$^d$ is independently chosen from: optionally substituted alkyl, optionally substituted cycloalkyl, optionally substituted acyl, optionally substituted aryl, optionally substituted heteroaryl, optionally substituted heterocycloalkyl, alkoxycarbonyl, sulfinyl and sulfonyl, wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl;

where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —N($C_1$-$C_4$ alkyl)($C_1$-$C_4$ alkylheteroaryl), —NH($C_1$-$C_4$ alkylphenyl), cyano, nitro, oxo (as a substitutent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "substituted amino" also refers to the group —NR$^e$R$^f$ wherein R$^e$ and R$^f$, together with the nitrogen to which they are bound, form an optionally substituted 5- to 7-membered nitrogen-containing, non-aromatic, heterocycle which optionally contains 1 or 2 additional heteroatoms chosen from nitrogen, oxygen, and sulfur.

"Aminocarbonyl" encompasses a group of the formula —C(=O)(optionally substituted amino) wherein substituted amino is as described herein.

Compounds described herein include, but are not limited to, their optical isomers, racemates, and other mixtures thereof. In those situations, the single enantiomers or diastereoisomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. The term "isomers" refers to different compounds that have the same molecular formula. The term "stereoisomers" refers to isomers that differ only in the way the atoms are arranged in space. The term "enantiomers" refers to stereoisomers that are non-superimposable mirror images of each other. A 1:1 mixture of a pair of enantiomers is a "racemic" mixture. The symbol "(±)" may be used to designate a racemic mixture where appropriate. The term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line.

Where compounds described herein exist in various tautomeric forms, the term "compound" includes all tautomeric forms of the compound. Such compounds also include crystal forms including polymorphs and clathrates. Similarly, the term "salt" includes all tautomeric forms and crystal forms of the compound. The term "tautomers" refers to structurally distinct isomers that interconvert by tautomerization. Tautomerization is a form of isomerization and includes prototropic or proton-shift tautomerization, which is considered a subset of acid-base chemistry. Prototropic tautomerization or proton-shift tautomerization involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Pharmaceutically acceptable forms of the compounds recited herein include pharmaceutically acceptable salts, and mixtures thereof. In some embodiments, the compounds described herein are in the form of pharmaceutically acceptable salts.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, lactate, methanesulfonate, p-toluenesulfonate, 2-hydroxyethylsulfonate, benzoate, salicylate, stearate, haloalkanoate such as trifluoroacetate, and alkanoate such as acetate, HOOC—(CH$_2$)$_n$—COOH where n is 0-4, and like salts. Similarly, pharmaceutically acceptable cations include, but are not limited to sodium, potassium, calcium, aluminum, lithium, and ammonium. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The term "administering", as used herein in conjunction with a diagnostic agent, such as, for example, a positron-emitter labeled compound described herein, means administering directly into or onto a target tissue or to administer the diagnostic agent systemically to a patient whereby the diagnostic agent is used to image the tissue or a pathology associated with the tissue to which it is targeted. "Administering" a composition may be accomplished by injection, infusion, or by either method in combination with other known techniques.

The term "Curie" (Ci) is a unit of measurement of radioactivity. One Ci refers to that amount of any radioactive material that will decay at a rate of $3.7 \times 10^{10}$ disintegrations per second. The term "milliCurie" (mCi) refers to $10^{-3}$ Curie. It is understood that the International System (SI) unit of radioactivity, the Becquerel, is equal to one disintegration/second. Thus one Becquerel=$2.7 \times 10^{-11}$ Curie.

The term "diagnostic imaging", as used herein, refers to the use of electromagnetic radiation to produce images of internal structures of the human or animal body for the purpose of diagnosis.

The term "effective amount" of a compound, as used herein, is a predetermined amount calculated to achieve a desired effect such as an amount sufficient to enable the acquisition of a desired image of the target organ of an individual. In some instances the target organ is the brain.

The term "huntingtin protein" or "HTT protein", as used herein, refers to the protein encoded by the human huntingtin gene (HTT gene) located on the short (p) arm of chromosome 4 at position 16.3. More precisely, the $IT_{15}$ gene coding for the HTT protein is located from base pair 3,076,407 to base pair 3,245,686 on chromosome 4.

The term "HTT protein aggregate", as used herein refers to an insoluble fibrous amyloid comprising mis-folded HTT protein molecules.

The term "β-amyloid aggregate", as used herein refers to an insoluble fibrous amyloid comprising mis-folded β-amyloid protein molecules.

The term "imaging agent", as used herein, refers to a compound as described herein labeled with one or more positron-emitting isotopes or radionuclides. A positron-emitter labeled compound need only be enriched with a detectable isotope to a degree that permits detection with a technique suitable for the particular application.

The term "pathologic process", as used herein, refers to an altered endogenous biological process that may be associated with the aberrant production and/or functioning of proteins, peptides, RNA and other substances associated with such biological process.

The term "PET imaging", as used herein, refers to the use of a positron-emitter labeled compound to produce images of internal structures of the human or animal body.

The term "pharmaceutical composition" refers to a composition comprising at least one imaging agent described herein, whereby the composition is amenable to investigation for a specified, efficacious outcome in a mammal (for example, without limitation, a human). Those of ordinary skill in the art will understand and appreciate the techniques appropriate for determining whether a composition has a desired efficacious outcome based upon the needs of the artisan.

The term "positron-emitting radionuclide", as used herein, refers to a radioactive isotope that exhibits particular type of radioactive decay referred to as β+ decay, in which a proton inside a radionuclide nucleus is converted into a neutron while releasing a positron and an electron neutrino ($v_e$). Some examples of positron-emitting radionuclides include $^{15}$O, $^{13}$N, $^{11}$C, $^{18}$F, $^{76}$Br, and $^{124}$I. These radionuclides have half-lives of about 2, 10, 20, 110 minutes, 16 hours, and 4.2 days respectively.

The term "tomography", as used herein, refers to a process of imaging by sections. The images may be looked at individually, as a series of two-dimensional slices or together, as a computer-generated three-dimensional representation.

Provided is an imaging agent comprising a compound of Formula I, or a pharmaceutically acceptable salt thereof,

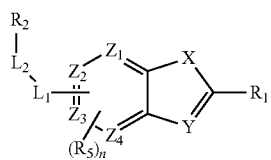

(I)

wherein
X is chosen from ($CR_3$=$CR_3$), O, NH, and S;
Y is chosen from $CR_3$ and N;

where for each occurrence, $R_3$ is independently chosen from hydrogen, halo, cyano, and lower alkyl;
$Z_1$, $Z_2$, $Z_3$, and $Z_4$ are independently chosen from CH and N, provided that at least two of $Z_1$, $Z_2$, $Z_3$, and $Z_4$ are CH;
$R_1$ is chosen from aryl, heteroaryl, and heterocycloalkyl, each of which is optionally substituted with one or two groups independently chosen from alkynyl, heteroaryl, cyano, optionally substituted amino, halo, and lower alkyl optionally substituted with optionally substituted amino;
$L_1$ is chosen from C(O)O, O and $NR_4$ or $L_1$ is absent;
$R_4$ is chosen from hydrogen and lower alkyl;
$L_2$ is $(CH_2)_m$ where m is 0, 1, or 2; and
$R_2$ is chosen from hydrogen, hydroxyl, lower alkyl, lower haloalkyl, halo, and lower alkoxy,
$R_5$ is chosen from lower alkyl, lower alkoxy, and halo; and n is 0 or 1; or
$R_2$ and $R_5$, taken together with any intervening atoms forms a 5- to 7-membered heterocycloalkyl ring,
wherein the compound of Formula I, or a pharmaceutically acceptable salt thereof, is labeled with one or more positron-emitting radionuclides.

In some embodiments, $R_1$ is phenyl or phenyl substituted with one or two groups independently chosen from cyano, optionally substituted amino, halo, lower alkyl, and lower alkyl substituted with optionally substituted amino.

In some embodiments, $R_1$ is phenyl or phenyl substituted with one or two groups independently chosen from cyano, methyl, and methyl substituted with amino, (alkyl)amino or (dialkyl)amino.

In some embodiments, $R_1$ is 2-cyanophenyl.

In some embodiments, $R_1$ is heteroaryl or heteroaryl substituted with one or two groups independently chosen from alkynyl, cyano, optionally substituted amino, halo, lower alkyl, and lower alkyl substituted with optionally substituted amino.

In some embodiments, $R_1$ is chosen from pyridine-4-yl, pyridine-2-yl, pyridine-3-yl, 1H-pyrazole-3-yl, 1,2-dihydropyridin-2-one-3-yl, 1H-indazole-4-yl, and 1H-indazole-7-yl, each of which is optionally substituted with one or two groups independently chosen from alkynyl, cyano, optionally substituted amino, halo, lower alkyl, and lower alkyl substituted with optionally substituted amino.

In some embodiments, $R_1$ is chosen from pyridine-4-yl, pyridine-2-yl, and pyridine-3-yl, each of which is optionally substituted with one or two groups independently chosen from alkynyl, cyano, optionally substituted amino, halo, lower alkyl, and lower alkyl substituted with optionally substituted amino.

In some embodiments, $R_1$ is chosen from 5-bromo-1,2-dihydropyridin-2-one-3-yl, 3-acetamido-pyridine-4-yl, 2-acetamido-pyridine-6-yl, 3-cyano-pyridine-4-yl, 3-cyano-pyridine-6-yl, 3-bromo-pyridine-4-yl, 3-bromo-pyridine-2-yl, 3-cyano-pyridine-2-yl, 3-fluoro-pyridine-4-yl, 2-cyano-pyridine-4-yl, 4-cyano-pyridine-3-yl, pyridine-4-yl and 3-ethynyl-pyridine-4-yl.

In some embodiments, $R_1$ is 3-cyano-pyridine-4-yl.

In some embodiments, $R_1$ is heterocycloalkyl or heterocycloalkyl substituted with one or two groups independently chosen from cyano, optionally substituted amino, halo, lower alkyl, and lower alkyl substituted with optionally substituted amino.

In some embodiments, $R_1$ is 5H,6H-imidazo[2,1-b][1,3] thiazole-3-yl optionally substituted with cyano or halo.

In some embodiments, $L_1$ is C(O)O.

In some embodiments, $L_1$ is O.

In some embodiments, L₁ is NR₄.

In some embodiments, R₄ is chosen from hydrogen and methyl.

In some embodiments, L₁ is NR₄ and R₄ is chosen from hydrogen and methyl.

In some embodiments, L₁ is absent.

In some embodiments, m is 0.

In some embodiments, m is 1.

In some embodiments, m is 2.

In some embodiments, R₂ is hydrogen.

In some embodiments, R₂ is chosen from hydrogen, and lower alkoxy.

In some embodiments, R₂ is hydrogen or hydroxyl.

In some embodiments, R₂ is chosen from halo, lower alkoxy, and hydroxyl.

In some embodiments, L₁ is C(O)O and m is 0.

In some embodiments, L₁ is C(O)O and m is 1.

In some embodiments, L₁ is C(O)O and m is 2.

In some embodiments, L₁ is C(O)O, m is 0, and R₂ is hydrogen.

In some embodiments, L₁ is C(O)O, m is 1, and R₂ is chosen from hydrogen and lower alkyl.

In some embodiments, L₁ is C(O)O, m is 2, and R₂ is chosen from hydrogen and lower alkyl.

In some embodiments, L₁ is O and m is 0.

In some embodiments, L₁ is O and m is 1.

In some embodiments, L₁ is O and m is 2.

In some embodiments, L₁ is O, m is 0, and R₂ is hydrogen.

In some embodiments, L₁ is O, m is 1, and R₂ is chosen from hydrogen, and lower alkoxy.

In some embodiments, L₁ is O, m is 2, and R₂ is chosen from halo, lower alkoxy, and hydroxyl.

In some embodiments, L₁ is NR₄ and m is 1.

In some embodiments, L₁ is NR₄ m is 1, and R₂ is hydrogen.

In some embodiments, L₁ is NR₄ and m is 2.

In some embodiments, L₁ is NR₄ m is 2, and R₂ is hydrogen or hydroxyl.

In some embodiments, L₁ is absent and m is 0.

In some embodiments, L₁ is absent, m is 0, and R₂ is hydrogen, bromo, or trifluoromethyl.

In some embodiments, X is O.

In some embodiments, X is S.

In some embodiments, X is (CR₃=CR₃).

In some embodiments, X is NH.

In some embodiments, Y is N.

In some embodiments, Y is CR₃.

In some embodiments, R₃ is hydrogen.

In some embodiments, R₃ is halo.

In some embodiments, R₃ is bromo.

In some embodiments, R₃ is cyano.

In some embodiments, R₃ is lower alkyl.

In some embodiments, R₃ is methyl.

In some embodiments, Z₁, Z₂, Z₃, and Z₄ are CH.

In some embodiments, Z₁ is N and Z₂, Z₃, and Z₄ are CH.

In some embodiments, Z₂ is N and Z₁, Z₃, and Z₄ are CH.

In some embodiments, Z₂ and Z₄ are N and Z₁ and Z₃ are CH.

In some embodiments, n is 0.

In some embodiments, n is 1.

In some embodiments, R₅ is chosen from lower alkyl.

In some embodiments, the compound of Formula I is chosen from

[6-methoxy-2-(pyridin-3-yl)-1,3-benzoxazole;
[2-(pyridin-3-yl)-1,3-benzoxazol-5-yl]methanol;
4-[5-(methoxymethoxy)-1-benzofuran-2-yl]-1-methyl-1H-pyrazole-3-carbonitrile;
4-(5-methoxy-1-benzofuran-2-yl)-3-methylpyridine;
3-iodo-4-(5-methoxy-1-benzofuran-2-yl)pyridine;
2-[(dimethylamino)methyl]-6-(5-methoxy-1-benzofuran-2-yl)benzonitrile;
2-bromo-6-(5-methoxy-1-benzofuran-2-yl)benzonitrile;
5-bromo-2-(5-methoxy-1-benzofuran-2-yl)benzonitrile;
4-iodo-6-(5-methoxy-1-benzofuran-2-yl)pyrimidine-5-carbonitrile;
3-(5-hydroxy-1-benzofuran-2-yl)-5H,6H-imidazo[2,1-b][1,3]thiazole-2-carbonitrile;
4-(6-methoxynaphthalen-2-yl)pyridine-3-carbonitrile;
6-methoxy-2-(2-methoxyphenyl)-1,3-benzothiazole;
4-(6-methoxy-1,3-benzothiazol-2-yl)benzonitrile;
4-(6-methoxy-1H-1,3-benzodiazol-2-yl)pyridine-3-carbonitrile;
6-methoxy-2-[3-(1H-pyrazol-5-yl)pyridin-4-yl]-1,3-benzothiazole;
4-(6-methoxy-1,3-benzothiazol-2-yl)-N-methylpyridin-3-amine;
4-(6-methoxyquinolin-2-yl)pyridine-3-carbonitrile;
4-(6-methoxy-1,3-benzothiazol-2-yl)pyridine-3-carbonitrile;
4-(5-methoxy-1-benzofuran-2-yl)pyridine-3-carbonitrile;
N-[6-(5-methoxy-1-benzofuran-2-yl)pyridin-2-yl]acetamide;
6-(5-methoxy-1-benzofuran-2-yl)pyridine-3-carbonitrile;
4-(1,3-benzothiazol-2-yl)pyridine-3-carbonitrile;
2-(6-methoxy-1,3-benzothiazol-2-yl)benzonitrile;
2-(3-bromopyridin-4-yl)-6-methoxy-1,3-benzothiazole;
2-(3-bromopyridin-4-yl)-1,3-benzothiazol-6-ol;
2-(3-bromopyridin-2-yl)-6-methoxy-1,3-benzothiazole;
2-(6-methoxy-1,3-benzothiazol-2-yl)pyridine-3-carbonitrile;
2-(3-fluoropyridin-4-yl)-6-methoxy-1,3-benzothiazole;
4-[6-(dimethylamino)-1,3-benzothiazol-2-yl]pyridine-3-carbonitrile;
4-(6-methoxy-1,3-benzothiazol-2-yl)pyridine-2-carbonitrile;
2-(6-methoxy-1,3-benzoxazol-2-yl)benzonitrile;
N-[4-(6-methoxy-1,3-benzothiazol-2-yl)pyridin-3-yl]acetamide;
2-(3-bromopyridin-4-yl)-6-(2-fluoroethoxy)-1,3-benzothiazole;
4-[6-(2-fluoroethoxy)-1,3-benzothiazol-2-yl]pyridine-3-carbonitrile;
4-(5-methoxy-1,3-benzothiazol-2-yl)pyridine-3-carbonitrile;
4-[6-(trifluoromethyl)-1,3-benzothiazol-2-yl]pyridine-3-carbonitrile;
4-[5-(2-fluoroethoxy)-1-benzofuran-2-yl]pyridine-3-carbonitrile;
3-(6-methoxy-1,3-benzothiazol-2-yl)pyridine-4-carbonitrile;
5-bromo-3-{5-bromofuro[2,3-b]pyridin-2-yl}-1,2-dihydropyridin-2-one;
2-{5-methoxyfuro[2,3-c]pyridin-2-yl}benzonitrile;
2-{5-bromofuro[2,3-b]pyridin-2-yl}benzonitrile;
2-{5-methoxyfuro[2,3-b]pyridin-2-yl}benzonitrile;
4-(5-methoxy-1-benzofuran-2-yl)-1H-indazole;
7-(5-methoxy-1-benzofuran-2-yl)-1H-indazole;
4-[5-(methoxymethoxy)-1-benzofuran-2-yl]pyridine-3-carbonitrile;
4-(5-hydroxy-1-benzofuran-2-yl)pyridine-3-carbonitrile;
4-[5-(2-methoxyethoxy)-1-benzofuran-2-yl]pyridine-3-carbonitrile;
2-(5-methoxy-1-benzofuran-2-yl)pyridine-3-carbonitrile;

4-{5-methoxyfuro[2,3-c]pyridin-2-yl}pyridine-3-carbonitrile;
4-{6-methoxyfuro[3,2-b]pyridin-2-yl}pyridine-3-carbonitrile;
4-(3-bromo-5-methoxy-1-benzofuran-2-yl)pyridine;
5-methoxy-2-(pyridin-4-yl)-1-benzofuran-3-carbonitrile;
4-[5-(2-hydroxyethoxy)-1-benzofuran-2-yl]pyridine-3-carbonitrile;
2-{4,6,10-trioxa-12-azatricyclo[7.3.0.0$^{3,7}$]dodeca-1(9),2,7,11-tetraen-11-yl}benzonitrile;
4-{5-[(2-hydroxyethyl)(methyl)amino]-1-benzofuran-2-yl}pyridine-3-carbonitrile;
2-{2-methoxyfuro[2,3-d]pyrimidin-6-yl}benzonitrile;
4-(6-methoxy-1,3-benzoxazol-2-yl)pyridine-3-carbonitrile;
3-(5-methoxy-1-benzofuran-2-yl)-5H,6H-imidazo[2,1-b][1,3]thiazole-2-carbonitrile;
3-ethynyl-4-(5-methoxy-1-benzofuran-2-yl)pyridine;
4-(5-methoxy-3-methyl-1-benzofuran-2-yl)pyridine-3-carbonitrile;
4-[(dimethylamino)methyl]-2-(5-methoxy-1-benzofuran-2-yl)benzonitrile;
2-(3-Methylphenyl)-1,3-benzoxazol-5-amine;
2-(Pyridin-3-yl)-1,3-benzoxazol-5-amine;
2-(Pyridin-4-yl)-1,3-benzoxazol-5-amine; and
2-(3-Methylphenyl)-[1,3]oxazolo[5,4-b]pyridin-6-amine.

The compounds of Formula I, or a pharmaceutically acceptable salt thereof are labeled with one or more positron-emitting radionuclides. Suitable positron-emitting radionuclides that may be incorporated in the compounds of described herein, but are not limited to, $^{11}$C, $^{13}$N, $^{15}$O, $^{18}$F, $^{52}$Fe, $^{62}$Cu, $^{64}$Cu, $^{68}$Ga, $^{74}$As, $^{82}$Rb, $^{89}$Zr, $^{122}$I, and $^{124}$I.

In some embodiments, the one or more positron-emitting radionuclides are selected from: $^{11}$C, $^{13}$N, $^{15}$O, $^{18}$F, $^{76}$Br, and $^{124}$I. In some embodiments the one or more positron-emitting radionuclides are selected from $^{11}$C, $^{13}$N, $^{15}$O, and $^{18}$F.

Non-metal radionuclides may be covalently linked to the compounds described herein by a reaction well known from the state of art. When the radionuclide is a metallic positron-emitter, it is understood that labeling may require the use of a chelating agent. Such chelating agents are well known from the state of the art.

A PET imaging agent may be labelled with the positron emitter $^{11}$C or $^{18}$F. Methods for the introduction of $^{11}$C may include, but are not limited to, alkylation with [$^{11}$C]iodomethane or [$^{11}$C]methyl triflate. Carbon-11 has a half-life of approximately 20 minutes, thus $^{11}$C needs to be generated in an on-site cyclotron, and is generally produced as [$^{11}$C] carbon dioxide. The [$^{11}$C]carbon dioxide is converted to the chemical species appropriate for the radiosynthesis (generally [$^{11}$C]iodomethane or the like), and the synthesis of the radiopharmaceutical is completed and used on-site in a PET imaging study after the appropriate radiochemical purity and specific activity have been determined. Typical methods of introducing $^{18}$F may include but are not limited to displacement of a halide, tosylate, or other leaving group with [$^{18}$F]tetrabutylamonium fluoride or [$^{18}$F]potassium fluoride kryptofix-222. Fluorine-18 has a half life of approximately 110 minutes, thus synthesis of [$^{18}$F] radiopharmaceuticals need not necessarily have to occur at the site of the cyclotron nor proximal to the PET imaging study center. General methods for the introduction of these positron emitters are described in the literature (Miller et al., *Angewandte Chemie International Edition*, 47 (2008), 8998-9033).

Provided are methods of generating diagnostic images in an individual comprising administering an effective amount of an imaging agent described herein to an individual, and generating an image of at least a part of the individual.

Also provided are methods of generating diagnostic images in a biological sample comprising contacting the biological sample with an effective amount of an imaging agent described herein and generating an image of the positron-emitter labeled compound associated with the biological sample. In this method both the contacting and the generating may be conducted in vitro, alternatively the contacting is in vivo and the generating in vitro.

Also provided are methods for detecting the presence or absence of a neurodegenerative pathologic process associated with huntingtin protein (HTT protein) in an individual comprising: administering an effective amount of a positron-emitter labeled compound described herein; generating an image to detect the presence or absence of HTT protein aggregates in the brain of the individual; and detecting the presence or absence of the pathologic process. In some embodiments, the HTT protein aggregates are present in the basal ganglia of the brain of the individual. In some embodiments, the pathologic process is Huntington's disease (HD). In some embodiments, the effective amount of the imaging agent comprises from about 0.1 to about 20 mCi. In some embodiments, the effective amount of the imaging agent comprises about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Also provided are diagnostic methods of using the imaging agents to monitor disease progression in a patient by quantifying the change in levels of the target aggregates in the patient.

Also provided are methods for detecting the presence or absence of a neurodegenerative pathologic process associated with huntingtin protein (HTT protein) in an individual comprising: administering an effective amount of a positron-emitter labeled compound described herein; generating an image to detect the presence or absence of HTT protein aggregates in the individual; and detecting the presence or absence of the pathologic process. In some embodiments, the HTT protein monomers or aggregates are present in the brain, liver, heart, or muscle of said individual. In some embodiments, the HTT protein aggregates are present in the basal ganglia, cortex, hippocampus, or brain stem of the brain of the individual. In some embodiments, the pathologic process is Huntington's disease (HD). In some embodiments, the effective amount of the imaging agent comprises from about 0.1 to about 20 mCi. In some embodiments, the effective amount of the imaging agent comprises about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Also provided are methods for detecting the presence or absence of a neurodegenerative pathologic process associated with β-amyloid protein in an individual comprising: administering an effective amount of a positron-emitter labeled compound described herein; generating an image to detect the presence or absence of β-amyloid protein aggregates in the individual; and detecting the presence or absence of the pathologic process. In some embodiments, the β-amyloid protein monomers or aggregates are present in the brain, liver, heart, or muscle of said individual. In some embodiments, the β-amyloid protein aggregates are present in the basal ganglia, cortex, hippocampus, or brain stem of the brain of the individual. In some embodiments, the pathologic process is Alzheimer's Disease (AD). In some embodiments, the effective amount of the imaging agent comprises from about 0.1 to about 20 mCi. In some embodiments, the effective amount of the imaging agent comprises about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Provided herein are compounds having suitable HTT protein aggregate or β-amyloid protein aggregate binding kinetics to function as efficient imaging agents for HTT protein aggregates or β-amyloid protein aggregates. The requirements of the compounds of the invention to function as efficient imaging agents for HTT protein aggregates are: 1) a high affinity for HTT protein aggregates; 2) a low affinity for nearby structures; 3) slow dissociation kinetics from HTT protein aggregates, which may conveniently be expressed as the dissociation rate constant $k_{diss}$ as defined in the following equation, wherein A and B refer to the HTT protein aggregate and the imaging agent, and $k_{assn}$ is the association rate constant.

$$d[AB]/dt = k_{assn}[A][B] - k_{diss}[AB]$$

The part of the brain most affected by HD, and thus most likely to contain HTT protein abnormalities, is a group of nerve cells at the base of the brain known collectively as the basal ganglia. The basal ganglia organize muscle-driven movements of the body, or "motor movement." The major components of the basal ganglia are the caudate and the putamen (together known as the striatum) and the globus pallidus (external and internal regions). The substantia nigra and the subthalamic nucleus are often included as part of the basal ganglia as well.

The term basal ganglia, refers to a group of subcortical nuclei responsible primarily for motor control, as well as other roles such as motor learning, executive functions and behaviors, and emotions. Disruption of the basal ganglia network forms the basis for several movement disorders. Normal function of the basal ganglia requires fine tuning of neuronal excitability within each nucleus to determine the exact degree of movement facilitation or inhibition at any given moment. This is mediated by the complex organization of the striatum, where the excitability of medium spiny neurons is controlled by several pre- and postsynaptic mechanisms as well as interneuron activity, and secured by several recurrent or internal basal ganglia circuits. The motor circuit of the basal ganglia has two entry points, the striatum and the subthalamic nucleus, and an output, the globus pallidus pars interna, which connects to the cortex via the motor thalamus.

Provided are methods for imaging part of the brain of an individual involving administering a positron-emitter labeled compound described herein, or a pharmaceutically acceptable salt thereof to the individual, e.g. into the individual's vascular system, from where it passes through the blood-brain barrier, and then generating an image of at least the part of the individual's brain to which the compound has distributed.

Also provided are pharmaceutical compositions comprising an effective amount of a positron-emitter labeled compound described herein, or a pharmaceutically acceptable salt thereof, together with one or more pharmaceutically-acceptable adjuvants, excipients or diluents.

An imaging agent or pharmaceutical composition thereof may be administered to a patient in need of treatment via any suitable route. Routes of administration may include, for example, parenteral administration (including subcutaneous, intramuscular, intravenous, by means of, for example a drip patch). Further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

An imaging agent or pharmaceutical composition thereof may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

Also provided are uses of positron-emitter labeled compounds described herein for the manufacture of an imaging agent for use in a method of diagnosis of an individual.

Provided are methods of generating diagnostic images comprising positron emission tomography (PET). PET involves the administration of a positron-emitting radionuclide tracer to an individual. Once the tracer has had sufficient time to associate with the target of interest, the individual is placed within in a scanning device comprising of a ring of scintillation detectors. An emitted positron travels through the individual's tissue for a short (isotope-dependent) distance, until it interacts with an electron. The interaction annihilates both the electron and the positron, producing a pair of photons moving in approximately opposite directions. These are detected when they reach a scintillator in the scanning device. Photons that do not arrive in pairs are ignored.

Also provided are methods of generating diagnostic images comprising PET with concurrent computed tomography imaging (PET/CT), or with concurrent magnetic resonance imaging (PET/MRI). Computed tomography uses X-rays to show the structure of the brain, while magnetic resonance imaging uses magnetic fields and radio waves.

Other uses of the disclosed imaging agents and methods will become apparent to those skilled in the art based upon, inter alia, a review of this disclosure.

As will be recognized, the steps of the methods described herein need not be performed any particular number of times or in any particular sequence. Additional objects, advantages and novel features of the disclosure will become apparent to those skilled in the art upon examination of the following examples thereof, which are intended to be illustrative and not intended to be limiting.

EXAMPLES

General Experimental Details

Commercially available reagents and solvents (HPLC grade) were used without further purification. $^1$H NMR spectra were recorded on a Bruker DRX 500 MHz spectrometer or a Bruker DPX 250 MHz spectrometer in deuterated solvents. Chemical shifts (δ) are in parts per million. SCX chromatography was performed with Biotage Isolute Flash SCX-2 loading the sample in methanol and eluting with methanol then 5% ammonia in methanol.

Analytical HPLC-MS (METCR1278), was performed on Shimadzu LCMS-2010EV systems using reverse phase Atlantis dC18 columns (3 μm, 2.1×50 mm), gradient 5-100% B (A=water/0.1% formic acid, B=acetonitrile/0.1% formic acid) over 3 minutes injection volume 3 μL, flow=1.0 mL/minute. UV spectra were recorded at 215 nm using a SPD-M20A photo diode array detector. Mass spectra were obtained over the range m/z 150 to 850 at a sampling rate of 2 scans per second using a LCMS2010EV. Data were integrated and reported using Shimadzu LCMS-Solutions and PsiPort software.

Alternatively, (METCR1416) analytical HPLC-MS on Shimadzu LCMS-2010EV systems using reverse phase Water Atlantis dC18 columns (3 μm, 2.1×100 mm), gradient 5-100% B (A=water/0.1% formic acid, B=acetonitrile/0.1% formic acid) over 7 minutes, injection volume 3 μL, flow=0.6 mL/minute. UV spectra were recorded at 215 nm using a SPD-M20A photo diode array detector. Mass spectra were obtained over the range m/z 150 to 850 at a sampling rate of 2 scans per second using a LCMS2010EV. Data were integrated and reported using Shimadzu LCMS-Solutions and PsiPort software.

Alternatively, (MET-uHPLC-AB-101) analytical HPLC-MS were performed on a Waters Acquity UPLC system with Waters PDA and ELS detectors using a Phenomenex Kinetex-XB C-18 column, (1.7 μM, 2.1 mm×100 mm) at a column temperature of 40° C., gradient 5-100% B (A=water/0.1% formic acid; B=acetonitrile/0.1% formic acid) over 5.3 minutes, then 100% B for 0.5 minute, flow=0.6 mL/minute. UV spectra were recorded at 215 nm using a Waters Acquity photo diode array. Mass spectra were obtained over the range m/z 150 to 850 at a sampling rate of 5 scans per second using a Waters SQD. Data were integrated and reported using Waters MassLynx and OpenLynx software.

All example compounds display an LC purity of >95% unless stated otherwise.
Commercial Compounds

Method 1

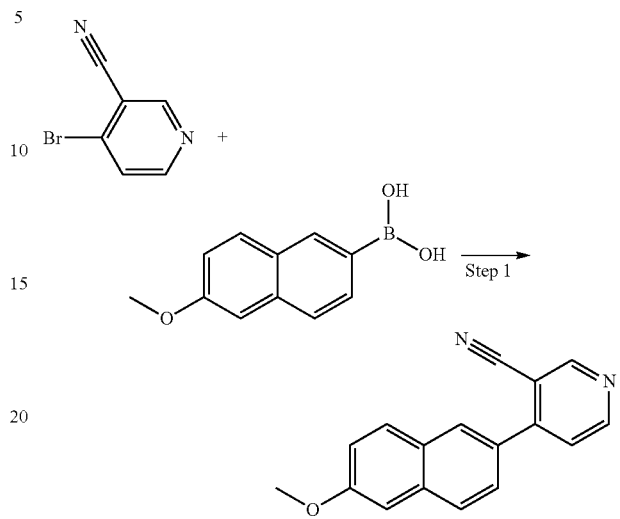

Scheme for Method 1

Step 1, Method 1: 4-(6-Methoxynaphthalen-2-yl)pyridine-3-carbonitrile

4-Bromopyridine-3-carbonitrile (200 mg, 1.09 mmol), (6-methoxynaphthalen-2-yl)boronic acid (331 mg, 1.64 mmol) and sodium carbonate (231 mg, 2.19 mmol) were suspended in toluene (10 mL) and water (5 mL) and the mixture degassed. Tetrakis(triphenylphosphine)palladium (0) (63 mg, 0.05 mmol) was added and the mixture was heated at 90° C. for 4 hours under a nitrogen atmosphere. The mixture was cooled to room temperature and extracted with ethyl acetate (3×10 mL), dried over sodium sulphate, filtered and evaporated. Purification by FCC (silica, 15-100% ethyl acetate in heptane), trituration with diethyl ether (10 mL) and drying under vacuum gave the title compound 160 mg (56% yield) as a tan powder.

Example 1, Method 1: 4-(6-Methoxynaphthalen-2-yl)pyridine-3-carbonitrile $δ_H$ NMR (500 MHz, DMSO) 9.13 (s, 1H) 8.91 (d, J=5.20 Hz, 1H) 8.22 (s, 1H) 8.03 (d, J=8.51 Hz, 1H) 7.98 (d, J=8.98

TABLE 1

| Example | Structure | Mol. Weight | IUPAC Name | LCMS data |
|---|---|---|---|---|
| 1 | 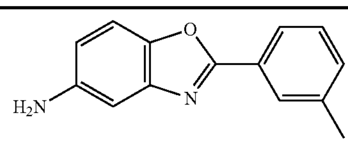 | 224.26 | 2-(3-Methylphenyl)-1,3-benzoxazol-5-amine | Tr(MET-uHPLC-AB-101) = 2.15 min, (ES$^+$) (M + H)$^+$ 225 |
| 2 | 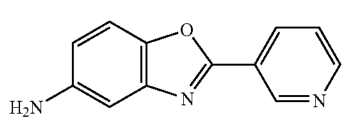 [SMILES: Nc1ccc2oc(-c3cccnc3)nc2c1] | 211.22 | 2-(Pyridin-3-yl)-1,3-benzoxazol-5-amine | Tr(MET-uHPLC-AB-101) = 1.04 min, (ES$^+$) (M + H)$^+$ 212 |
| 3 | 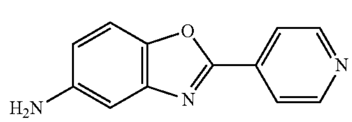 [SMILES: Nc1ccc2oc(-c3ccncc3)nc2c1] | 211.22 | 2-(Pyridin-4-yl)-1,3-benzoxazol-5-amine | Tr(MET-uHPLC-AB-101) = 0.94 min, (ES$^+$) (M + H)$^+$ 212 |

Hz, 1H) 7.82 (d, J=5.20 Hz, 1H) 7.77 (dd, J=8.51, 1.73 Hz, 1H) 7.45 (d, J=2.21 Hz, 1H) 7.28 (dd, J=8.83, 2.52 Hz, 1H) 3.92 (s, 3H). Tr(METCR1416)=4.21 min, (ES⁺) (M+H)⁺ 261.

The following example was prepared using Method 1 described above:

TABLE 2

| Example | Structure | Mol. Weight | IUPAC Name | LCMS data |
|---|---|---|---|---|
| 1 | 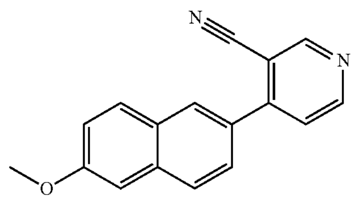 [SMILES: COc1ccc2cc(-c3ccncc3C#N)ccc2c1] | 260.29 | 4-(6-Methoxynaphthalen-2-yl)pyridine-3-carbonitrile | Tr(METCR1416) = 4.21 min, (ES⁺) (M + H)⁺ 261 |

Method 2

Scheme for Method 2

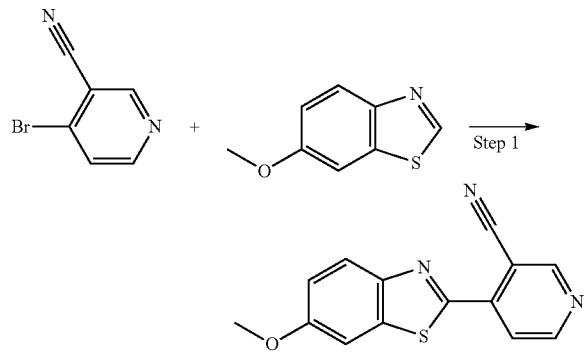

Step 1, Method 2: 4-(6-Methoxy-1,3-benzothiazol-2-yl)pyridine-3-carbonitrile

To a degassed, stirred mixture of 6-methoxy-1,3-benzothiazole (324 mg, 1.96 mmol, as described in Tetrahedron 53, (1997), 17029-17038), 4-bromopyridine-3-carbonitrile (436 mg, 2.38 mmol), copper(I) bromide (59 mg, 0.41 mmol), caesium carbonate (642 mg, 1.97 mmol) and molecular sieves in dry N,N-dimethylformamide (16 mL) was added palladium-tri-tert-butylphosphane (1:2) (49 mg, 0.1 mmol). The mixture was degassed before heating to 150° C. under nitrogen gas for 16 hours. The cooled reaction mixture was filtered through 'Kieselguhr' and washed with ethyl acetate (4×10 mL). A 1:1 mixture of water and brine (100 mL) was added to the filtrate and the two-phase system filtered and washed with ethyl acetate (20 mL). The aqueous layer was extracted with ethyl acetate (2×20 mL). The combined organic layers were washed with a 1:1 mixture of water and brine (3×80 mL). The second aqueous washings were back extracted with ethyl acetate (10 mL); the organic layers were combined and washed with brine (50 mL), dried over magnesium sulphate, filtered and concentrated. Crude material was purified by FCC (silica, 0-80% ethyl acetate in heptane), sonicated in tert-butyl methyl ether (2 mL), filtered, washed with tert-butyl methyl ether (1×2 mL and 2×1 mL) and dried to give the title compound 40 mg (7.6% yield) as a beige solid.

Example 1, Method 2: 4-(6-Methoxy-1,3-benzothiazol-2-yl)pyridine-3-carbonitrile $\delta_H$ NMR (500 MHz, DMSO) 9.20 (s, 1H) 8.99 (d, J=5.20 Hz, 1H) 8.15 (d, J=5.36 Hz, 1H) 8.08 (d, J=8.98 Hz, 1H) 7.88 (d, J=2.36 Hz, 1H) 7.25 (dd, J=8.99, 2.36 Hz, 1H) 3.89 (s, 3H). Tr(METCR1416)=4.02 min, (ES⁺) (M+H)⁺ 268.

The following examples were prepared using Method 2 described above:

TABLE 3

| Example | Structure | Mol. Weight | IUPAC Name | LCMS data |
|---|---|---|---|---|
| 1 | 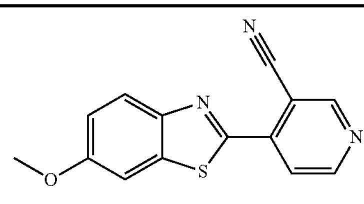 | 267.31 | 4-(6-Methoxy-1,3-benzothiazol-2-yl)pyridine-3-carbonitrile | Tr(METCR1416) = 4.02 min, (ES⁺) (M + H)⁺ 268 |
| 2 | 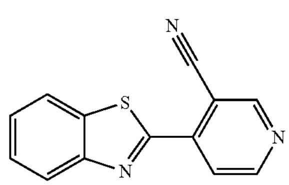 [SMILES: N#Cc1cnccc1-c1nc2ccccc2s1] | 237.28 | 4-(1,3-Benzothiazol-2-yl)pyridine-3-carbonitrile | Tr(MET-uHPLC-AB-101) = 2.90 min, (ES⁺) (M + H)⁺ 238 |

TABLE 3-continued

| Example | Structure | Mol. Weight | IUPAC Name | LCMS data |
|---|---|---|---|---|
| 3 | 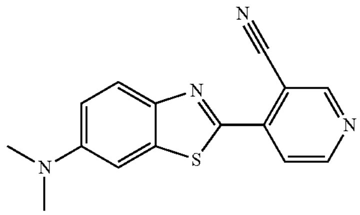 [SMILES: CN(C)c1ccc2nc(-c3ccncc3C#N)sc2c1] | 280.35 | 4-[6-(Dimethylamino)-1,3-benzothiazol-2-yl]pyridine-3-carbonitrile | Tr(MET-uHPLC-AB-101) = 3.26 min, (ES⁺) (M + H)⁺ 281 |
| 4 | 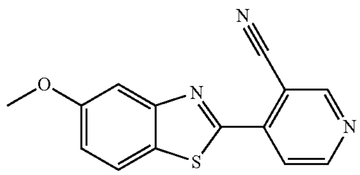 [SMILES: COc1ccc2sc(-c3ccncc3C#N)nc2c1] | 267.31 | 4-(5-Methoxy-1,3-benzothiazol-2-yl)pyridine-3-carbonitrile | Tr(MET-uHPLC-AB-101) = 3.04 min, (ES⁺) (M + H)⁺ 268 |

Method 3

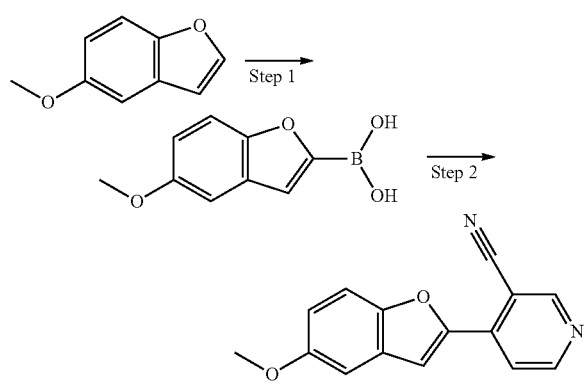

Scheme for Method 3

Step 1, Method 3:
(5-Methoxy-1-benzofuran-2-yl)boronic acid 2.5 M n-butyllithium in hexanes (2.8 mL, 7.00 mmol) was added slowly to a solution of 5-methoxy-1-benzofuran (1.0 g, 6.75 mmol) in dry tetrahydrofuran (15 mL) at −78° C. under a nitrogen atmosphere. After 1 hour stirring at −78° C., triisopropylborate (3.12 mL, 13.5 mmol) was added drop-wise and the mixture stirred for 30 minutes at −78° C. The dry ice bath was removed, 2 M aqueous hydrochloric acid (20 mL) was added and the mixture allowed to warm to room temperature whilst stirring overnight. The reaction mixture was poured into water (25 mL) and extracted with diethyl ether (3×20 mL). The combined organics were washed with brine (20 mL), dried over magnesium sulphate, filtered and concentrated. Dichloromethane (20 mL) was added and the mixture sonicated for 10 minutes. The minimum amount of methanol (circa 1 mL) was added to fully dissolve the solids and the solution sonicated for a 10 minutes. Heptane (20 mL) was added and the precipitated solids collected by vacuum filtration and allowed to dry under vacuum for 2 hours to give the title compound 476 mg (37% yield) as a white solid. $\delta_H$ NMR (500 MHz, DMSO) 8.53 (s, 2H), 7.46 (d, J=8.94 Hz, 1H), 7.39 (s, 1H), 7.19 (d, J=2.51 Hz, 1H), 6.93 (dd, J=2.60, 8.92 Hz, 1H), 3.78 (s, 3H).

Step 2, Method 3: 4-(5-Methoxy-1-benzofuran-2-yl)pyridine-3-carbonitrile

4-Bromopyridine-3-carbonitrile (150 mg, 0.82 mmol), (5-methoxy-1-benzofuran-2-yl)boronic acid (236 mg, 1.23 mmol), sodium carbonate (174 mg, 1.64 mmol) and tetrakistriphenylphosphinepalladium(0) (47 mg, 0.04 mmol) were suspended in toluene (4 mL) and water (1 mL). The mixture was heated at 90° C. for 3.5 hours under a nitrogen atmosphere before being allowed to cool and stirred overnight at room temperature. The reaction mixture was heated to 90° C. for 3 hours then treated with tetrakis(triphenylphosphine)palladium(0) (47 mg, 0.04 mmol) and heated to 90° C. for 1 hour. The reaction mixture was allowed to cool to room temperature then diluted with ethyl acetate (15 mL) and washed with water (3×15 mL). The organic layer was washed with brine (2×15 mL), dried over magnesium sulphate, filtered and concentrated. The crude material was purified by FCC (silica, 12-100% ethyl acetate in heptane) and dried in a vacuum oven at 40° C. for 2 hours to give the title compound 15.9 mg (8% yield) as an off-white solid.

Example 1, Method 3: 4-(5-Methoxy-1-benzofuran-2-yl)pyridine-3-carbonitrile $\delta_H$ NMR (500 MHz, DMSO) 9.12 (s, 1H), 8.92 (d, J=5.40 Hz, 1H), 8.07 (d, J=5.38 Hz, 1H), 7.95 (s, 1H), 7.63 (d, J=9.01 Hz, 1H), 7.37 (d, J=2.51 Hz, 1H), 7.09 (dd, J=2.61, 9.01 Hz, 1H), 3.82 (s, 3H). Tr(METCR1416)=4.39 min, (ES⁺) (M+H)⁺ 251.

The following examples were prepared using Method 3 described above:

TABLE 4

| Example | Structure | Mol. Weight | IUPAC Name | LCMS data |
|---|---|---|---|---|
| 1 | 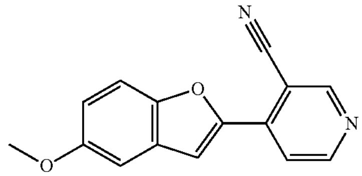 [SMILES: COc1ccc2oc(-c3ccncc3C#N)cc2c1] | 250.25 | 4-(5-Methoxy-1-benzofuran-2-yl)pyridine-3-carbonitrile | Tr(METCR1416) = 4.39 min, (ES⁺) (M + H)⁺ 251 |
| 2 | 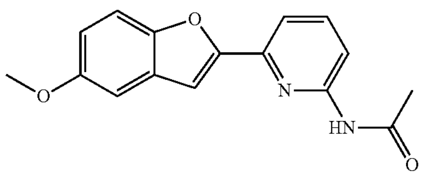 [SMILES: COc1ccc2oc(-c3cccc(NC(C)=O)n3)cc2c1] | 282.29 | N-[6-(5-Methoxy-1-benzofuran-2-yl)pyridin-2-yl]acetamide | Tr(MET-uHPLC-AB-101) = 3.16 min, (ES⁺) (M + H)⁺ 283 |
| 3 | 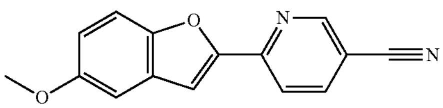 | 250.25 | 6-(5-Methoxy-1-benzofuran-2-yl)pyridine-3-carbonitrile | Tr(MET-uHPLC-AB-101) = 3.40 min, (ES⁺) (M + H)⁺ 251 |
| 4 | 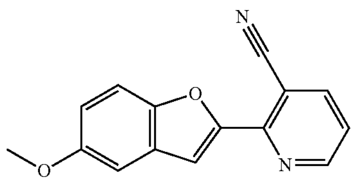 [SMILES: COc1ccc2oc(-c3ncccc3C#N)cc2c1] | 250.25 | 2-(5-Methoxy-1-benzofuran-2-yl)pyridine-3-carbonitrile | Tr(MET-uHPLC-AB-101) = 3.13 min, (ES⁺) (M + H)⁺ 251 |
| 5 | 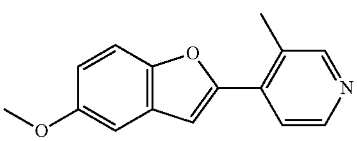 [SMILES: COc1ccc2oc(-c3ccncc3C)cc2c1] | 239.27 | 4-(5-Methoxy-1-benzofuran-2-yl)-3-methylpyridine | Tr(MET-uHPLC-AB-101) = 1.87 min, (ES⁺) (M + H)⁺ 240 |

Method 4

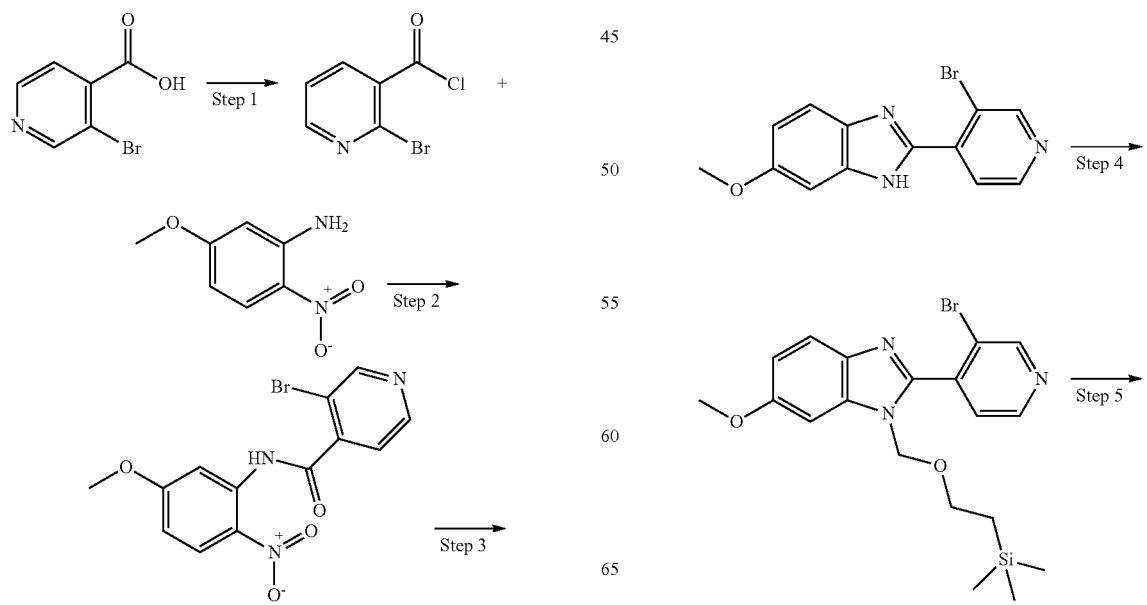

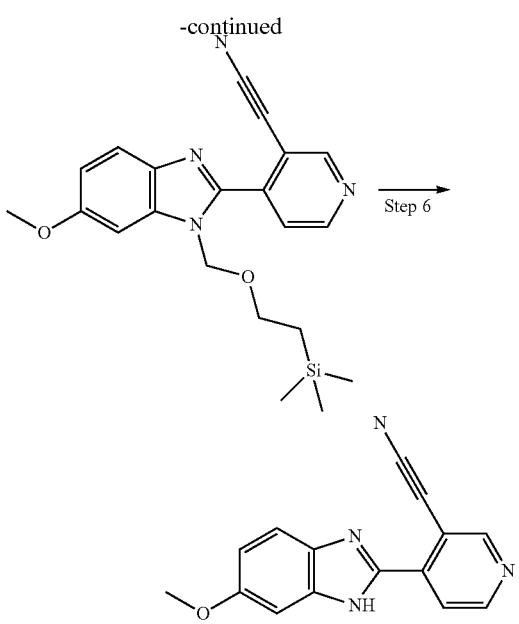

Step 1, Method 4: 2-Bromopyridine-3-carbonyl chloride hydrochloride

3-Bromopyridine-4-carboxylic acid (2.0 g, 9.90 mmol) was dissolved in dichloromethane (20 mL) with stirring under nitrogen and cooled to 0° C. Oxalyl chloride (2.55 mL, 29.7 mmol) was added followed by N,N-dimethylformamide (1 drop). The reaction mixture was then stirred at 0° C. warming to room temperature and after 1.5 hours the reaction mixture was concentrated to give the title compound 2.54 g (100% yield) as a yellow solid which was used directly in the next step.

Step 2, Method 4: 3-Bromo-N-(4-methoxy-2-nitrophenyl)pyridine-4-carboxamide

3-Bromopyridine-4-carbonyl chloride hydrochloride (2.27 g, 8.83 mmol) was dissolved in dichloromethane (20 mL) with stirring under nitrogen at room temperature and cooled to 0° C. 5-Methoxy-2-nitroaniline (1.35 g, 8.03 mmol) was added followed by triethylamine (2.35 mL, 16.9 mmol). The reaction mixture was then stirred at 0° C. to room temperature for 23.5 hours then potassium carbonate (1.1 g, 8.03 mmol) and methanol (5 mL) were added. The reaction mixture was stirred at room temperature for 1.5 hours and concentrated. The residue was dissolved in dichloromethane (20 mL) and washed with water (20 mL), 10% aqueous citric acid (20 mL), saturated aqueous sodium hydrogen carbonate (20 mL) and brine (20 mL). The organic solution was dried over magnesium sulphate, filtered and concentrated. Purification by FCC (silica, 0-50% ethyl acetate in heptane) gave the title compound 1.50 g (53% yield) as an off-white solid. $\delta_H$ NMR (500 MHz, chloroform) 10.54 (s, 1H), 8.89 (s, 1H), 8.77 (d, J=9.3 Hz, 1H), 8.69 (d, J=4.9 Hz, 1H), 7.73 (d, J=3.0 Hz, 1H), 7.52 (d, J=4.8 Hz, 1H), 7.32 (dd, J=9.3, 3.0 Hz, 1H), 3.90 (s, 3H). Tr(METCR1278)=1.83 min, (ES$^+$) (M+H)$^+$ 352/354.

Step 3, Method 4: 2-(3-Bromopyridin-4-yl)-6-methoxy-1H-1,3-benzodiazole 2-(3-Bromopyridine-4-amido)-5-methoxy-nitrobenzene (500 mg, 1.42 mmol) was dissolved in ethanol (2.5 mL) with stirring at room temperature and acetic acid (5 mL) was added. Iron powder (795 mg, 14.2 mmol) was added and the reaction mixture heated to reflux. After 20 hours the reaction mixture was cooled to room temperature, filtered through celite and concentrated. Ethyl acetate (15 mL) and water (15 mL) were added and the layers separated. The organic solution was washed with water (10 mL), saturated aqueous sodium hydrogen carbonate (2×10 mL) and brine (10 mL). The organic solution was dried over magnesium sulphate, filtered and concentrated. Purification by FCC (silica, 0-66% ethyl acetate in heptane) gave the title compound 288 mg (64% yield) as a yellow powder. $\delta_H$ NMR (500 MHz, chloroform) 8.84 (s, 1H), 8.63 (s, 1H), 8.30 (s, 1H), 7.64 (d, J=8.8 Hz, 1H), 7.15 (s, 1H), 7.02 (d, J=8.6 Hz, 1H), 3.89 (s, 3H). Tr(METCR1278)=1.51 min, (ES$^+$) (M+H)$^+$ 304/306.

Step 4, Method 4: 2-(3-Bromopyridin-4-yl)-6-methoxy-1-{[2-(trimethylsilyl)ethoxy]methyl}-1H-1,3-benzodiazole 2-(3-Bromopyridin-4-yl)-6-methoxy-1H-1,3-benzodiazole (280 mg, 0.92 mmol) was dissolved in N,N-dimethylformamide (3 mL) with stirring under nitrogen at room temperature. Potassium carbonate (159 mg, 1.15 mmol) was added followed by [2-(chloromethoxy)ethyl](trimethyl)silane (180 µL, 1.01 mmol). The reaction mixture was stirred at room temperature for 24 hours and the reaction mixture concentrated. The residue was dissolved in ethyl acetate (10 mL) and water (10 mL) and the layers separated. The organic layer was washed with water (2×10 mL) and brine (2×10 mL), dried over magnesium sulphate, filtered and concentrated. Purification by FCC (silica, 0-50% ethyl acetate in heptane) gave the title compound 136 mg (34% yield) as a pale orange oil. Tr(METCR1278)=2.31 min, (ES$^+$) (M+H)$^+$ 434/436.

Step 5, Method 4: 4-(6-Methoxy-1-{[2-(trimethylsilyl)ethoxy]methyl}-1H-1,3-benzodiazol-2-yl)pyridine-3-carbonitrile 2-(3-Bromopyridin-4-yl)-6-methoxy-1-{[2-(trimethylsilyl)ethoxy]methyl}-1H-1,3-benzodiazole (130 mg, 0.299 mmol) was dissolved in N,N-dimethylformamide (2 mL) with stirring under nitrogen at room temperature and copper (I) cyanide (32 mg, 0.359 mmol) added. The reaction mixture was heated to 120° C. for 4 hours then cooled to room temperature. To the reaction mixture was added water (5 mL), ethyl acetate (5 mL) and tert-butyl methyl ether (5 mL) and the layers separated. The organic layer was washed with water (2×10 mL) and brine (2×10 mL), dried over magnesium sulphate, filtered and concentrated. Purification by FCC (silica, 0-66% ethyl acetate in heptane) gave the title compound 71 mg (62% yield) as a pale yellow solid. Tr(METCR1278)=2.19 min, (ES$^+$) (M+H)$^+$ 381.

Step 6, Method 4: 4-(6-Methoxy-1H-1,3-benzodiazol-2-yl)pyridine-3-carboxamide 4-(6-Methoxy-1-{[2-(trimethylsilyl)ethoxy]methyl}-1H-1,3-benzodiazol-2-yl)pyridine-3-carbonitrile (71 mg, 0.19 mmol) was dissolved in 2 M hydrochloric acid in diethyl ether (2 mL) and stirred at room temperature. After 5 hours the reaction mixture was concentrated and purified by preparative HPLC (acetonitrile-water) to give the title compound 5.6 mg (11% yield) as a yellow solid.

Example 1, Method 4 4-(6-Methoxy-1H-1,3-benzodiazol-2-yl)pyridine-3-carbonitrile δ$_H$ NMR (500 MHz, DMSO) 13.33 (s, 1H), 9.13 (s, 1H), 8.99 (d, J=5.2 Hz, 1H), 8.09 (d, J=5.3 Hz, 1H), 7.59 (m, 1H), 7.14 (m, 1H), 6.95 (d, J=8.3 Hz, 1H), 3.84 (s, 3H). Tr(MET-uHPLC-AB-101)=1.93 min, (ES$^+$) (M+H)$^+$ 251.

The following example was prepared using Method 4 described above:

temperature. Ethyl acetate (10 mL) and water (10 mL) were added and the layers separated. The organic layer was washed with water (2×10 mL) and brine (2×10 mL), dried over magnesium sulphate, filtered and concentrated under reduced pressure to give a tan powder which was slurried in hot methanol (20 mL) and allowed to stand at room temperature for 2 hours. The mixture was filtered and the solid collected and dried under suction to give the title compound

TABLE 5

| Example | Structure | Mol. Weight | IUPAC Name | LCMS data |
| --- | --- | --- | --- | --- |
| 1 | 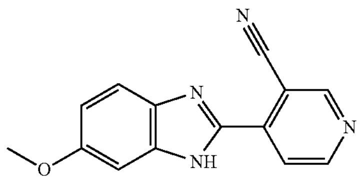 [SMILES: COc1ccc2nc(-c3ccncc3C#N)[nH]c2c1] | 250.26 | 4-(6-Methoxy-1H-1,3-benzodiazol-2-yl)pyridine-3-carbonitrile | Tr(MET-uHPLC-AB-101) = 1.93 min, (ES$^+$) (M + H)$^+$ 251 |

Method 5

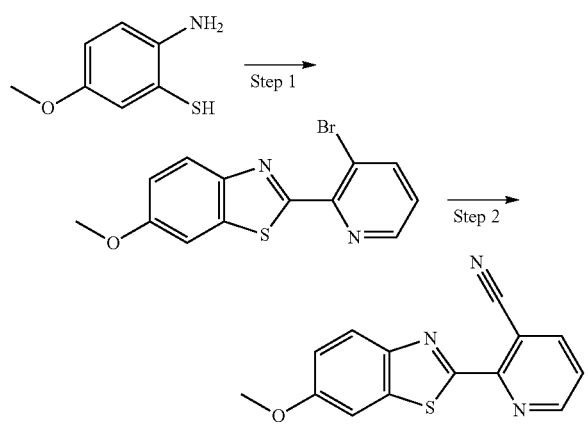

Scheme for Method 5

Step 1, Method 5: 2-(3-Bromopyridin-2-yl)-6-methoxy-1,3-benzothiazole

To a stirred solution of 2-amino-5-methoxybenzene-1-thiol (300 mg, 1.93 mmol) and 3-bromopyridine-2-carbaldehyde (360 mg, 1.93 mmol) in N,N-dimethylformamide (3 mL) under nitrogen was added sodium metabisulfite (367 mg, 1.93 mmol). The reaction mixture was heated to 130° C. and stirred for 4.5 hours, then allowed to cool to room 180 mg (29% yield) as a tan powder. Tr(MET-uHPLC-AB-101)=3.81 min, (ES$^+$) (M+H)$^+$ 321/323.

Step 2, Method 5: 2-(6-Methoxy-1,3-benzothiazol-2-yl)pyridine-3-carbonitrile 2-(3-Bromopyridin-2-yl)-6-methoxy-1,3-benzothiazole (120 mg, 0.374 mmol) was dissolved in N,N-dimethylformamide (2 mL) with stirring under nitrogen at room temperature and copper(I) cyanide (44 mg, 0.486 mmol) added. The reaction mixture was heated to 120° C. for 4.5 hours, then allowed to cool to room temperature. Water (5 mL), ethyl acetate (5 mL) and tert-butyl methyl ether (5 mL) were added and the layers separated. The organic layer was washed with water (2×10 mL) and brine (2×10 mL), dried over magnesium sulphate, filtered and concentrated to give a solid which was slurried in hot methanol (10 mL) to give the title compound 36 mg (36% yield) as a tan powder.

Example 1, Method 5: 2-(6-Methoxy-1,3-benzothiazol-2-yl)pyridine-3-carbonitrile δ$_H$ NMR (500 MHz, DMSO) 8.96 (dd, J=4.8, 1.5 Hz, 1H), 8.51 (dd, J=7.9, 1.4 Hz, 1H), 8.02 (d, J=9.0 Hz, 1H), 7.79 (d, J=2.5 Hz, 1H), 7.74 (dd, J=7.9, 4.8 Hz, 1H), 7.21 (dd, J=9.0, 2.6 Hz, 1H), 3.88 (s, 3H). Tr(MET-uHPLC-AB-101)=3.32 min, (ES$^+$) (M+H)$^+$ 268.

The following examples were prepared using Method 5 described above:

TABLE 6

| Example | Structure | Mol. Weight | IUPAC Name | LCMS data |
| --- | --- | --- | --- | --- |
| 1 | 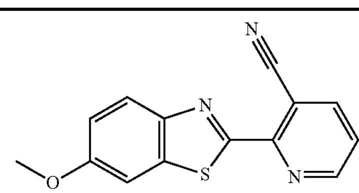 | 267.31 | 2-(6-Methoxy-1,3-benzothiazol-2-yl)pyridine-3-carbonitrile | Tr(MET-uHPLC-AB-101) = 3.32 min, (ES$^+$) (M + H)$^+$ 268 |

TABLE 6-continued

| Example | Structure | Mol. Weight | IUPAC Name | LCMS data |
|---|---|---|---|---|
| 2 | 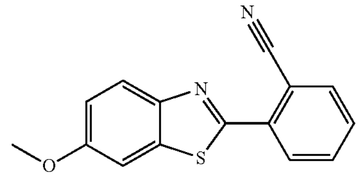 | 266.32 | 2-(6-Methoxy-1,3-benzothiazol-2-yl)benzonitrile | Tr(MET-uHPLC-AB-101) = 3.52 min, (ES$^+$) (M + H)$^+$ 267 |
| 3 | 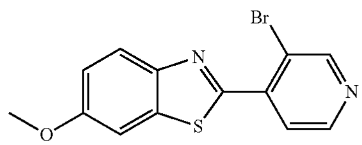 [SMILES: COc1ccc2nc(-c3ccncc3Br)sc2c1] | 321.19 | 2-(3-Bromopyridin-4-yl)-6-methoxy-1,3-benzothiazole | Tr(MET-uHPLC-AB-101) = 3.57 min, (ES$^+$) (M + H)$^+$ 321/323 |
| 4 | 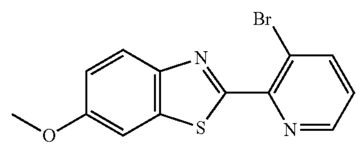 [SMILES: COc1ccc2nc(-c3ncccc3Br)sc2c1] | 321.19 | 2-(3-Bromopyridin-2-yl)-6-methoxy-1,3-benzothiazole | Tr(MET-uHPLC-AB-101) = 3.81 min, (ES$^+$) (M + H)$^+$ 321/323 |
| 5 | 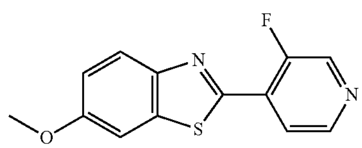 [SMILES: COc1ccc2nc(-c3ccncc3F)sc2c1] | 260.29 | 2-(3-Fluoropyridin-4-yl)-6-methoxy-1,3-benzothiazole | Tr(MET-uHPLC-AB-101) = 3.27 min, (ES$^+$) (M + H)$^+$ 261 |
| 6 | 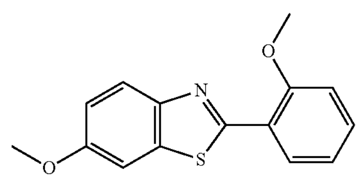 [SMILES: COc1ccc2nc(-c3ccccc3OC)sc2c1] | 271.33 | 6-Methoxy-2-(2-methoxyphenyl)-1,3-benzothiazole | Tr(MET-uHPLC-AB-101) = 3.89 min, (ES$^+$) (M + H)$^+$ 272 |
| 7 | 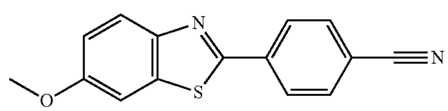 [SMILES: COc1ccc2nc(-c3ccc(C#N)cc3)sc2c1] | 266.32 | 4-(6-Methoxy-1,3-benzothiazol-2-yl)benzonitrile | Tr(MET-uHPLC-AB-101) = 3.74 min, (ES$^+$) (M + H)$^+$ 267 |

Method 6

Scheme for Method 6

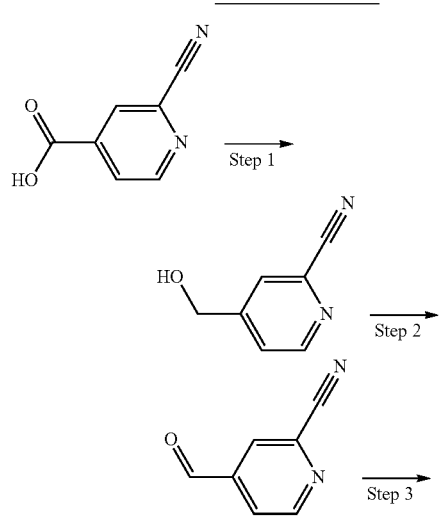

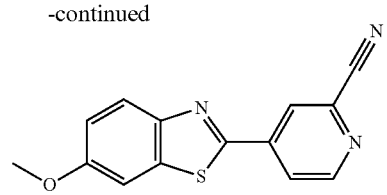

Step 1, Method 6:
4-(Hydroxymethyl)pyridine-2-carbonitrile

2-Cyanoisonicotinic acid (300 mg, 2.03 mmol) was dissolved in dichloromethane (3 mL) with stirring at room temperature under nitrogen and cooled to 0° C. Oxalyl chloride (0.521 mL, 6.08 mmol) was added followed by N,N-dimethylformamide (1 drop). The reaction mixture was then stirred at 0-5° C. for 1.5 hours. The mixture was concentrated and the resulting residue dissolved in tetrahydrofuran (3 mL). After cooling to 0° C., methanol (1.5 mL) was added and the reaction mixture stirred for 10 minutes. Lithium borohydride (76 mg, 2.03 mmol) was added and after 1.5 hours the reaction mixture was concentrated and the residue dissolved in ethyl acetate (10 mL). The solution was washed with 0.5 M hydrochloric acid (10 mL), water (10 mL) and brine (10 mL), dried over magnesium sulphate, filtered and concentrated. Purification by FCC (silica, 0-80% ethyl acetate in heptane) gave the title compound 123 mg (43% yield) as a colourless solid. Tr(METCR1278)=0.63 min, (ES$^+$) (M+H)$^+$ 135.

Step 2, Method 6: 4-Formylpyridine-2-carbonitrile 4-(Hydroxymethyl)pyridine-2-carbonitrile (120 mg, 0.895 mmol) was dissolved in dichloromethane (3 mL) with stirring at room temperature. 1,1,1-Triacetoxy-1,1-dihydro-1,2-benziodoxol-3(1H)-one (417 mg, 0.984 mmol) was added and the reaction mixture stirred at room temperature for 4 hours. Dichloromethane (5 mL) and saturated aqueous sodium bicarbonate (8 mL) were added and the layers separated. The organic layer was washed with water (8 mL) and brine (8 mL), dried over magnesium sulphate, filtered and concentrated to give the title compound 123 mg (60% purity, 60% yield) as a pale yellow solid which was used in the next step without further purification.

Step 3, Method 6: 4-(6-Methoxy-1,3-benzothiazol-2-yl)pyridine-2-carbonitrile

To a stirred solution of 2-amino-5-methoxybenzene-1-thiol (85 mg, 0.548 mmol) and 2-cyanopyridine-4-carbaldehyde (120 mg, 60% purity, 0.548 mmol) in N,N-dimethylformamide (3 mL) under nitrogen was added sodium metabisulfite (104 mg, 0.548 mmol). The reaction mixture was heated to 130° C. and stirred for 4 hours, then allowed to cool to room temperature. Ethyl acetate (10 mL) and water (10 mL) were added and the layers separated. The organic layer was washed with water (2×10 mL) and brine (2×10 mL), dried over magnesium sulphate, filtered and concentrated. The residue was slurried in hot methanol (2×7 mL) and allowed to stand at room temperature for 2 hours. The mixture was filtered and the solid dried under suction to give the title compound 18 mg (12% yield) as a beige powder.

Example 1, Method 6: 4-(6-Methoxy-1,3-benzothiazol-2-yl)pyridine-2-carbonitrile $\delta_H$ NMR (500 MHz, DMSO) 8.91 (d, J=5.1 Hz, 1H), 8.60 (s, 1H), 8.31 (dd, J=5.1, 1.6 Hz, 1H), 8.06 (d, J=9.0 Hz, 1H), 7.85 (d, J=2.4 Hz, 1H), 7.23 (dd, J=9.0, 2.5 Hz, 1H), 3.88 (s, 3H). Tr(MET-uHPLC-AB-101)=3.39 min, (ES$^+$) (M+H)$^+$ 268.

The following example was prepared using Method 6 described above:

Method 7

Scheme for Method 7

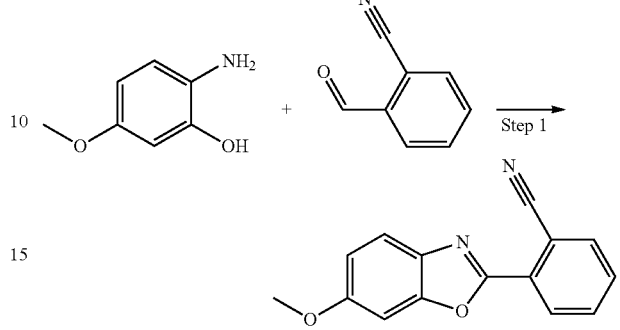

Step 1, Method 7:
2-(6-Methoxy-1,3-benzoxazol-2-yl)benzonitrile

2-Amino-5-methoxyphenol hydrochloride (100 mg, 1.14 mmol) was dissolved in water (10 mL), the pH adjusted to 8 with sodium carbonate and the mixture extracted with ethyl acetate (3×5 mL). The organic layer was evaporated and dissolved in ethyl acetate (5 mL). Molecular sieves (150 mg) and 2-formylbenzonitrile (78 mg, 0.6 mmol) were added. The mixture was heated to 80° C. under an atmosphere of nitrogen gas for 1.25 hours. The temperature of the reaction was lowered to 45° C. and the reaction stirred for 21 hours. 1-Hydroxy-1,2-benziodoxol-3(1H)-one 1-oxide (319 mg, 1.14 mmol) was added followed by molecular sieves (150 mg) and the reaction mixture stirred at 80° C. for 4 hours. The cooled reaction mixture was filtered through 'Kieselghur' and washed with ethyl acetate (4×5 mL) and acetonitile (3×5 mL). The combined organic layers were concentrated. Purification by FCC (silica, 0-50% ethyl acetate in heptane), recrystallisation from methanol (5 mL) and drying in a vacuum oven at 40° C. gave the title compound 37 mg (16% yield) as red crystals.

Example 1, Method 7:
2-(6-Methoxy-1,3-benzoxazol-2-yl)benzonitrile $\delta_H$ NMR (500 MHz, DMSO) 8.31 (d, J=7.9 Hz, 1H), 8.08 (d, J=7.7 Hz, 1H), 7.93 (td, J=7.9, 1.1 Hz, 1H), 7.80-7.75 (m, 2H), 7.45 (d, J=2.3 Hz, 1H), 7.06 (dd, J=8.8, 2.4 Hz, 1H), 3.87 (s, 3H). Tr(MET-uHPLC-AB-101)=3.32 min, (ES$^+$) (M+H)$^+$ 251.

The following example was prepared using Method 7 described above:

TABLE 7

| Example | Structure | Mol. Weight | IUPAC Name | LCMS data |
| --- | --- | --- | --- | --- |
| 1 | 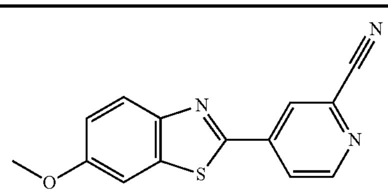 | 267.31 | 4-(6-Methoxy-1,3-benzothiazol-2-yl)pyridine-2-carbonitrile | Tr(MET-uHPLC-AB-101) = 3.39 min, (ES$^+$) (M + H)$^+$ 268 |

TABLE 8

| Example | Structure | Mol. Weight | IUPAC Name | LCMS data |
|---------|-----------|-------------|------------|-----------|
| 1 | 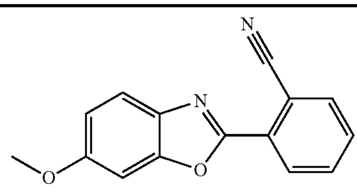 | 250.25 | 2-(6-Methoxy-1,3-benzoxazol-2-yl)benzonitrile | Tr(MET-uHPLC-AB-101) = 3.32 min, (ES+) (M + H)+ 251 |

Method 8

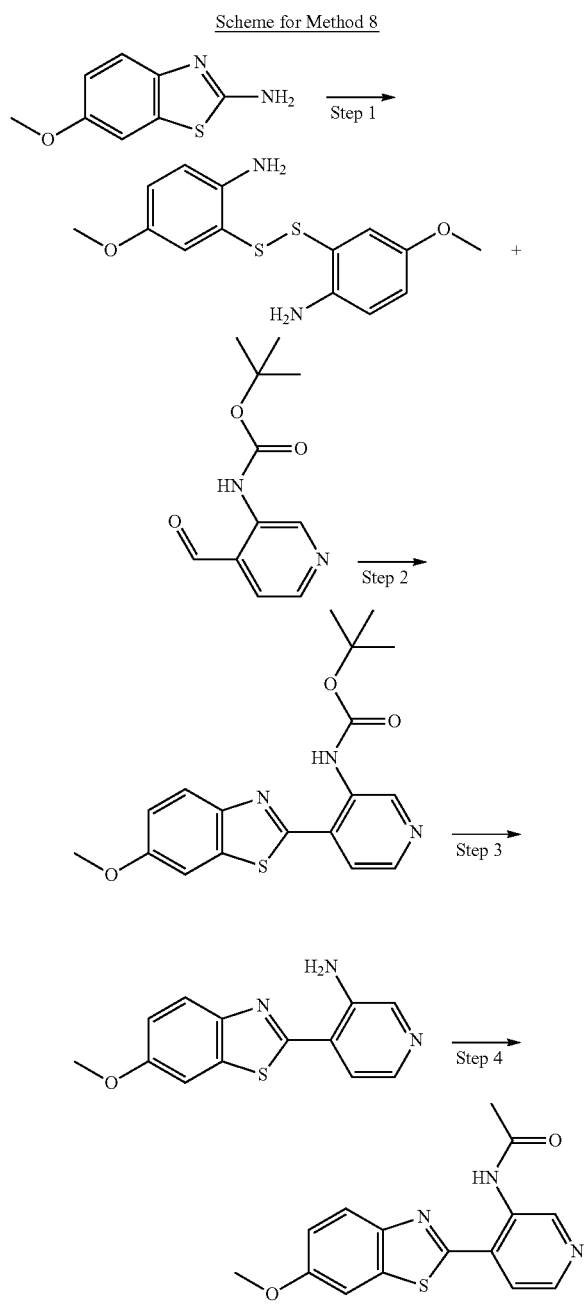

Scheme for Method 8

Step 1, Method 8: 2-[(2-Amino-5-methoxyphenyl)disulfonyl]-4-methoxyaniline

2-Amino-6-methoxybenzothiazole (15 g, 0.083 mol) was suspended in 9.24 M aqueous potassium hydroxide (90 mL) with stirring and ethylene glycol (90 mL) was added. The stirred suspension was heated to 100° C. and stirred for 72 hours. The reaction mixture was cooled to room temperature and toluene (90 mL) added. The mixture was cooled using an ice-water bath and with stirring the mixture was acidified to pH 5 using acetic acid and the layers separated. The aqueous layer was extracted with toluene (2×90 mL). The organic extracts were combined and washed with water (120 mL) and brine (120 mL), dried over magnesium sulphate, filtered and concentrated to give the title compound 7.70 g (28% yield) as a yellow powder. Tr(METCR1278)=1.80 min, (ES+) (M+H)+ 309.

Step 2, Method 8: tert-Butyl N-[4-(6-Methoxy-1,3-benzothiazol-2-yl)pyridin-3-yl]carbamate To a stirred solution of 2-[(2-amino-5-methoxyphenyl)disulfonyl]-4-methoxyaniline (100 mg, 0.324 mmol) and tert-butyl(4-formylpyridine-3-yl)carbamate (144 mg, 0.648 mmol) in N,N-dimethylformamide (3 mL) under nitrogen was added sodium metabisulfite (123 mg, 0.648 mmol). The reaction mixture was heated to 130° C. and stirred for 1.5 hours. The mixture was allowed to cool to room temperature then ethyl acetate (10 mL) and water (10 mL) added and the layers separated. The organic layer was washed with water (2×10 mL) and brine (2×10 mL). The combined organic layers were dried over magnesium sulphate, concentrated, recrystallised twice from methanol (8 mL) and the resulting solid dried under suction to give the title compound 50 mg (21% yield) as an off-white powder. $\delta_H$ NMR (500 MHz, DMSO) 10.76 (s, 1H), 9.32 (s, 1H), 8.43 (d, J=5.1 Hz, 1H), 7.98 (d, J=9.0 Hz, 1H), 7.89 (d, J=5.1 Hz, 1H), 7.82 (d, J=2.5 Hz, 1H), 7.22 (dd, J=9.0, 2.5 Hz, 1H), 3.88 (s, 3H), 1.49 (s, 9H). Tr(MET-uHPLC-AB-101)=4.1 min, (ES+) (M+H)+ 358.

Step 3, Method 8:
4-(6-Methoxy-1,3-benzothiazol-2-yl)pyridin-3-amine dihydrochloride tert-Butyl N-[4-(6-methoxy-1,3-benzothiazol-2-yl)pyridin-3-yl]carbamate (25 mL) was added to a stirred solution of 2 M hydrochloric acid in diethyl ether (4 mL). Methanol (1 mL) was added and the reaction mixture stirred at room temperature for 48 hours. The solution was concentrated to give the title compound 21 mg (100% yield) as an orange powder. $\delta_H$ NMR (250 MHz, deuterium oxide) 7.47 (s, 1H), 7.34-7.13 (m, 3H), 6.83 (s, 1H), 6.56 (d, J=7.8 Hz, 1H), 3.51 (s, 3H). Tr(MET-uHPLC-AB-101)=1.84 min, (ES⁺) (M+H)⁺ 258.

Step 4, Method 8: N-[4-(6-Methoxy-1,3-benzothiazol-2-yl)pyridin-3-yl]acetamide

To a stirred solution of 4-(6-methoxy-1,3-benzothiazol-2-yl)pyridin-3-amine dihydrochloride (50 mg, 0.151 mmol) in dichloromethane (3 mL) under nitrogen was added acetic anhydride (16 µL, 0.167 mmol) and pyridine (38 µL, 0.469 mmol). The reaction mixture was stirred at room temperature for 72 hours. Dichloromethane (5 mL) and water (5 mL) were added and the layers separated. The organic layer was washed with water (2×5 mL), brine (2×5 mL), dried over magnesium sulphate, filtered and concentrated. Purification by FCC (silica 0-50% ethyl acetate in heptane) gave the title compound 12 mg (26% yield) as a yellow powder.

Example 1 Method 8: N-[4-(6-Methoxy-1,3-benzothiazol-2-yl)pyridin-3-yl]acetamide $\delta_H$ NMR (500 MHz, DMSO) 11.45 (s, 1H), 9.47 (s, 1H), 8.57 (d, J=4.6 Hz, 1H), 8.13 (m, 2H), 7.84 (d, J=2.2 Hz, 1H), 7.25 (dd, J=9.0, 2.3 Hz, 1H), 3.89 (s, 3H), 2.27 (s, 3H). Tr(MET-uHPLC-AB-101)=2.67 min, (ES⁺) (M+H)⁺ 300.

The following example was prepared using Method 8 described above:

TABLE 9

| Example | Structure | Mol. Weight | IUPAC Name | LCMS data |
|---|---|---|---|---|
| 1 | 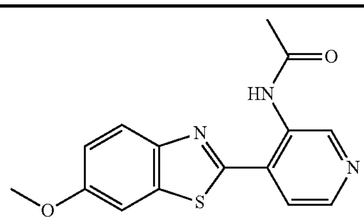 | 299.35 | N-[4-(6-Methoxy-1,3-benzothiazol-2-yl)pyridin-3-yl]acetamide | Tr(MET-uHPLC-AB-101) = 2.67 min, (ES⁺) (M + H)⁺ 300 |

Method 9

Scheme for Method 9

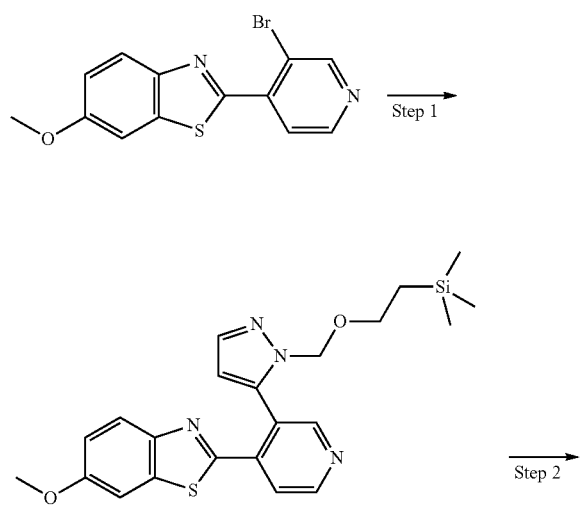

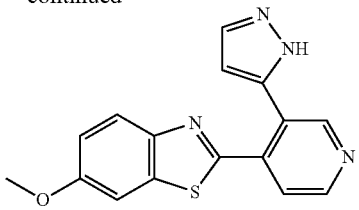

Step 1, Method 9: 6-Methoxy-2-[3-(1-{[2-(trimethylsilyl)ethoxy]methyl}-H-pyrazol-5-yl)pyridin-4-yl]-1,3-benzothiazole 2-(3-Bromopyridin-4-yl)-6-methoxy-1,3-benzothiazole (100 mg, 0.31 mmol, prepared by Method 5), 5-(tetramethyl-1,3,2-dioxaborolan-2-yl)-1-{[2-(trimethylsilyl)ethoxy]methyl}-1H-pyrazole (111 mg, 0.34 mmol), tetrakis(triphenylphosphine)palladium(0) (18 mg, 0.02 mmol) and sodium hydrogen carbonate in a mixture of 1,4-dioxane (3 mL) and water (2 mL) were stirred at 105° C. for 18 hours. 5-(Tetramethyl-1,3,2-dioxaborolan-2-yl)-1-{[2-(trimethylsilyl)ethoxy]methyl}-1H-pyrazole (101 mg, 0.31 mmol) was added and the mixture stirred at reflux for 1 hour. The reaction was cooled to room temperature and water (10 mL) added. The mixture was extracted with ethyl acetate (3×10 mL), the combined organic layers dried over sodium sulphate, filtered and concentrated. Purification by FCC (silica, 0% to 50% ethyl acetate in heptane) gave the title compound 70 mg (51% yield) as a yellow oil. $\delta_H$ NMR (500 MHz, DMSO) 8.85 (d, J=5.2 Hz, 1H), 8.64 (s, 1H), 8.24 (d, J=5.2 Hz, 1H), 7.97 (d, J=9.0 Hz, 1H), 7.75 (d, J=1.7 Hz, 1H), 7.65 (d, J=2.5 Hz, 1H), 7.14 (dd, J=9.0, 2.5 Hz, 1H), 6.68 (d, J=1.7 Hz, 1H), 5.10 (s, 2H), 3.80 (s, 3H), 3.31-3.22 (m, 2H), 0.37-0.22 (m, 2H), −0.21 (s, 9H). Tr (METCR1278)=2.45 min, (ES⁺) (M+H)⁺ 439.

Step 2, Method 9: 6-Methoxy-2-[3-(1H-pyrazol-5-yl)pyridin-4-yl]-1,3-benzothiazole 6-Methoxy-2-[3-(1-{[2-(trimethylsilyl)ethoxy]methyl}-1H-pyrazol-5-yl)pyridin-4-yl]-1,3-benzothiazole (50 mg, 0.11 mmol) was treated with 2 M hydrogen chloride in diethyl ether (1.1 mL). The mixture was stirred at room temperature for 20 hours and purified by SCX. Purification by FCC (silica, 0 to 10% methanol in dichloromethane) and trituration with diethyl ether gave the title compound 32 mg (91% yield) as a white solid.

Example 1, Method 9: 6-Methoxy-2-[3-(1H-pyrazol-5-yl)pyridin-4-yl]-1,3-benzothiazole δ$_H$ NMR (500 MHz, DMSO) 13.18 (s, 1H), 8.80 (s, 1H), 8.73 (d, J=3.9 Hz, 1H), 8.15-7.74 (m, 2H), 7.65 (d, J=2.3 Hz, 1H), 7.14 (dd, J=9.0, 2.5 Hz, 1H), 6.35 (s, 1H), 3.82 (s, 3H). Tr(MET-uHPLC-AB-101)=2.32 min, (ES$^+$) (M+H)$^+$ 309.

The following example was prepared using Method 9 described above:

TABLE 10

| Example | Structure | Mol. Weight | IUPAC Name | LCMS data |
|---|---|---|---|---|
| 1 | 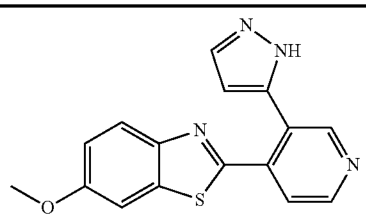 | 308.36 | 6-Methoxy-2-[3-(1H-pyrazol-5-yl)pyridin-4-yl]-1,3-benzothiazole | Tr(MET-uHPLC-AB-101) = 2.32 min, (ES$^+$) (M + H)$^+$ 309 |

Method 10

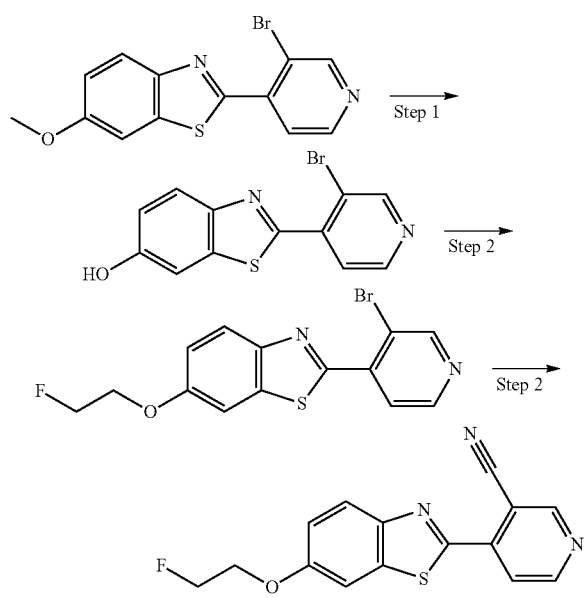

Scheme for Method 10

Step 1, Method 10: 2-(3-Bromopyridin-4-yl)-1,3-benzothiazol-6-ol

To a suspension of 2-(3-bromopyridin-4-yl)-6-methoxy-1,3-benzothiazole (200 mg, 0.62 mmol, prepared by Method 5) in dichloromethane (6 mL) was added boron tribromide (1 M in dichloromethane, 2.80 mL, 2.80 mmol) and the mixture stirred at room temperature for 24 hours. The reaction was quenched with water (10 mL), neutralized with solid sodium hydrogen carbonate (6 mmol) and extracted with a dichloromethane:ethanol (4:1) solution (3×20 mL). The organic layers were combined, washed with water (20 mL), dried over sodium sulphate, filtered and concentrated. The residue was purified by FCC (silica, 0-100% ethyl acetate in toluene, then 5-20% ethyl acetate in methanol, then 0-30% dichloromethane in methanol, then acetonitrile). The silica of the column was washed with a dichloromethane:isopropanol (4:1) solution (3×100 mL). The suspension was filtered. The filtrate was combined with the fractions containing the title compound and concentrated. The residue was dissolved in hot methanol and filtered. The filtrate was allowed to stand at room temperature for 18 hours then filtered. 50 mg were sonicated in a 2 M aqueous sodium hydroxide (5 mL). The mixture was washed with ethyl acetate (5 mL). The aqueous phase was treated with a 2 M hydrochloric solution up to pH 7 and extracted with ethyl acetate (3×10 mL). The organic layers were combined, dried over sodium sulphate, filtered and concentrated. The residue was triturated in hot ethyl acetate and filtered to give the title compound 5.4 mg (3% yield) as an off white solid. δ$_H$ NMR (500 MHz, DMSO) 8.97 (s, 1H), 8.69 (d, J=5.0 Hz, 1H), 8.11 (d, J=5.0 Hz, 1H), 7.98 (d, J=8.8 Hz, 1H), 7.50 (d, J=2.2 Hz, 1H), 7.08 (dd, J=8.9, 2.3 Hz, 1H). Tr(MET-uHPLC-AB-101)=2.67 min, (ES$^+$) (M+H)$^+$ 307/309.

Step 2, Method 10: 2-(3-Bromopyridin-4-yl)-6-(2-fluoroethoxy)-1,3-benzothiazole 2-(3-Bromopyridin-4-yl)-1,3-benzothiazol-6-ol (150 mg, 0.49 mmol), 1-bromo-2-fluoroethane (40 µL, 0.54 mmol) and potassium carbonate (236 mg, 1.71 mmol) in N,N-dimethylformamide (1 mL) were stirred at 60° C. for 19 hours. 1-Bromo-2-fluoroethane (40 µL, 0.54 mmol) was added and the mixture stirred at 80° C. for 5 hours. The mixture was stirred at room temperature for 2 days, then treated with water (10 mL) and extracted with ethyl acetate (3×10 mL). The organic layers were combined, dried over sodium sulphate, filtered and concentrated. Purification by FCC (silica, 0-40% ethyl acetate in heptane) gave the title compound 73 mg (42% yield) as a white solid. δ$_H$ NMR (500 MHz, DMSO) 8.99 (s, 1H), 8.72 (d, J=5.1 Hz, 1H), 8.13 (d, J=5.1 Hz, 1H), 8.09 (d, J=9.0 Hz, 1H), 7.86 (d, J=2.5 Hz, 1H), 7.28 (dd, J=9.0, 2.5 Hz, 1H), 4.92-4.66 (m, 2H), 4.47-4.25 (m, 2H). Tr(MET-uHPLC-AB-101)=3.48 min, (ES$^+$) (M+H)$^+$ 353/355.

Step 3, Method 10: 4-[6-(2-Fluoroethoxy)-1,3-benzothiazol-2-yl]pyridine-3-carbonitrile)

To 2-(3-bromopyridin-4-yl)-6-(2-fluoroethoxy)-1,3-benzothiazole (50 mg, 0.14 mmol) in N,N-dimethylformamide (1 mL), was added copper(I) cyanide (15 mg, 0.17 mmol). The mixture was stirred at 130° C. for 3 hours then cooled to room temperature. A diluted ammonia solution (25 mL) was added and the mixture extracted with ethyl acetate (2×10 mL). The organic layers were combined, dried over sodium sulphate, filtered and concentrated. The residue was purified by FCC (silica, 0-50% ethyl acetate in heptane) to give the title compound 37 mg (87% yield) as a white solid.

Example 1, Method 10: 4-[6-(2-Fluoroethoxy)-1,3-benzothiazol-2-yl]pyridine-3-carbonitrile)

$\delta_H$ NMR (250 MHz, DMSO) 9.27 (s, 1H), 9.06 (d, J=5.3 Hz, 1H), 8.29-8.10 (m, 2H), 7.98 (d, J=2.5 Hz, 1H), 7.36 (dd, J=9.0, 2.6 Hz, 1H), 5.03-4.73 (m, 2H), 4.55-4.32 (m, 2H). Tr(MET-uHPLC-AB-101)=3.02 min, (ES$^+$) (M+H)$^+$ 300.

The following examples were prepared using Method 10 described above:

Step 1, Method 11: tert-Butyl N-[4-(6-methoxy-1,3-benzothiazol-2-yl)pyridin-3-yl]-N-methylcarbamate tert-Butyl N-[4-(6-methoxy-1,3-benzothiazol-2-yl)pyridin-3-yl]carbamate (25 mg, 0.07 mmol, prepared by Method 5) was dissolved with stirring in N,N-dimethylformamide (3 mL) under nitrogen and cooled to 0° C. Sodium hydride (60% in mineral oil, 3 mg, 0.077 mmol) was added and the reaction mixture stirred at 0-5° C. for 15 minutes. Iodomethane (5 μL, 0.077 mmol) was added and the reaction mixture stirred at 0-20° C. for 4 hours. Ethyl acetate (10 mL) and water (10 mL) were added and the organic phase separated, washed with water (2×10 mL) and brine (2×10 mL). The combined organic extracts were dried over magnesium

TABLE 11

| Example | Structure | Mol. Weight | IUPAC Name | LCMS data |
|---|---|---|---|---|
| 1 | 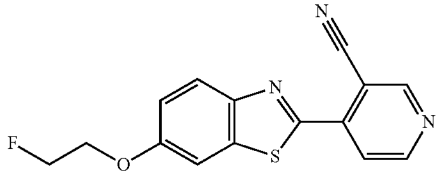 [SMILES: N#Cc1cnccc1-c1nc2ccc(OCCF)cc2s1] | 299.32 | 4-[6-(2-Fluoroethoxy)-1,3-benzothiazol-2-yl]pyridine-3-carbonitrile | Tr(MET-uHPLC-AB-101) = 3.02 min, (ES$^+$) (M + H)$^+$ 300 |
| 2 | 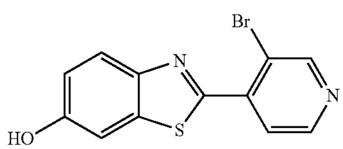 [SMILES: Oc1ccc2nc(-c3ccncc3Br)sc2c1] | 307.17 | 2-(3-Bromopyridin-4-yl)-1,3-benzothiazol-6-ol | Tr(MET-uHPLC-AB-101) = 2.67 min, (ES$^+$) (M + H)$^+$ 307/309 |
| 3 | 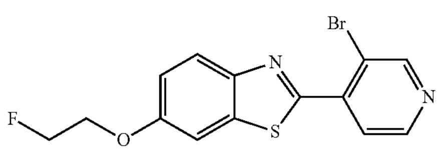 [SMILES: FCCOc1ccc2nc(-c3ccncc3Br)sc2c1] | 353.21 | 2-(3-Bromopyridin-4-yl)-6-(2-fluoroethoxy)-1,3-benzothiazole | Tr(MET-uHPLC-AB-101) = 3.48 min, (ES$^+$) (M + H)$^+$ 353/355 |

Method 11

Scheme for Method 11

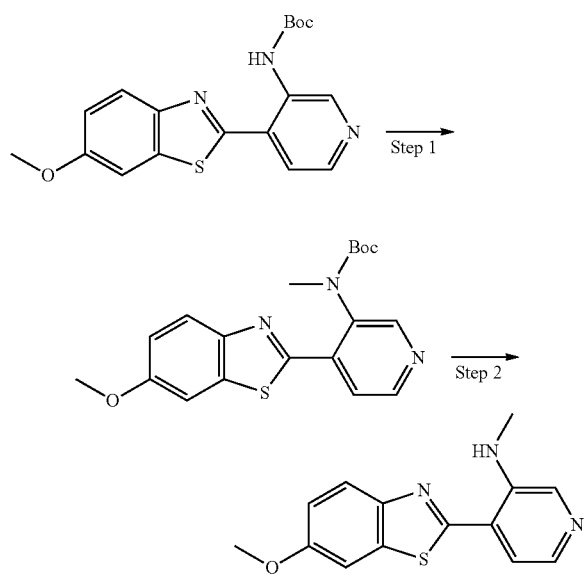

sulphate, filtered and concentrated. Purification by FCC (silica, 12-100% ethyl acetate in heptane) gave the title compound 13 mg (49% yield) as a colourless oil. Tr(METCR1278)=2.09 min, (ES$^+$) (M+H)$^+$ 372.

Step 2, Method 11: 4-(6-Methoxy-1,3-benzothiazol-2-yl)-N-methylpyridin-3-amine

Trifluoroacetic acid (1 mL) was added to a solution of tert-butyl N-[4-(6-methoxy-1,3-benzothiazol-2-yl)pyridin-3-yl]-N-methylcarbamate (13 mg, 0.03 mmol) in dichloromethane (4 mL) and the mixture stirred at room temperature for 2 hours. The mixture was concentrated, water (4 mL) and saturated aqueous sodium carbonate (2 mL) added and the mixture extracted with dichloromethane (3×3 mL). The combined organic extracts were dried over sodium sulphate, filtered and concentrated to give the title compound 6 mg (63% yield) as a yellow powder.

Example 2, Method 11: 4-(6-Methoxy-1,3-benzothiazol-2-yl)-N-methylpyridin-3-amine $\delta_H$ NMR (500 MHz, chloroform) 8.44 (br. s, 1H), 8.30 (br. s, 1H), 8.00 (br. s, 1H), 7.91 (d, J=8.9 Hz, 1H), 7.47 (br. s, 1H), 7.35 (d, J=2.5 Hz, 1H), 7.10 (dd, J=8.9, 2.5 Hz, 1H), 3.90 (s, 3H), 3.12 (d, J=5.2 Hz, 3H). Tr(MET-uHPLC-AB-101)=1.96 min, (ES$^+$) (M+H)$^+$ 272.

The following example was prepared using Method 11 described above:

TABLE 12

| Example | Structure | Mol. Weight | IUPAC Name | LCMS data |
|---|---|---|---|---|
| 1 | 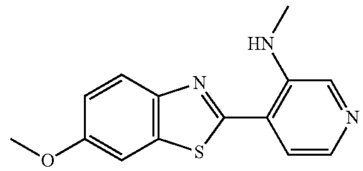 [SMILES: CNc1cnccc1-c1nc2ccc(OC)cc2s1] | 271.34 | 4-(6-Methoxy-1,3-benzothiazol-2-yl)-N-methylpyridin-3-amine | Tr(MET-uHPLC-AB-101) = 1.96 min, (ES$^+$) (M + H)$^+$ 272 |

Method 12

Scheme for Method 12

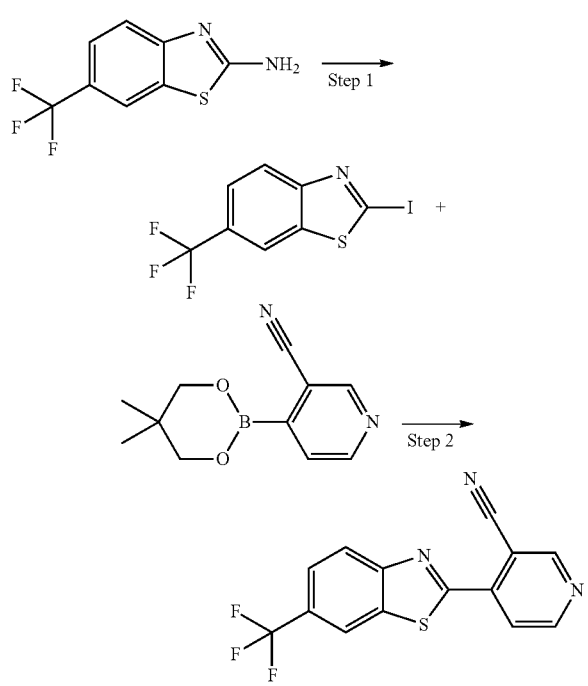

Step 1, Method 12: 2-Iodo-6-(trifluoromethyl)-1,3-benzothiazole

To a solution of 6-(trifluoromethyl)-1,3-benzothiazol-2-amine (200 mg, 0.92 mmol) in dry N,N-dimethylformamide (7 mL), diiodomethane (3.69 mL, 45.83 mmol) and 3-methylbutyl nitrite (3.69 mL, 27.5 mmol) were added and the mixture heated at 60° C. for 30 minutes. The volatile solvents were evaporated, water (20 mL) added and the mixture extracted with dichloromethane (2×10 mL). The combined organic layers were washed with water (5×10 mL), dried over sodium sulphate, filtered and concentrated. Purification by FCC (silica, 0-100% dichloromethane in heptane) gave the title compound 224 mg (74% yield) as a white powder. Tr(METCR1278)=2.24 min, (ES$^+$) (M+H)$^+$ 330.

Step 2, Method 12: 4-[6-(Trifluoromethyl)-1,3-benzothiazol-2-yl]pyridine-3-carbonitrile A sealed tube was charged with 4-(5,5-dimethyl-1,3,2-dioxaborinan-2-yl)pyridine-3-carbonitrile (54 mg, 0.25 mmol, prepared in Tetrahedron 61, (2005), 9955-9960), 2-iodo-6-(trifluoromethyl)-1,3-benzothiazole (100 mg, 0.3 mmol), caesium fluoride (77 mg, 0.51 mmol), copper(I) iodide (5 mg, 0.03 mmol) and 1,4-dioxane (4 mL) and the mixture degassed with nitrogen. Tetrakis(triphenylphosphine)palladium(0) (15 mg, 0.01 mmol) was added and the reaction stirred vigorously under nitrogen at 60° C. overnight. The reaction was quenched with water (4 mL) and extracted with ethyl acetate (3×5 mL). The combined organic extracts were dried over sodium sulphate, filtered and concentrated. Purification by FCC (silica, 4-40% ethyl acetate in heptane) gave the title compound 43 mg (56% yield) as a white powder.

Example 1, Method 12: 4-[6-(Trifluoromethyl)-1,3-benzothiazol-2-yl]pyridine-3-carbonitrile $\delta_H$ NMR (500 MHz, DMSO) 9.28 (s, 1H), 9.07 (d, J=5.2 Hz, 1H), 8.89 (s, 1H), 8.40 (d, J=8.6 Hz, 1H), 8.26 (d, J=5.2 Hz, 1H), 7.97 (dd, J=8.7, 1.7 Hz, 1H). Tr(MET-uHPLC-AB-101)=3.52 min, (ES$^+$) (M+H)$^+$ 306.

The following examples were prepared using Method 12 described above:

TABLE 13

| Example | Structure | Mol. Weight | IUPAC Name | LCMS data |
|---|---|---|---|---|
| 1 | 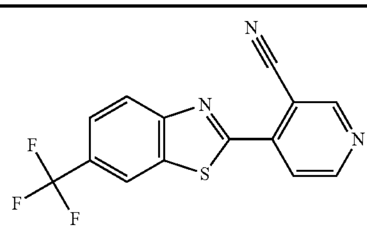 | 305.28 | 4-[6-(Trifluoromethyl)-1,3-benzothiazol-2-yl]pyridine-3-carbonitrile | Tr(MET-uHPLC-AB-101) = 3.52 min, (ES$^+$) (M + H)$^+$ 306 |

TABLE 13-continued

| Example | Structure | Mol. Weight | IUPAC Name | LCMS data |
|---|---|---|---|---|
| 2 | 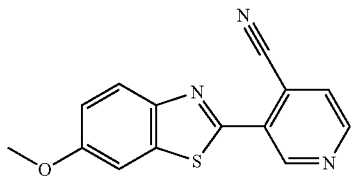 | 267.31 | 3-(6-Methoxy-1,3-benzothiazol-2-yl)pyridine-4-carbonitrile | Tr(MET-uHPLC-AB-101) = 3.02 min, (ES+) (M + H)+ 268 |

Method 13

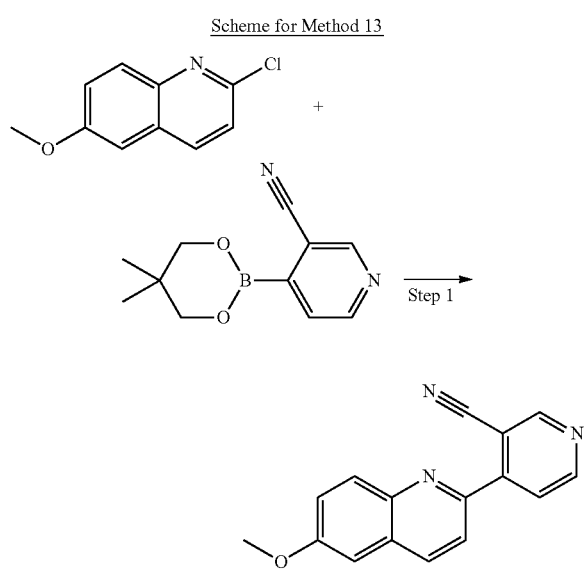

Scheme for Method 13

Step 1, Method 13:
4-(6-Methoxyquinolin-2-yl)pyridine-3-carbonitrile

A sealed tube was charged with 4-(5,5-dimethyl-1,3,2-dioxaborinan-2-yl)pyridine-3-carbonitrile (100 mg, 0.46 mmol, described in Tetrahedron 61, (2005), 9955-9960), 2-chloro-6-methoxyquinoline (108 mg, 0.56 mmol), copper (I) iodide (9 mg, 0.05 mmol), caesium fluoride (141 mg, 0.93 mmol) and 1,4-dioxane (6 mL) and the mixture degassed with nitrogen. Tetrakis(triphenylphosphine)palladium(0) (27 mg, 0.02 mmol) was added and the reaction stirred vigorously under nitrogen at 60° C. overnight. The reaction was quenched with water (6 mL) and extracted with ethyl acetate (3×8 mL). The organic phase was dried over sodium sulphate, filtered and concentrated. Purification by FCC (silica, 10-100% ethyl acetate in heptane), recrystallisation from ethyl acetate (15 mL), washing with diethyl ether (2×3 mL) and drying in a vacuum oven (40° C.) gave the title compound 51 mg (42% yield) as a white powder.

Example 1, Method 13:
4-(6-Methoxyquinolin-2-yl)pyridine-3-carbonitrile $\delta_H$ NMR (500 MHz, DMSO) 9.16 (s, 1H), 8.98 (d, J=5.2 Hz, 1H), 8.52 (d, J=8.6 Hz, 1H), 8.13 (d, J=5.2 Hz, 1H), 8.10 (d, J=8.6 Hz, 1H), 8.03 (d, J=9.0 Hz, 1H), 7.56-7.48 (m, 2H), 3.95 (s, 3H). Tr(MET-uHPLC-AB-101)=2.79 min, (ES+) (M+H)+ 262.

The following example was prepared using Method 13 described above:

TABLE 14

| Example | Structure | Mol. Weight | IUPAC Name | LCMS data |
|---|---|---|---|---|
| 1 | 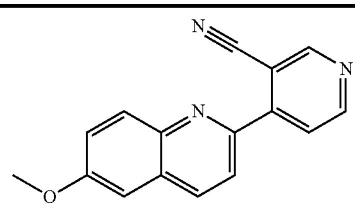 | 261.28 | 4-(6-Methoxyquinolin-2-yl)pyridine-3-carbonitrile | Tr(MET-uHPLC-AB-101) = 2.79 min, (ES+) (M + H)+ 262 |

Method 14

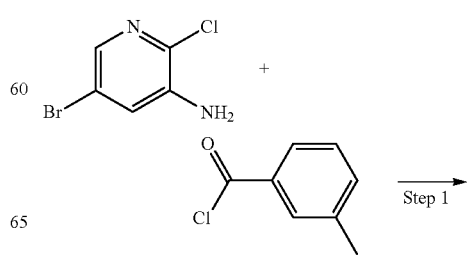

Scheme for Method 14

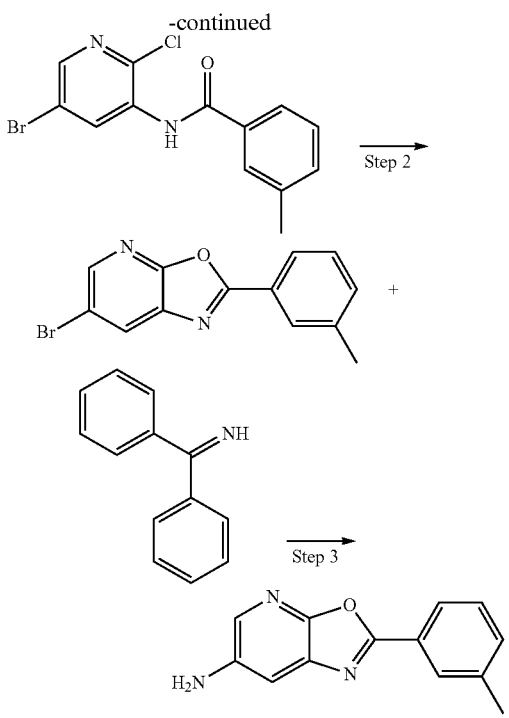

Step 1, Method 14: N-(5-Bromo-2-chloropyridin-3-yl)-3-methylbenzamide

To a stirred solution of 5-bromo-2-chloropyridin-3-amine (500 mg, 2.41 mmol) in pyridine (5 mL) at 0° C. was added 3-methylbenzoyl chloride (410 mg, 2.65 mmol) and the mixture stirred at room temperature for 1 hour. Water (50 mL) was added to the mixture. The precipitate was filtered and washed with water to give the title compound 653 mg (83% yield) as an off-white solid. $\delta_H$ NMR (250 MHz, DMSO) 10.28 (s, 1H), 8.49 (d, J=2.3 Hz, 1H), 8.39 (d, J=2.3 Hz, 1H), 7.85-7.70 (m, 2H), 7.45 (d, J=5.2 Hz, 2H), 2.41 (s, 3H). Tr (METCR1278)=2.25 min, (ES$^+$) (M+H)$^+$ 325/327.

Step 2, Method 14: 6-Bromo-2-(3-methylphenyl)-[1,3]oxazolo[5,4-b]pyridine

To a mixture of N-(5-bromo-2-chloropyridin-3-yl)-3-methylbenzamide (200 mg, 0.61 mmol), copper(I) iodide (6 mg, 0.03 mmol), N,N'-dimethylethane-1,2-diamine (7 μL, 0.06 mmol) and potassium carbonate (170 mg, 1.23 mmol) was added 1,4-dioxane (1 mL). The reaction was stirred at reflux for 24 hours. The mixture was added to diluted aqueous ammonia (100 mL). The aqueous layer was extracted with ethyl acetate (3×100 mL). The ethyl acetate layers were combined, dried over sodium sulphate and evaporated under reduced pressure to give the title compound 120 mg (67% yield) as a beige solid. $\delta_H$ NMR (500 MHz, DMSO) 8.59 (d, J=2.1 Hz, 1H), 8.51 (d, J=2.1 Hz, 1H), 8.07-7.99 (m, 2H), 7.53 (q, J=7.7 Hz, 2H), 2.45 (s, 3H). Tr(METCR1278)=2.58 min, (ES$^+$) (M+H)$^+$ 289/291.

Step 3, Method 14: 2-(3-Methylphenyl)-[1,3]oxazolo[5,4-b]pyridin-6-amine

6-Bromo-2-(3-methylphenyl)-[1,3]oxazolo[5,4-b]pyridine (230 mg, 0.8 mmol), diphenylmethanimine (217 mg, 1.19 mmol), Tris(dibenzylideneacetone)dipalladium(0) (44 mg, 0.05 mmol), Xantphos (9,9-dimethyl-9H-xanthene-4,5-diyl)bis(diphenylphosphane) (41 mg, 0.07 mmol) and caesium carbonate (415 mg, 1.27 mmol) in N,N-dimethylacetamide (2 mL) was stirred under nitrogen at 120° C. for 16 hours. The mixture was cooled to room temperature. Water (50 mL) was added to the mixture. The mixture was then extracted with ethyl acetate (3×25 mL). The ethyl acetate layers were combined, dried over sodium sulphate and concentrated. The residue was dissolved in tetrahydrofuran (5 mL), treated with 2 N hydrochloric acid (2 mL) and stirred at room temperature for 1 hour. The crude material was purified by SCX and triturated with diethyl ether. 20 mg of 123 mg was purified by FCC (silica, 0-5% ethyl acetate in dichloromethane) to give the title compound 14 mg (8% yield) as a yellow solid.

Example 1, Method 14: 2-(3-Methylphenyl)-[1,3]oxazolo[5,4-b]pyridin-6-amine $\delta_H$ NMR (500 MHz, DMSO) 8.04-7.89 (m, 2H), 7.72 (d, J=2.5 Hz, 1H), 7.56-7.42 (m, 2H), 7.31 (d, J=2.5 Hz, 1H), 5.36 (s, 2H), 2.43 (s, 3H). Tr(MET-uHPLC-AB-101)=2.54 min, (ES$^+$) (M+H)$^+$ 226.

The following example was prepared using Method 14 described above:

TABLE 15

| Example | Structure | Mol. Weight | IUPAC Name | LCMS data |
|---|---|---|---|---|
| 1 | 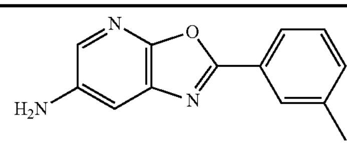 | 225.25 | 2-(3-Methylphenyl)-[1,3]oxazolo[5,4-b]pyridin-6-amine | Tr(MET-uHPLC-AB-101) = 2.54 min, (ES$^+$) (M + H)$^+$ 226 |

Method 15

Scheme for Method 15

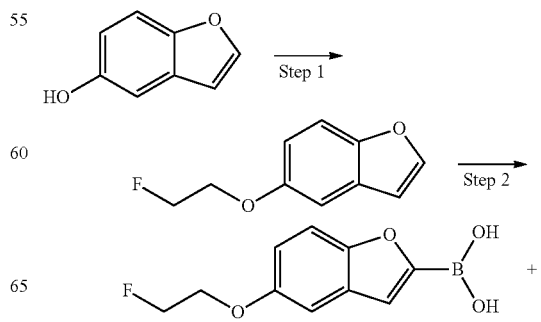

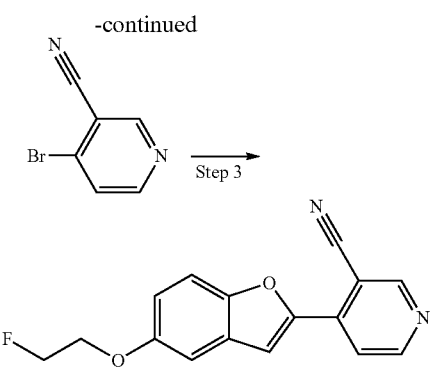

Step 1, Method 15: 5-(2-Fluoroethoxy)-1-benzofuran

To a stirred solution of 1-benzofuran-5-ol (275 mg, 2.05 mmol) in N,N-dimethylformamide (5 mL) was added 1-bromo-2-fluoroethane (306 µL, 4.10 mmol) and potassium carbonate (567 mg, 4.10 mmol), then heated to 60° C. for 18 hours. 1-Bromo-2-fluoroethane (150 µL, 2.00 mmol) was added and the reaction stirred at 60° C. for 4 hours. Potassium carbonate (273 mg, 2.00 mmol) was added and the mixture stirred at room temperature for 72 hours. Potassium carbonate (273 mg, 2.00 mmol) was added and the mixture heated to 80° C. for 5 hours. The mixture was cooled to room temperature, and water (10 mL) added. The mixture was extracted with ethyl acetate (3×10 mL) and the organic extracts combined, dried over magnesium sulphate, concentrated and purified by FCC (silica, 10-90% dichloromethane in heptane) to give the title compound 343 mg (93% yield) as a colorless oil. $\delta_H$ NMR (500 MHz, DMSO) 7.94 (d, J=2.1 Hz, 1H), 7.49 (d, J=8.9 Hz, 1H), 7.20 (d, J=2.5 Hz, 1H), 6.93 (dd, J=8.9, 2.5 Hz, 1H), 6.88 (s, 1H), 4.86-4.67 (m, 2H), 4.34-4.15 (m, 2H). Tr(METCR1278)=1.87 min, (ES$^+$) (M+H)$^+$ 181.

Step 2, Method 15: [5-(2-Fluoroethoxy)-1-benzofuran-2-yl]boronic acid

A solution of 1.6 M n-butyllithium in hexanes (1.78 mL, 2.85 mmol) was added drop-wise to a solution of 5-(2-fluoroethoxy)-1-benzofuran (0.34 g, 1.9 mmol) in anhydrous tetrahydrofuran (10 mL) at −78° C. The resulting mixture was stirred at −78° C. for 60 minutes and treated with triisopropyl borate (0.66 mL, 2.86 mmol). The reaction mixture was allowed to warm to room temperature and stirred overnight. The reaction was quenched with 6 N hydrochloric acid (10 mL) and extracted with tert-butyl methyl ether (3×20 mL). The combined extracts were washed with brine (20 mL), dried over magnesium sulphate, filtered and concentrated to give the title compound 0.36 g (67% yield containing 20% 5-(2-fluoroethoxy)-1-benzofuran) as an off white powder which was used in the next step without further purification.

Step 3, Method 15: 4-[5-(2-Fluoroethoxy)-1-benzofuran-2-yl]pyridine-3-carbonitrile To a stirred solution of [5-(2-fluoroethoxy)-1-benzofuran-2-yl]boronic acid (120 mg, 0.54 mmol) and 4-bromo-3-cyanopyridine (98 mg, 0.54 mmol) in 1,4-dioxane (3 mL) under nitrogen were added copper(I) iodide (10 mg, 0.054 mmol), caesium fluoride (163 mg, 1.07 mmol) and tetrakis(triphenylphosphine)palladium(0) (31 mg, 0.027 mmol). The reaction mixture was degassed using a stream of nitrogen for 10 minutes then heated under a nitrogen atmosphere to 60° C. and stirred for 18 hours. The mixture was concentrated, ethyl acetate (10 mL) and water (10 mL) added and the layers separated. The organic layer was washed with water (2×10 mL), brine (2×10 mL), dried over magnesium sulphate, filtered and concentrated. Purification by FCC (silica, 0-30% ethyl acetate in heptane) and recrystallisation from heptane-dichloromethane (5:2) gave the title compound 46 mg (30% yield) as a yellow solid.

Example 1, Method 15: 4-[5-(2-Fluoroethoxy)-1-benzofuran-2-yl]pyridine-3-carbonitrile $\delta_H$ NMR (500 MHz, DMSO) 9.11 (s, 1H), 8.92 (d, J=5.4 Hz, 1H), 8.07 (d, J=5.4 Hz, 1H), 7.93 (s, 1H), 7.64 (d, J=9.0 Hz, 1H), 7.40 (d, J=2.4 Hz, 1H), 7.13 (dd, J=9.0, 2.5 Hz, 1H), 4.78 (dt, J=47.9, 3.8 Hz, 2H), 4.30 (dt, J=30.1, 3.7 Hz, 2H). Tr(MET-uHPLC-AB-101)=3.21 min, (ES$^+$) (M+H)$^+$ 283.

The following example was prepared using Method 15 described above:

TABLE 16

| Example | Structure | Mol. Weight | IUPAC Name | LCMS data |
|---|---|---|---|---|
| 1 | ![structure] | 282.27 | 4-[5-(2-Fluoroethoxy)-1-benzofuran-2-yl]pyridine-3-carbonitrile | Tr(MET-uHPLC-AB-101) = 3.21 min, (ES$^+$) (M + H)$^+$ 283 |

Method 16

Scheme for Method 16

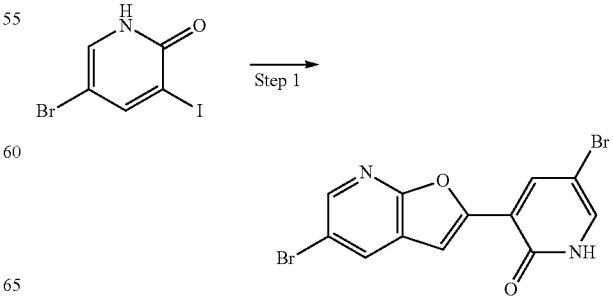

Step 1, Method 16: 5-Bromo-3-{5-bromofuro[2,3-b]pyridin-2-yl}-1,2-dihydropyridin-2-one A mixture of 5-bromo-3-iodo-1,2-dihydropyridin-2-one (6.5 g, 21.7 mmol, described in WO 2007/071434), ethynyl (trimethyl)silane (3.1 mL, 21.8 mol), copper(I) iodide (300 mg, 1.57 mmol) and triethylamine (15 mL, 108 mmol) in dry tetrahydrofuran (50 mL) was sonicated under a stream of nitrogen for 20 minutes. Bis(triphenylphosphine)palladium (II) dichloride (1.1 g, 1.57 mmol) was added and the mixture heated for 3 hours at 60° C. The mixture was cooled to room temperature, diluted with tetrahydrofuran (300 mL) and filtered. Purification by FCC (silica, 0-40% ethyl acetate in heptane) and recrystallisation from heptane/tetrahydrofuran (10 mL, 1:1) gave the title compound 120 mg (2% yield) as yellow needles.

Example 1, Method 16: 5-Bromo-3-{5-bromofuro[2,3-b]pyridin-2-yl}-1,2-dihydropyridin-2-one $\delta_H$ NMR (500 MHz, DMSO) 12.59 (s, 1H), 8.41 (d, J=2.3 Hz, 1H), 8.40 (d, J=2.3 Hz, 1H), 8.12 (d, J=2.7 Hz, 1H), 7.86 (d, J=2.7 Hz, 1H), 7.75 (s, 1H). Tr(MET-uHPLC-AB-101)=3.15 min, (ES$^+$) (M+H)$^+$ 371.

The following example was prepared using Method 16 described above:

TABLE 17

| Example | Structure | Mol. Weight | IUPAC Name | LCMS data |
|---|---|---|---|---|
| 1 | 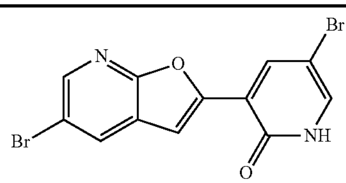 | 370.00 | 5-Bromo-3-{5-bromofuro[2,3-b]pyridin-2-yl}-1,2-dihydropyridin-2-one | Tr(MET-uHPLC-AB-101) = 3.15 min, (ES$^+$) (M + H)$^+$ 371 |

Method 17

Scheme for Method 17

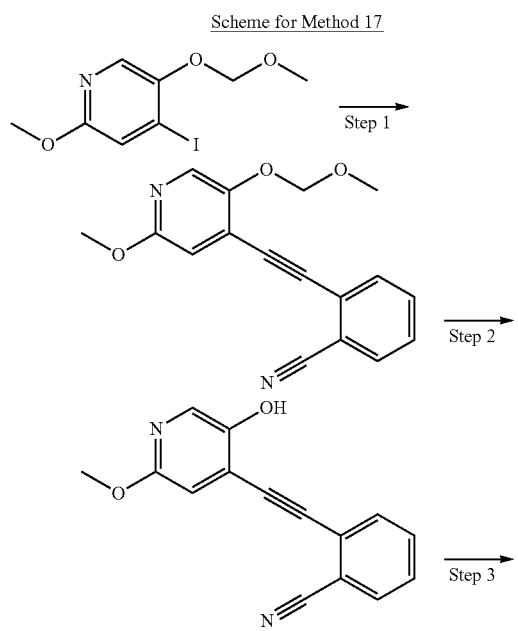

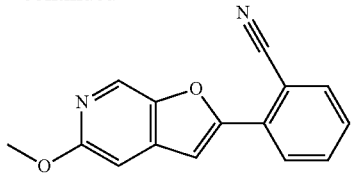

Step 1, Method 17: 2-{2-[2-Methoxy-5-(methoxymethoxy)pyridin-4-yl]ethynyl}benzonitrile A mixture of 4-iodo-2-methoxy-5-(methoxymethoxy)pyridine (100 mg, 0.34 mmol, described in Heterocycles, 2002, 57, 55), 2-ethynylbenzonitrile (65 mg, 0.51 mmol) and copper(I) iodide (20 mg, 0.11 mmol) in piperidine (1.5 mL) was sonicated under a stream of nitrogen for 15 minutes. Tetrakis(triphenylphosphine)palladium(0) (50 mg, 0.04 mmol) was added and the mixture stirred for 2 hours at 60° C. After cooling the volatiles were removed in vacuo and the residue taken up in ethyl acetate (100 mL) and absorbed onto a small amount of silica. Purification by FCC (silica, 0-30% ethyl acetate in heptane) gave the title compound 84 mg (84% yield) as an off-white solid. $\delta_H$ NMR (500 MHz, chloroform) 8.07 (s, 1H), 7.73-7.69 (m, 1H), 7.69-7.65 (m, 1H), 7.61 (dd, J=7.7, 1.3 Hz, 1H), 7.48 (dd, J=7.7, 1.2 Hz, 1H), 6.92 (s, 1H), 5.25 (s, 2H), 3.91 (s, 3H), 3.56 (s, 3H). Tr(METCR1278)=2.12 min, (ES$^+$) (M+H)$^+$ 295.

Step 2, Method 17: 2-[2-(5-Hydroxy-2-methoxypyridin-4-yl)ethynyl]benzonitrile

To a solution of 2-{2-[2-methoxy-5-(methoxymethoxy)pyridin-4-yl]ethynyl}benzonitrile (83 mg, 0.28 mmol) in tetrahydrofuran (3 mL) was added 3 M hydrochloric acid (1 mL) and the mixture stirred at 60° C. for 2 hours. After cooling the mixture was added to saturated aqueous sodium bicarbonate (50 mL) and extracted with ethyl acetate (3×50 mL). The combined organic extracts were washed with brine (50 mL), dried over magnesium sulphate, filtered and absorbed onto a small amount of silica. Purification by FCC (silica, 0-50% ethyl acetate in heptane) gave the title compound 70 mg (99% yield) as a colourless, crystalline solid. $\delta_H$ NMR (500 MHz, chloroform) 8.00 (s, 1H), 7.76-7.72 (m, 1H), 7.72-7.69 (m, 1H), 7.65 (td, J=7.7, 1.3 Hz, 1H), 7.52 (td, J=7.7, 1.3 Hz, 1H), 6.82 (s, 1H), 5.82 (s, 1H), 3.91 (s, 3H). Tr(METCR1278)=1.82 min, (ES$^+$) (M+H)$^+$ 251.

Step 3, Method 17: 2-{5-Methoxyfuro[2,3-c]pyridin-2-yl}benzonitrile

To a solution of 2-[2-(5-hydroxy-2-methoxypyridin-4-yl)ethynyl]benzonitrile (70 mg, 0.28 mmol) in hot toluene (5 mL) was added 1 M tetra-N-butylammonium fluoride in tetrahydrofuran (0.31 mL) and the mixture was stirred at 80° C. for 30 minutes. After cooling the volatiles were removed in vacuo and the resulting residue taken up in ethyl acetate (100 mL) and water (30 mL). The organic layer was separated, washed with brine (30 mL), dried over magnesium sulphate, filtered and concentrated. Purification by FCC (silica, 0-50% ethyl acetate in heptane) gave the title compound 45 mg (64% yield) as a colourless, crystalline solid.

Example 1, Method 17: 2-{5-Methoxyfuro[2,3-c]pyridin-2-yl}benzonitrile $\delta_H$ NMR (500 MHz, DMSO) 8.63 (s, 1H), 8.24-8.12 (m, 1H), 8.07 (dd, J=7.8, 0.9 Hz, 1H), 7.91 (td, J=7.8, 1.3 Hz, 1H), 7.71 (td, J=7.7, 1.1 Hz, 1H), 7.65 (d, J=0.7 Hz, 1H), 7.17 (d, J=0.9 Hz, 1H), 3.90 (s, 3H). Tr(MET-uHPLC-AB-101)=3.3 min, (ES$^+$) (M+H)$^+$ 251.

The following example was prepared using Method 17 described above:

TABLE 18

| Example | Structure | Mol. Weight | IUPAC Name | LCMS data |
|---|---|---|---|---|
| 1 | 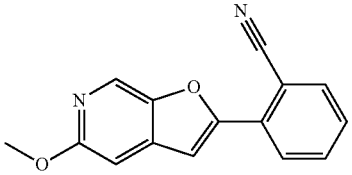 [SMILES: COc1cc2cc(-c3ccccc3C#N)oc2cn1] | 250.25 | 2-{5-Methoxyfuro[2,3-c]pyridin-2-yl}benzonitrile | Tr(MET-uHPLC-AB-101) = 3.3 min, (ES$^+$) (M + H)$^+$ 251 |

Method 18

Scheme for Method 18

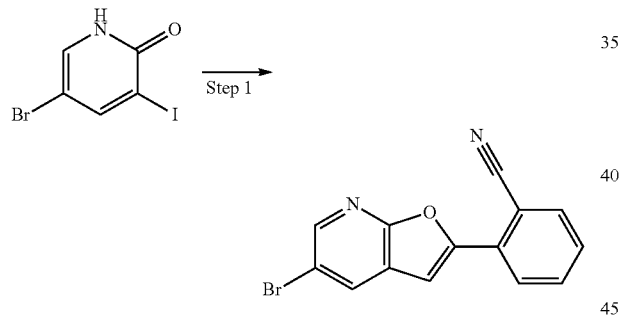

Step 1, Method 18: 2-{5-Bromofuro[2,3-b]pyridin-2-yl}benzonitrile

A mixture of 5-bromo-3-iodopyridin-2-ol (0.16 g, 0.53 mmol), 2-ethynylbenzonitrile (0.1 g, 0.8 mmol) and copper (I) iodide (0.03 g, 0.16 mmol) in piperidine (1.5 mL) was sonicated under a stream of nitrogen for 10 minutes. Tetrakis(triphenylphosphine)palladium(0) (62 mg, 0.05 mmol) was added and the mixture stirred for 2 hours at 60° C. After cooling the volatiles were removed in vacuo and the residue taken up in ethyl acetate (100 mL) and absorbed onto a small amount of silica. Purification by FCC (silica, 0-30% ethyl acetate in heptane) and recrystallisation from heptane/ethyl acetate (10 mL, 1:1) gave the title compound 25 mg (16% yield) as an off-white, crystalline solid.

Example 1, Method 18: 2-{5-Bromofuro[2,3-b]pyridin-2-yl}benzonitrile $\delta_H$ NMR (500 MHz, DMSO) 8.56 (d, J=2.3 Hz, 1H), 8.50 (d, J=2.3 Hz, 1H), 8.17 (d, J=7.5 Hz, 1H), 8.09-8.03 (m, 1H), 7.91 (td, J=7.9, 1.3 Hz, 1H), 7.73 (s, 1H), 7.69 (td, J=7.7, 1.1 Hz, 1H). Tr(MET-uHPLC-AB-101)=3.77 min, (ES$^+$) (M+H)$^+$ 299/301.

The following examples were prepared using Method 18 described above:

TABLE 19

| Example | Structure | Mol. Weight | IUPAC Name | LCMS data |
|---|---|---|---|---|
| 1 | 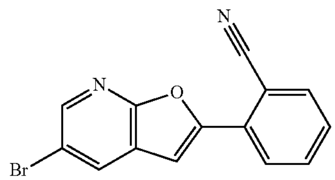 [SMILES: N#Cc1ccccc1-c1cc2cc(Br)cnc2o1] | 299.12 | 2-{5-Bromofuro[2,3-b]pyridin-2-yl}benzonitrile | Tr(MET-uHPLC-AB-101) = 3.77 min, (ES$^+$) (M + H)$^+$ 299/301 |
| 2 | 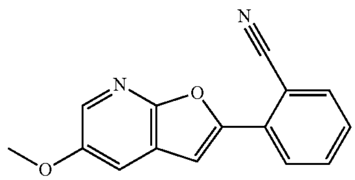 [SMILES: COc1cnc2oc(-c3ccccc3C#N)cc2c1] | 250.25 | 2-{5-Methoxyfuro[2,3-b]pyridin-2-yl}benzonitrile | Tr(MET-uHPLC-AB-101) = 3.26 min, (ES$^+$) (M + H)$^+$ 251 |

Method 19

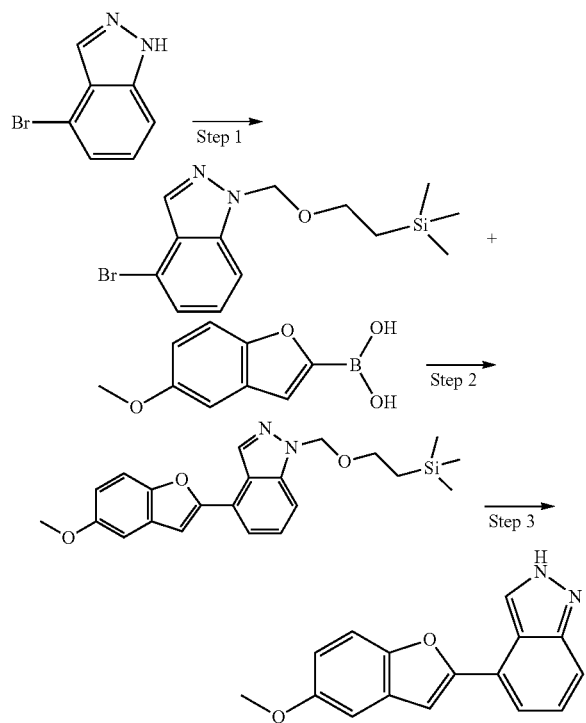

Scheme for Method 19

Step 1, Method 19: 4-Bromo-1-{[2-(trimethylsilyl)ethoxy]methyl}-1H-indazole

4-Bromo-1H-indazole (250 mg, 1.27 mmol) in anhydrous N,N-dimethylformamide (2 mL) was added drop-wise to a stirred solution of sodium hydride (60% in mineral oil, 61 mg, 1.52 mmol) in anhydrous N,N-dimethylformamide (3 mL) at 0° C. in a nitrogen atmosphere and stirred for 1 hour. 2-(Trimethylsilyl)ethoxymethyl chloride (0.22 mL, 1.27 mmol) was added drop-wise and the reaction warmed to room temperature and stirred for 3 hours. Water (1 mL) was and the mixture extracted with ethyl acetate (3×80 mL). The combined organic extracts were washed with brine (10 mL), dried over sodium sulphate, filtered and concentrated. Purification by FCC (silica, 0-15% ethyl acetate in heptane) gave the title compound 400 mg (95% yield) as an orange oil as a mixture of two N-regioisomers. Tr(METCR1278)=2.45/2.56 min, (ES$^+$) (M+H)$^+$ 327/329, 30%/70%.

Step 2, Method 19: 4-(5-Methoxy-1-benzofuran-2-yl)-1-{[2-(trimethylsilyl)ethoxy]methyl}-1H-indazole 2 M tripotassium phosphate (1.1 mL) was added to a stirred suspension of (5-methoxy-1-benzofuran-2-yl)boronic acid (190 mg, 0.99 mmol, prepared by Method 3) and 4-bromo-1-{[2-(trimethylsilyl)ethoxy]methyl}-1H-indazole (95%, 409 mg, 1.19 mmol) in 1,4-dioxane (10 mL) at room temperature. The mixture was sonicated under a flow of nitrogen for 10 minutes then (1R,4S)-bicyclo[2.2.1]hept-2-yl[(1S,4R)-bicyclo[2.2.1]hept-2-yl]phosphane-chloro[2'-(dimethylamino)biphenyl-2-yl]palladium (1:1) (27.73 mg, 0.05 mmol) was added and heated at 90° C. for 15 hours. The reaction mixture was cooled to room temperature and the solvents removed in vacuo. The residue was partitioned between ethyl acetate (50 mL) and water (20 mL), the phases separated and the aqueous extracted with ethyl acetate (2×20 mL). The combined organic extracts were washed with brine (10 mL), dried over sodium sulphate, filtered and concentrated. Purification by FCC (silica, 0-40% ethyl acetate in heptane) gave the title compound 279 mg (71% yield) as a yellow oil which solidified upon standing and as a mixture of regioisomers. Tr(METCR1278)=2.70/2.81 min, (ES$^+$) (M+H)$^+$ 395.

Step 3, Method 19: 4-(5-Methoxy-1-benzofuran-2-yl)-1H-indazole 4-(5-Methoxy-1-benzofuran-2-yl)-1-{[2-(trimethylsilyl)ethoxy]methyl}-1H-indazole (150 mg, 0.38 mmol) was dissolved in methanol (10 mL), concentrated hydrochloric acid (3 mL) added and the reaction heated to 40° C. for 2 hours, then to 50° C. for 4 hours. The reaction was cooled to room temperature and methanol removed in vacuo. The reaction mixture was basified by portion-wise addition of sodium bicarbonate until pH 10. The product was extracted with ethyl acetate (3×30 mL), the combined organic extracts washed with brine (10 mL), dried over sodium sulphate, filtered and concentrated. Purification by preparative HPLC (acetonitrile-water-0.2% ammonium hydroxide) gave the title compound 30 mg (29% yield) as an off white powder.

Example 1, Method 19:
4-(5-Methoxy-1-benzofuran-2-yl)-1H-indazole $\delta_H$ NMR (500 MHz, DMSO) 13.35 (br. s, 1H), 8.63 (s, 1H), 7.72 (d, J=7.1 Hz, 1H), 7.66-7.56 (m, 3H), 7.52-7.42 (m, 1H), 7.20 (d, J=2.6 Hz, 1H), 6.96 (dd, J=8.9, 2.6 Hz, 1H), 3.83 (s, 3H). Tr(MET-uHPLC-AB-101)=3.32 min, (ES$^+$) (M+H)$^+$ 265.

The following examples were prepared using Method 19 described above:

TABLE 20

| Example | Structure | Mol. Weight | IUPAC Name | LCMS data |
|---|---|---|---|---|
| 1 | 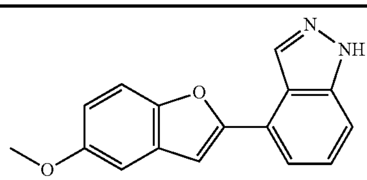 | 264.28 | 4-(5-Methoxy-1-benzofuran-2-yl)-1H-indazole | Tr(MET-uHPLC-AB-101) = 3.32 min, (ES$^+$) (M + H)$^+$ 265 |
| 2 | 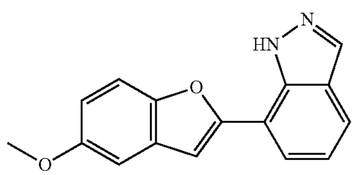 [SMILES: COc1ccc2oc(-c3cccc4cn[nH]c34)cc2c1] | 264.28 | 7-(5-Methoxy-1-benzofuran-2-yl)-1H-indazole | Tr(MET-uHPLC-AB-101) = 3.44 min, (ES$^+$) (M + H)$^+$ 265 |

Method 20

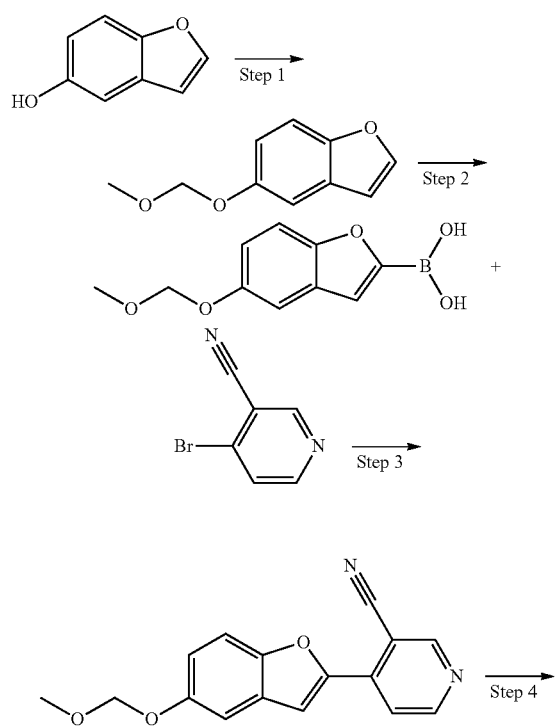

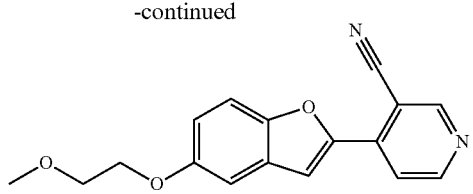

Step 1, Method 20: 5-(Methoxymethoxy)-1-benzofuran

Sodium hydride (60% in mineral oil, 579 mg, 14.48 mmol) was suspended in anhydrous N,N-dimethylformamide (25 mL) and cooled to 0° C. 5-Hydroxybenzofuran (1.85 g, 13.79 mmol) dissolved in N,N-dimethylformamide (10 mL) was added slowly. The reaction mixture was stirred under nitrogen and warmed to room temperature over 1.5 hours. The mixture was cooled to 0° C. and chloro(methoxy)methane (1.1 mL, 14.48 mmol) added drop-wise over 30 minutes. The mixture was warmed to room temperature and stirred for 3 hours. Water (5 mL) was added and the mixture extracted with ethyl acetate (3×50 mL). The combined organic extracts were washed with water (5×50 mL), brine (10 mL), dried over anhydrous magnesium sulphate, filtered and concentrated to give the title compound 2.3 g (89% yield) as a pale yellow oil. Tr(METCR1278)=1.95 min, no ionization.

Step 2, Method 20: [5-(Methoxymethoxy)-1-benzofuran-2-yl]boronic acid 5-(Methoxymethoxy)-1-benzofuran (1.00 g, 5.35 mmol) was dissolved in anhydrous tetrahydrofuran (15 mL) and cooled to −78° C. under nitrogen. 1.6 M n-butyllithium in hexanes (3.51 mL, 5.62 mmol) was added drop-wise and the mixture stirred for 1 hour at −78° C. Triisopropylborate (2.47 mL, 10.7 mmol) was added drop-wise and the reaction mixture was stirred for 2 hours. The reaction mixture was warmed to room temperature and stirred for 1 hour. 2 M hydrochloric acid (16 mL) was added slowly and the reaction stirred for 1 hour. The reaction mixture was diluted with water (10 mL) and extracted with tert-butyl methyl ether (3×40 mL). The combined organic extracts were washed with brine (10 mL), dried over anhydrous magnesium sulphate, filtered and concentrated. Purification by FCC (silica, 20-80% ethyl acetate in heptane) gave the crude title compound 374 mg (31% yield) as a beige solid which was used in the next step without further purification.

Step 3, Method 20: 4-[5-(Methoxymethoxy)-1-benzofuran-2-yl]pyridine-3-carbonitrile

[5-(Methoxymethoxy)-1-benzofuran-2-yl]boronic acid (374 mg, 1.68 mmol), 4-bromopyridine-3-carbonitrile (339 mg, 1.85 mmol) and 2 M tripotassium phosphate (1.7 mL) were suspended in N,N-dimethylformamide (20 mL) and sonicated under a flow of nitrogen for 5 minutes. (1R,4S)-Bicyclo[2.2.1]hept-2-yl[(1S,4R)-bicyclo[2.2.1]hept-2-yl]phosphane-chloro[2'-(dimethylamino)biphenyl-2-yl]palladium (1:1) (47 mg, 0.08 mmol) was added and the reaction heated to 75° C. for 1.5 hours. The reaction was cooled to room temperature and the solvents removed in vacuo. The residue was partitioned between ethyl acetate (50 mL) and water (20 mL), the phases separated and the aqueous layer extracted with ethyl acetate (2×50 mL). The combined organic extracts were washed with brine (10 mL), dried over sodium sulphate, filtered and concentrated. Purification by FCC (silica, 0-50% ethyl acetate in heptane) gave the title compound 254 mg (52% yield) as a pale yellow solid. Tr(MET-uHPLC-AB-101)=3.20 min, (ES$^+$) (M+H)$^+$ 281.

Step 4, Method 20: 4-(5-Hydroxy-1-benzofuran-2-yl)pyridine-3-carbonitrile

To a solution of 4-[5-(methoxymethoxy)-1-benzofuran-2-yl]pyridine-3-carbonitrile (240 mg, 0.86 mmol) in tetrahydrofuran (10 mL) was added 3 M hydrochloric acid (2.8 mL) and the mixture stirred at 60° C. for 2 hours. The reaction mixture was cooled to room temperature and saturated aqueous sodium bicarbonate (50 mL) and ethyl acetate (100 mL) added. The mixture was filtered (GF/F paper) and dried under vacuum for 2 hours to give the title compound 207 mg (quantitative yield) as a yellow solid. Tr(MET-uHPLC-AB-101)=2.41 min, (ES$^+$) (M+H) 237.

Step 5, Method 20: 4-[5-(2-Methoxyethoxy)-1-benzofuran-2-yl]pyridine-3-carbonitrile 4-(5-Hydroxy-1-benzofuran-2-yl)pyridine-3-carbonitrile (98%, 50 mg, 0.21 mmol), 1-bromo-2-methoxyethane (58 μL, 0.62 mmol) and potassium carbonate (57 mg, 0.41 mmol) were suspended in anhydrous N,N-dimethylformamide (2 mL) and stirred under nitrogen at 60° C. for 4 days. The reaction mixture was cooled to room temperature and concentrated. The residue was partitioned between ethyl acetate (20 mL) and water (10 mL); the phases were separated and the aqueous extracted with ethyl acetate (2×20 mL). The combined organic extracts were washed with brine (10 mL), dried over sodium sulphate, filtered and concentrated. Purification by FCC (silica, 0-60% ethyl acetate in heptane) gave the title compound 23.9 mg (38% yield) as a pale yellow solid.

Example 1, Method 20: 4-[5-(2-Methoxyethoxy)-1-benzofuran-2-yl]pyridine-3-carbonitrile $\delta_H$ NMR (500 MHz, DMSO) 9.12 (s, 1H), 8.92 (d, J=5.4 Hz, 1H), 8.07 (d, J=5.4 Hz, 1H), 7.94 (s, 1H), 7.63 (d, J=9.0 Hz, 1H), 7.38 (d, J=2.6 Hz, 1H), 7.10 (dd, J=9.0, 2.6 Hz, 1H), 4.15 (dd, J=5.4, 3.8 Hz, 2H), 3.70 (dd, J=5.3, 3.8 Hz, 2H), 3.33 (s, 3H). Tr(MET-uHPLC-AB-101)=3.1 min, (ES$^+$) (M+H)$^+$ 295.

The following examples were prepared using Method 20 described above:

TABLE 21

| Example | Structure | Mol. Weight | IUPAC Name | LCMS data |
|---|---|---|---|---|
| 1 | 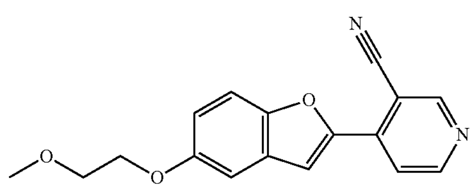 [SMILES: COCCOc1ccc2oc(-c3ccncc3C#N)cc2c1] | 294.30 | 4-[5-(2-Methoxyethoxy)-1-benzofuran-2-yl]pyridine-3-carbonitrile | Tr(MET-uHPLC-AB-101) = 3.1 min, (ES$^+$) (M + H)$^+$ 295 |
| 2 | 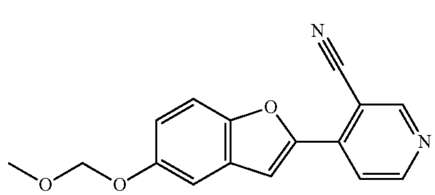 [SMILES: COCOc1ccc2oc(-c3ccncc3C#N)cc2c1] | 280.28 | 4-[5-(Methoxymethoxy)-1-benzofuran-2-yl]pyridine-3-carbonitrile | Tr(MET-uHPLC-AB-101) = 3.2 min, (ES$^+$) (M + H)$^+$ 281 |

TABLE 21-continued

| Example | Structure | Mol. Weight | IUPAC Name | LCMS data |
|---|---|---|---|---|
| 3 | 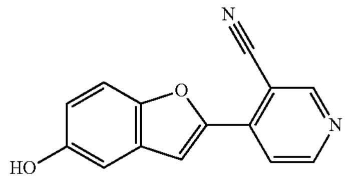 [SMILES: N#Cc1cnccc1-c1cc2cc(O)ccc2o1] | 236.23 | 4-(5-Hydroxy-1-benzofuran-2-yl)pyridine-3-carbonitrile | Tr(MET-uHPLC-AB-101) = 2.41 min, (ES+) (M + H)+ 237 |
| 4 | 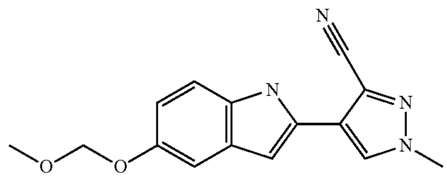 | 283.28 | 4-[5-(Methoxymethoxy)-1-benzofuran-2-yl]-1-methyl-1H-pyrazole-3-carbonitrile | Tr(MET-uHPLC-AB-101) = 3.31 min, (ES+) (M + H)+ 284 |

Method 21

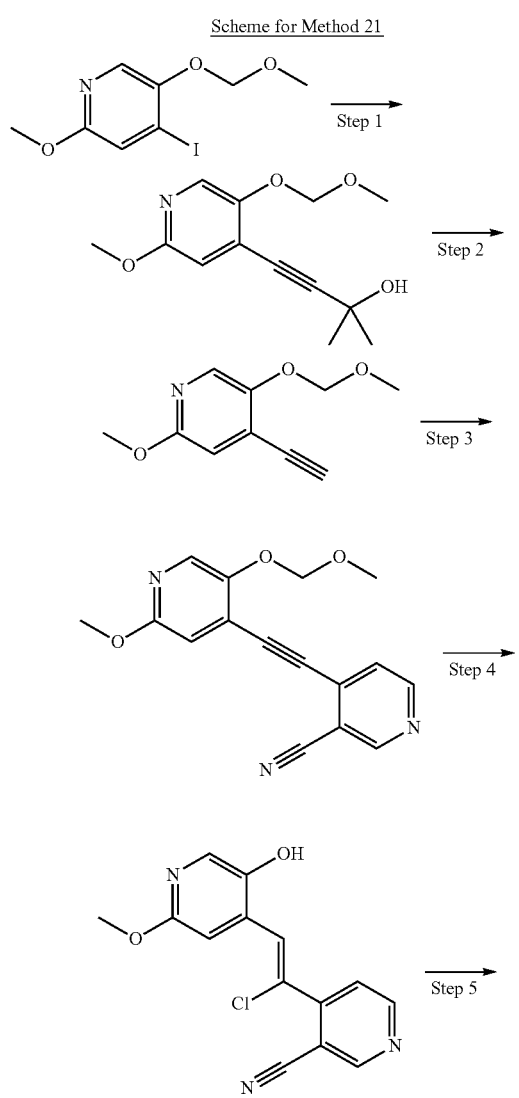

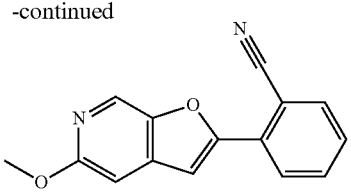

Step 1, Method 21: 4-(3-Hydroxy-3-methylbut-1-yn-1-yl)-5-(methoxymethoxy)pyridin-2-ol A mixture of 4-iodo-2-methoxy-5-(methoxymethoxy)pyridine (0.51 g, 1.73 mmol, described in Heterocycles, 2002, 57, 55-71), 2-methylbut-3-yn-2-ol (1.3 mL, 13.3 mmol) and copper(I) iodide (100 mg, 0.53 mmol) in piperidine (10 mL) was sonicated under a stream of nitrogen for 15 minutes. Tetrakis(triphenylphosphine)palladium (0) (0.2 g, 0.17 mmol) was added and the mixture stirred for 2 hours at 60° C. After cooling to room temperature the volatiles were removed in vacuo and the residue taken up in ethyl acetate (100 mL) and absorbed onto a small amount of silica. Purification by FCC (silica, 0-40% ethyl acetate in heptane) gave the title compound 577 mg (approximately 75% purity quantitative yield.) as a brownish oil. $\delta_H$ NMR (500 MHz, chloroform) 7.96 (s, 1H), 6.73 (s, 1H), 5.14 (s, 2H), 3.87 (s, 3H), 3.54 (s, 3H), 2.39 (s, 1H), 1.61 (s, 6H). Tr(METCR1278)=1.70 min, (ES+) (M+H)+ 252.

Step 2, Method 21: 4-Ethynyl-2-methoxy-5-(methoxymethoxy)pyridine

Tetrabutylammonium hydroxide (5.0 g, 40 wt % solution in water) in methanol (100 mL) was concentrated to a volume of approximately 5 mL and an aliquot (0.25 mL) was added to a solution of 4-[2-methoxy-5-(methoxymethoxy)pyridin-4-yl]-2-methylbut-3-yn-2-ol (75%, 577 g, 1.75 mg, 0.53 mmol) in toluene (100 mL) at 70° C. and the mixture stirred for 30 minutes. After cooling to room temperature the mixture was diluted with ethyl acetate (200 mL), washed with brine (100 mL), dried over magnesium sulphate, filtered and concentrated. Purification by FCC (silica, 0-40% ethyl acetate in heptane) gave the title compound 229 mg (68% yield) as an off-white crystalline solid. $\delta_H$ NMR (500 MHz, chloroform) 8.03 (s, 1H), 6.82 (s, 1H), 5.18 (s, 2H), 3.89 (s, 3H), 3.54 (s, 3H), 3.41 (s, 1H). Tr(METCR1278) =1.77 min, (ES⁺) (M+H)⁺ 194.

Step 3, Method 21: 4-{2-[2-Methoxy-5-(methoxymethoxy)pyridin-4-yl]ethynyl}pyridine-3-carbonitrile A mixture of 4-ethynyl-2-methoxy-5-(methoxymethoxy) pyridine (100 mg, 0.52 mmol), 4-iodopyridine-3-carbonitrile (119 mg, 0.52 mmol) and copper(I) iodide (20 mg, 0.11 mmol) in tetrahydrofuran (3 mL) and triethylamine (360 µL, 2.58 mmol) was sonicated under a stream of nitrogen for 10 minutes. Bis(triphenylphosphine)palladium(II) dichloride (30 mg, 0.04 mmol) was added and the mixture was stirred at 60° C. for 4 hours. After cooling the volatiles were removed in vacuo and the residue taken up in ethyl acetate (200 mL), washed with brine (50 mL), dried over magnesium sulphate, filtered and concentrated. Purification by FCC (silica, 0-50% ethyl acetate in heptane) gave the title compound 115 mg (75% yield) as an off-white solid. $\delta_H$ NMR (500 MHz, chloroform) 8.92 (s, 1H), 8.80 (d, J=5.2 Hz, 1H), 8.10 (s, 1H), 7.60-7.48 (m, 1H), 6.92 (s, 1H), 5.24 (s, 2H), 3.91 (s, 3H), 3.55 (s, 3H). Tr(METCR1278)=1.95 min, (ES⁺) (M+H)⁺ 296.

Step 4, Method 21: 4-[(Z)-1-Chloro-2-(5-hydroxy-2-methoxypyridin-4-yl)ethenyl]pyridine-3-carbonitrile To a solution of 4-{2-[2-methoxy-5-(methoxymethoxy)pyridin-4-yl]ethynyl}pyridine-3-carbonitrile (115 mg, 0.39 mmol) in tetrahydrofuran (5 mL) was added 3 M hydrochloric acid (3 mL) and the mixture stirred at 60° C. for 90 minutes. After cooling the mixture was partitioned between ethyl acetate (200 mL) and saturated aqueous sodium bicarbonate (50 mL). The organic layer was washed with brine (50 mL), dried over magnesium sulphate, filtered and absorbed onto a small amount of silica. Purification by FCC (silica, 10-80% ethyl acetate in heptane) gave the title compound 95 mg (85% yield) as a yellowish, crystalline solid. $\delta_H$ NMR (500 MHz, DMSO) 10.40 (s, 1H), 9.11 (s, 1H), 8.92 (d, J=5.3 Hz, 1H), 8.00 (d, J=5.3 Hz, 1H), 7.91 (s, 1H), 7.82 (s, 1H), 6.96 (s, 1H), 3.81 (s, 3H). Tr(METCR1278)=1.74 min, (ES⁺) (M+H)⁺ 288.

Step 5, Method 21: 4-{5-Methoxyfuro[2,3-c]pyridin-2-yl}pyridine-3-carbonitrile To a solution of 4-[(Z)-1-chloro-2-(5-hydroxy-2-methoxypyridin-4-yl)ethenyl]pyridine-3-carbonitrile (92 mg, 0.32 mmol) in toluene (10 mL) was added tetra-N-butylammonium fluoride (1 M in tetrahydrofuran, 0.70 mL) and the mixture stirred at 80° C. for 30 minutes. After cooling the mixture was diluted with ethyl acetate (150 mL), washed with water (50 mL) and brine (50 mL), dried over magnesium sulphate, filtered and concentrated. Purification by FCC (silica, 0-60% ethyl acetate in heptane) and recrystallisation from heptane/ethyl acetate (10 mL, 1:1) gave the title compound 19 mg (24% yield) as a colourless, crystalline solid.

Example 1, Method 21: 4-{5-Methoxyfuro[2,3-c]pyridin-2-yl}pyridine-3-carbonitrile ¹H NMR (500 MHz, DMSO) 9.19 (s, 1H), 9.00 (d, J=5.3 Hz, 1H), 8.70 (s, 1H), 8.15 (d, J=5.3 Hz, 1H), 7.93 (s, 1H), 7.23 (d, J=0.8 Hz, 1H), 3.90 (s, 3H). Tr(MET-uHPLC-AB-101)=2.67 min, (ES⁺) (M+H)⁺ 252.

The following example was prepared using Method 21 described above:

TABLE 22

| Example | Structure | Mol. Weight | IUPAC Name | LCMS data |
|---|---|---|---|---|
| 1 | 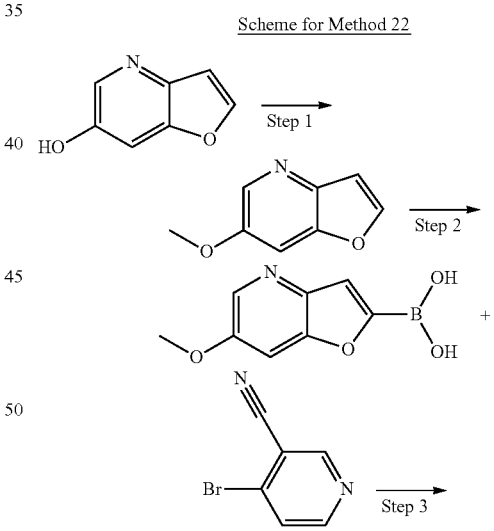 | 251.24 | 4-{5-Methoxyfuro[2,3-c]pyridin-2-yl}pyridine-3-carbonitrile | Tr(MET-uHPLC-AB-101) = 2.67 min, (ES⁺) (M + H)⁺ 252 |

Method 22

Scheme for Method 22

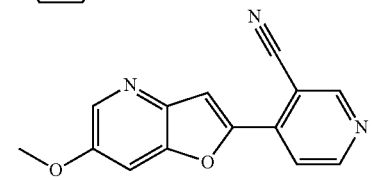

Step 1, Method 22: 6-Methoxyfuro[3,2-b]pyridine

Sodium hydride (60% in mineral oil, 0.02 g, 0.56 mmol) was added to furo[3,2-b]pyridin-6-ol (0.05 g, 0.37 mmol) in N,N-dimethylformamide (2 mL) and the mixture stirred under nitrogen for 30 minutes. Iodomethane (34 µL, 0.56 mmol) was added and the mixture stirred overnight at room temperature. The reaction was quenched by the addition of methanol and the mixture concentrated, suspended in saturated aqueous ammonium chloride (20 mL) and extracted with ethyl acetate (3×10 mL). The combined organic extracts were dried over sodium sulphate, filtered and concentrated to give the title compound 0.21 g (66% yield 17% pure) as a brown oil which was used in the next step without further purification. Tr(METCR1278)=1.23 min, (ES$^+$) (M+H)$^+$ 150.

Step 2, Method 22: 6-Methoxyfuro[3,2-b]pyridin-2-yl}boronic acid 1.6 M n-Butyllithium in hexanes (1.07 mL, 1.71 mmol) was added drop-wise to a solution of 6-methoxyfuro[3,2-b]pyridine (170 mg, 1.14 mmol) in anhydrous tetrahydrofuran (10 mL) at −78° C. The mixture was stirred at −78° C. for 30 minutes and treated with triisopropyl borate (0.4 mL, 1.71 mmol). The reaction mixture was warmed to room temperature and stirred overnight. The reaction was quenched with 6 N hydrochloric acid (5 mL) at 0° C. The pH was adjusted to 7 with saturated aqueous sodium bicarbonate and extracted with ethyl acetate (2×3 mL). The combined organic extracts were extracted with 2 M sodium carbonate (2×3 mL), the aqueous layers combined, acidified to pH 4 (acetic acid) and extracted with ethyl acetate (3×10 mL). Solid stuck to the side of the separating funnel was dissolved in methanol (10 mL) and diluted with dichloromethane (10 mL), combined with the ethyl acetate extract, dried over magnesium sulphate, filtered and concentrated under reduced pressure at room temperature. Trituration with ethyl acetate (5 mL) gave the title compound 244 mg (50% yield, 45% purity) as a tan powder which was used in the next step without further purification. Tr(METCR1278)=1.02 min, (ES$^+$) (M+H)$^+$ 194, 45%.

Step 3 Method 22: 4-{6-Methoxyfuro[3,2-b]pyridin-2-yl}pyridine-3-carbonitrile A sealed tube was charged with {6-methoxyfuro[3,2-b]pyridin-2-yl}boronic acid (45%, 150 mg, 0.35 mmol), 4-bromopyridine-3-carbonitrile (77 mg, 0.42 mmol), copper (I) iodide (7 mg, 0.03 mmol), caesium fluoride (106 mg, 0.7 mmol), 1,4-dioxane (3 mL) and the mixture degassed with nitrogen. Tetrakis(triphenylphosphine)palladium(0) (20 mg, 0.02 mmol) was added and the reaction mixture stirred vigorously under nitrogen at 60° C. overnight. The mixture was filtered, washed with ethyl acetate (10 mL), water (5 mL), dichloromethane (10 mL) and methanol (5 mL). The washings were combined and extracted with ethyl acetate (3×10 mL), dried over sodium sulphate, filtered and concentrated. Recrystallisation from methanol (5 mL) gave the title compound 2.5 mg (3% yield) as a tan powder.

Example 1, Method 22: 4-{6-Methoxyfuro[3,2-b]pyridin-2-yl}pyridine-3-carbonitrile δ$_H$ NMR (500 MHz, DMSO) 9.14 (s, 1H), 8.95 (d, J=5.4 Hz, 1H), 8.43 (d, J=2.5 Hz, 1H), 8.09 (d, J=5.4 Hz, 1H), 8.07 (s, 1H), 7.87 (d, J=1.9 Hz, 1H), 3.94 (s, 3H). Tr(MET-uHPLC-AB-101)=2.4 min, (ES$^+$) (M+H)$^+$ 252.

The following example was prepared using Method 22 described above:

TABLE 23

| Example | Structure | Mol. Weight | IUPAC Name | LCMS data |
| --- | --- | --- | --- | --- |
| 1 | 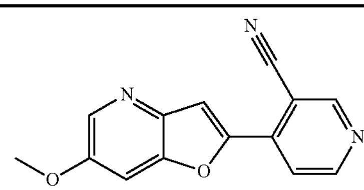 | 251.24 | 4-{6-Methoxyfuro[3,2-b]pyridin-2-yl}pyridine-3-carbonitrile | Tr(MET-uHPLC-AB-101) = 2.4 min, (ES$^+$) (M + H)$^+$ 252 |

Method 23

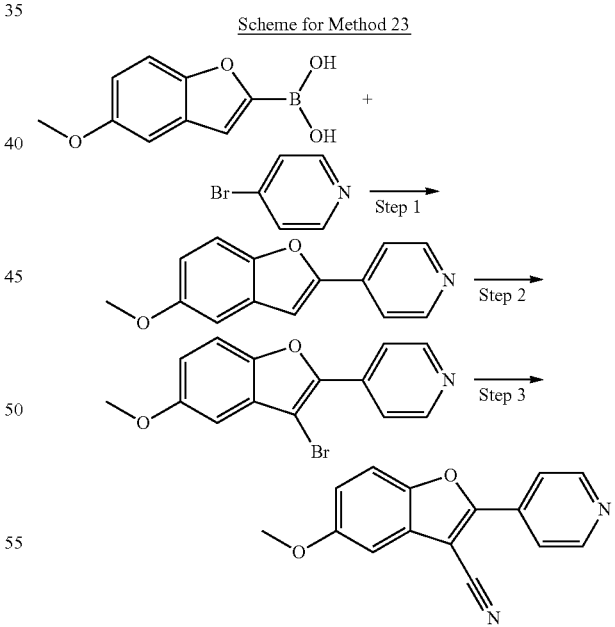

Scheme for Method 23

Step 1, Method 23: 4-(5-Methoxy-1-benzofuran-2-yl)pyridine (5-Methoxy-1-benzofuran-2-yl)boronic acid (140 mg, 0.73 mmol, prepared by Method 3), 4-bromopyridine (127 mg, 0.8 mmol) and 2 M sodium carbonate (0.72 mL) were suspended in N,N-dimethylformamide (5 mL) and sonicated under a flow of nitrogen for 5 minutes. Tetrakis(triphenylphosphine)palladium(0) (42 mg, 0.04 mmol) was added and the reaction heated to 70° C. for 16 hours. The reaction was allowed to cool to room temperature and the solvents removed in vacuo. The residue was suspended in ethyl acetate (50 mL) and filtered through a celite pad. The pad was washed with ethyl acetate (2×20 mL), the organics washed with water (20 mL) and the aqueous was extracted with ethyl acetate (2×20 mL). The combined organic extracts were washed with brine (10 mL), dried over sodium sulphate, filtered and concentrated. Purification by FCC (silica, 20-80% ethyl acetate in heptane) gave the title compound 70 mg (42% yield) as a tan powder. $\delta_H$ NMR (500 MHz, DMSO) 8.68 (d, J=6.1 Hz, 2H), 7.92-7.75 (m, 2H), 7.68 (s, 1H), 7.58 (d, J=9.0 Hz, 1H), 7.23 (d, J=2.6 Hz, 1H), 7.00 (dd, J=9.0, 2.6 Hz, 1H), 3.81 (s, 3H). Tr(MET-uHPLC-AB-101)=1.73 min, (ES$^+$) (M+H)$^+$ 226.

Step 2, Method 23:
4-(3-Bromo-5-methoxy-1-benzofuran-2-yl)pyridine 4-(5-Methoxy-1-benzofuran-2-yl)pyridine (86%, 303 mg, 1.16 mmol) and N-bromosuccinimide (247 mg, 1.39 mmol) were dissolved in dichloromethane (5 mL) and stirred for 4 hours at room temperature. Saturated aqueous sodium bicarbonate (5 mL) was added and the reaction mixture extracted with dichloromethane (3×10 mL). The combined organics were washed with brine (5 mL), dried over sodium sulphate, filtered and concentrated. The residue was dissolved in dichloromethane (1 mL) and N-bromosuccinimide (247 mg, 1.39 mmol) added. The reaction mixture was stirred at room temperature for 4 hours. Saturated aqueous sodium bicarbonate (5 mL) was added and the reaction mixture extracted with dichloromethane (3×10 mL). The combined organic extracts were washed with brine (5 mL), dried over sodium sulphate, filtered and concentrated in vacuo. Purification by FCC (silica, 20-60% ethyl acetate in heptane) and recrystallisation from ethanol gave the title compound 43 mg (12% yield) as a yellow solid. Tr(MET-uHPLC-AB-101)=2.29 min, (ES$^+$) (M+H)$^+$ 304/306.

Step 3, Method 23: 5-Methoxy-2-(pyridin-4-yl)-1-benzofuran-3-carbonitrile 4-(3-Bromo-5-methoxy-1-benzofuran-2-yl)pyridine (43 mg, 0.14 mmol), zinc(II) cyanide (18 mg, 0.16 mmol) and tetrakis(triphenylphosphine)palladium(0) (8 mg, 0.01 mmol) were suspended in N,N-dimethylacetamide (1 mL) and heated in a microwave at 180° C. for 10 minutes. The solvents were removed in vacuo and the reaction mixture diluted with ethyl acetate (10 mL) and partitioned with water (10 mL). The aqueous was extracted with ethyl acetate (2×5 mL) and the combined organic extracts washed with water (5×3 mL), brine (3 mL), dried over sodium sulphate, filtered and concentrated. Purification by FCC (silica, 20-80% ethyl acetate in heptane) and recrystallisation from ethanol gave the title compound, 13 mg (37% yield) as a flocculent, white solid.

Example 1, Method 23: 5-Methoxy-2-(pyridin-4-yl)-1-benzofuran-3-carbonitrile $\delta_H$ NMR (500 MHz, DMSO) 8.79-8.66 (m, 2H), 8.04 (d, J=9.2 Hz, 1H), 8.02-7.82 (m, 3H), 7.31 (d, J=9.2 Hz, 1H), 3.98 (s, 3H). Tr(MET-uHPLC-AB-101)=1.96 min, (ES$^+$) (M+H)$^+$ 251.

The following examples were prepared using Method 23 described above:

TABLE 24

| Example | Structure | Mol. Weight | IUPAC Name | LCMS data |
|---|---|---|---|---|
| 1 | 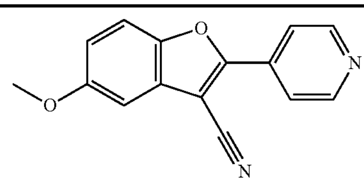 | 250.25 | 5-Methoxy-2-(pyridin-4-yl)-1-benzofuran-3-carbonitrile | Tr(MET-uHPLC-AB-101) = 1.96 min, (ES$^+$) (M + H)$^+$ 251 |
| 2 | 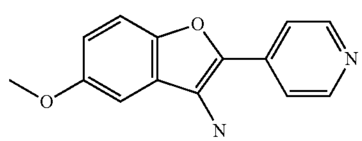 | 304.14 | 4-(3-Bromo-5-methoxy-1-benzofuran-2-yl)pyridine | Tr(MET-uHPLC-AB-101) = 2.29 min, (ES$^+$) (M + H)$^+$ 304/306 |

Method 24

Scheme for Method 24

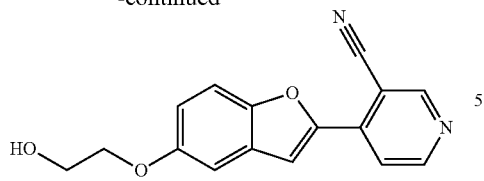

Step 1, Method 24: 4-(5-{2-[(tert-Butyldimethylsilyl)oxy]ethoxy}-1-benzofuran-2-yl)pyridine-3-carbonitrile Sodium hydride (60% in mineral oil, 14 mg, 0.36 mmol) was suspended in anhydrous N,N-dimethylformamide (0.5 mL) and cooled to 0° C. under nitrogen. 4-(5-Hydroxy-1-benzofuran-2-yl)pyridine-3-carbonitrile (80 mg, 0.34 mmol, prepared by Method 20) in anhydrous N,N-dimethylformamide (3.5 mL) was added slowly to the reaction mixture. The mixture was allowed to warm to room temperature over 30 minutes then (2-bromoethoxy)(tert-butyl)dimethylsilane (0.08 mL, 0.37 mmol) added and the reaction mixture stirred for 32 hours at room temperature then heated to 50° C. for 6 hours. Water (0.2 mL) was added and the reaction mixture partitioned between ethyl acetate (40 mL) and water (15 mL). The aqueous phase was extracted with ethyl acetate (2×20 mL) and the combined organics washed with water (2×15 mL), brine (10 mL), dried over sodium sulphate, filtered and concentrated. Purification by FCC (silica, 0-40% ethyl acetate in heptane) gave the title compound 67 mg (50% yield) as a white solid. Tr(METCR1278)=2.87 min, (ES⁺) (M+H)⁺ 395.

Step 2, Method 24: 4-[5-(2-Hydroxyethoxy)-1-benzofuran-2-yl]pyridine-3-carbonitrile 4-(5-{2-[(tert-Butyldimethylsilyl)oxy]ethoxy}-1-benzofuran-2-yl)pyridine-3-carbonitrile (67 mg, 0.17 mmol) was dissolved in tetrahydrofuran (3 mL). 3 M hydrochloric acid (0.57 mL) was added and the reaction stirred at room temperature for 1.5 hours. The reaction mixture was diluted with ethyl acetate (20 mL) and water (10 mL) and the aqueous extracted with ethyl acetate (2×20 mL). The combined organic extracts were washed with brine (5 mL), dried over sodium sulphate, filtered and concentrated. Purification by FCC (silica, 20-80% ethyl acetate in heptane) gave the title compound 25 mg (52% yield) as an off white solid.

Example 1, Method 24: 4-[5-(2-Hydroxyethoxy)-1-benzofuran-2-yl]pyridine-3-carbonitrile $\delta_H$ NMR (500 MHz, DMSO) 9.12 (s, 1H), 8.92 (d, J=5.4 Hz, 1H), 8.07 (d, J=5.4 Hz, 1H), 7.94 (s, 1H), 7.63 (d, J=9.0 Hz, 1H), 7.37 (d, J=2.6 Hz, 1H), 7.10 (dd, J=9.0, 2.6 Hz, 1H), 4.89 (s, 1H), 4.05 (t, J=5.0 Hz, 2H), 3.75 (d, J=4.3 Hz, 2H). Tr(MET-uHPLC-AB-101)=2.42 min, (ES⁺) (M+H)⁺ 281.

The following example was prepared using Method 24 described above:

TABLE 25

| Example | Structure | Mol. Weight | IUPAC Name | LCMS data |
|---|---|---|---|---|
| 1 | 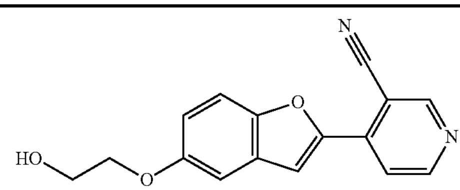 | 280.28 | 4-[5-(2-Hydroxyethoxy)-1-benzofuran-2-yl]pyridine-3-carbonitrile | Tr(MET-uHPLC-AB-101) = 2.42 min, (ES⁺) (M + H)⁺ 281 |

Method 25

Scheme for Method 25

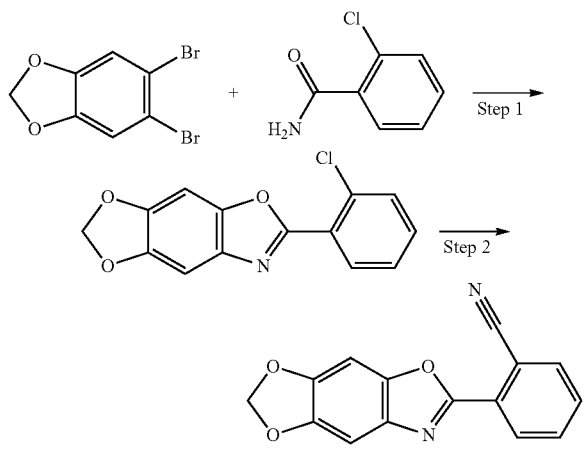

Step 1, Method 25: 11-(2-Chlorophenyl)-4,6,10-trioxa-12-azatricyclo[7.3.0.0³,⁷]dodeca-1,(9),2,7,11-tetraene A mixture of 5,6-dibromo-2H-1,3-benzodioxole (500 mg, 1.79 mmol), 2-chlorobenzamide (300 mg, 1.93 mmol), potassium carbonate (1.0 g, 7.24 mmol), N,N'-dimethylethane-1,2-diamine (50 µL, 0.57 mmol) and copper(I) iodide (35 mg, 0.18 mmol) in toluene (30 mL) and 1,4-doxane (30 mL) was stirred under reflux for 24 hours. After cooling to room temperature the mixture was diluted with ethyl acetate (50 mL), filtered and concentrated. The residue was taken up in ethyl acetate (150 mL), washed with water (50 mL) and brine (50 mL), dried over magnesium sulphate, filtered and absorbed onto a small amount of silica. Purification by FCC (silica, 0-20% ethyl acetate in heptane) and recrystallisation from 5% ethyl acetate in heptane (10 mL) gave the title compound 120 mg (25% yield) as a colourless, crystalline solid. $\delta_H$ NMR (500 MHz, DMSO) 8.09 (dd, J=7.7, 1.8 Hz, 1H), 7.69 (dd, J=7.9, 1.2 Hz, 1H), 7.59 (td, J=7.7, 1.8 Hz, 1H), 7.55 (td, J=7.5, 1.3 Hz, 1H), 7.51 (s, 1H), 7.41 (s, 1H), 6.14 (s, 2H). Tr(MET-uHPLC-AB-101)=3.66 min, (ES$^+$) (M+H)$^+$ 274.

Step 2, Method 25: 2-{4,6,10-Trioxa-12-azatricyclo[7.3.0.0$^{3,7}$]dodeca-1(9),2,7,11-tetraen-11-yl}benzonitrile A mixture of 11-(2-Chlorophenyl)-4,6,10-trioxa-12-azatricyclo[7.3.0.0$^{3,7}$]dodeca-1,(9),2,7,11-tetraene (140 mg, 0.51 mmol), zinc cyanide (310 mg, 2.64 mmol) and tetrakis(triphenylphosphine)palladium (0) (75 mg, 0.07 mmol) in N,N-dimethylacetamide (5 mL) was heated in a microwave at 200° C. for 2 hours. After cooling to room temperature the mixture was added to water (50 mL) and stirred for 30 minutes. The precipitate was collected by filtration and washed with water (50 mL). The solid was dissolved in ethyl acetate (100 mL), washed with brine (50 mL), dried over magnesium sulphate, filtered and absorbed onto a small amount of silica. Purification by FCC (silica, 0-30% ethyl acetate in heptane) gave the title compound 33 mg (25% yield) as off-white solid.

Example 1, Method 25: 2-{4,6,10-trioxa-12-azatricyclo[7.3.0.0$^{3,7}$]dodeca-1(9),2,7,11-tetraen-11-yl}benzonitrile $\delta_H$ NMR (500 MHz, DMSO) 8.31-8.23 (m, 1H), 8.11-8.02 (m, 1H), 7.90 (td, J=7.8, 1.3 Hz, 1H), 7.75 (td, J=7.7, 1.1 Hz, 1H), 7.53 (s, 1H), 7.43 (s, 1H), 6.15 (s, 2H). Tr(MET-uHPLC-AB-101)=3.19 min, (ES$^+$) (M+H)$^+$ 265.

The following example was prepared using Method 25 described above:

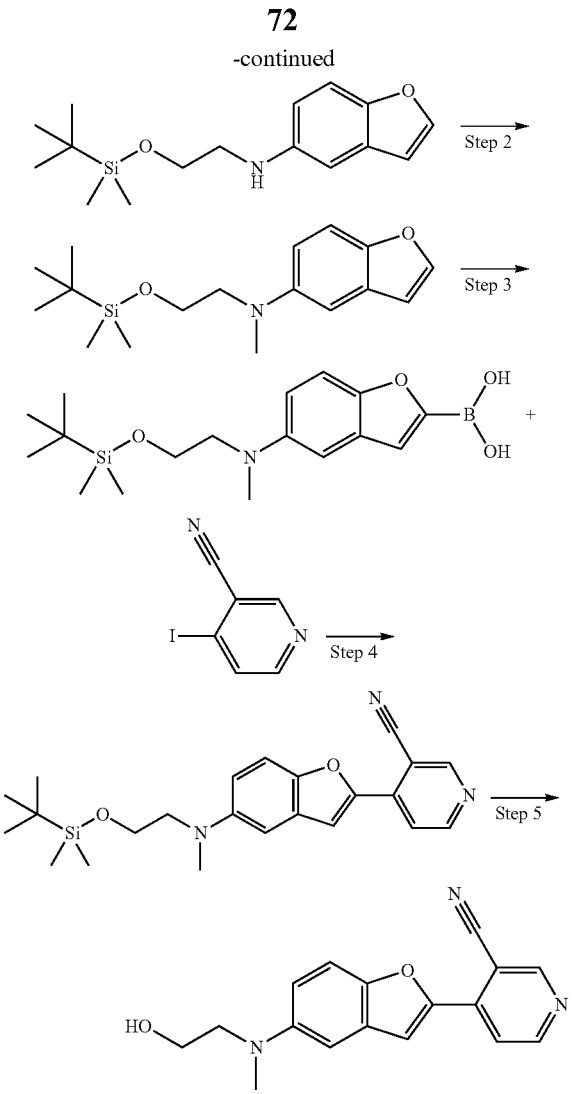

TABLE 26

| Example | Structure | Mol. Weight | IUPAC Name | LCMS data |
|---|---|---|---|---|
| 1 | 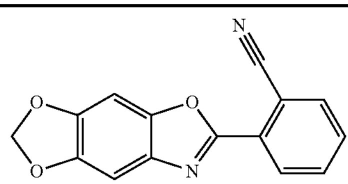 | 264.24 | 2-{4,6,10-trioxa-12-azatricyclo[7.3.0.0$^{3,7}$]dodeca-1(9),2,7,11-tetraen-11-yl}benzonitrile | Tr(MET-uHPLC-AB-101) = 3.19 min, (ES$^+$) (M + H)$^+$ 265 |

Method 26

Scheme for Method 26

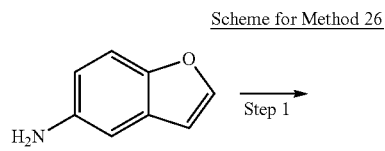

Step 1, Method 26: N-{2-[(tert-Butyldimethylsilyl)oxy]ethyl}-1-benzofuran-5-amine Sodium hydride (60% in mineral oil, 97 mg, 4.06 mmol) was suspended in anhydrous N,N-dimethylformamide (2 mL). 1-Benzofuran-5-amine (450 mg, 3.38 mmol) in N,N-dimethylformamide (3 mL) was added and the mixture stirred at 0° C. for 5 minutes. The suspension was warmed to room temperature and stirred for 30 minutes, (2-bromoethoxy)(tert-butyl)dimethylsilane (870 µL, 4.06 mmol) was added and the reaction stirred at 60° C. for 20 hours. Water (0.5 mL) was added and the reaction concentrated. The residue was purified by FCC (silica, 0-30% ethyl acetate in heptane) to give the title compound 364 mg (30% yield) as a yellow gum. $\delta_H$ NMR (500 MHz, DMSO) 7.77 (d, J=2.1 Hz, 1H), 7.28 (d, J=8.8 Hz, 1H), 6.72 (d, J=2.1 Hz, 2H), 6.64 (dd, J=8.8, 2.4 Hz, 1H), 5.24 (t, J=6.0 Hz, 1H), 3.74 (t, J=6.2 Hz, 2H), 3.15 (q, J=6.1 Hz, 2H), 0.87 (s, 9H), 0.04 (s, 6H). Tr(METCR1278)=2.38 min, (ES$^+$) (M+H)$^+$ 292, 85%.

Step 2, Method 26: N-{2-[(tert-Butyldimethylsilyl)oxy]ethyl}-N-methyl-1-benzofuran-5-amine N-{2-[(tert-Butyldimethylsilyl)oxy]ethyl}-1-benzofuran-5-amine (85%, 364 mg, 1.06 mmol) was slowly added to a suspension of sodium hydride (60% in mineral oil, 31 mg, 1.27 mmol) in anhydrous N,N-dimethylformamide (1 mL) and stirred at 0° C. for 30 minutes. Iodomethane (80 µL, 1.29 mmol) was added and the reaction warmed to room temperature and stirred overnight under nitrogen. Water (0.1 mL) was added and the reaction concentrated. The residue was partitioned between ethyl acetate (20 mL) and water (20 mL). The aqueous was extracted ethyl acetate (2×20 mL), the combined organic extracts washed with brine (10 mL), dried over sodium sulphate, filtered and concentrated. Purification by FCC (silica, 0-30% ethyl acetate in heptane) gave the title compound, 70 mg (13% yield) as a pale yellow oil. $\delta_H$ NMR (500 MHz, chloroform) 7.53 (d, J=1.8 Hz, 1H), 7.34 (d, J=9.0 Hz, 1H), 6.87 (s, 1H), 6.80 (dd, J=9.0, 2.1 Hz, 1H), 6.68-6.58 (m, 1H), 3.79 (dt, J=13.5, 6.4 Hz, 2H), 3.47 (t, J=6.2 Hz, 2H), 2.99 (s, 3H), 0.89 (s, 9H), 0.03 (s, 6H). Tr(METCR1278)=2.22 min, (ES$^+$) (M+H)$^+$ 306.

Step 3, Method 26: [5-({2-[(tert-Butyldimethylsilyl)oxy]ethyl}(methyl)amino)-1-benzofuran-2-yl]boronic acid 1.6 M n-butyllithium in hexane (0.16 mL, 0.26 mmol) was added slowly to a stirred solution of N-{2-[(tert-butyldimethylsilyl)oxy]ethyl}-N-methyl-1-benzofuran-5-amine (70 mg, 0.23 mmol) in dry tetrahydrofuran (2 mL) at −78° C. After 1 hour stirring at −78° C., triisopropylborate (0.11 mL, 0.46 mmol) was added drop-wise and the mixture stirred for 1 hour at −78° C., then at room temperature for 2 hours under nitrogen. 2 M hydrochloric acid (0.344 mL) was added and the reaction mixture stirred at room temperature for 1 hour. The reaction mixture was poured into water (5 mL) and extracted with tert-butyl methyl ether (3×20 mL). The combined organics were washed with brine (10 mL), dried over magnesium sulphate, filtered and concentrated to give the crude title compound 62 mg (58% yield) as a pale orange gum that was used directly in the next step.

Step 4, Method 26: 4-[5-({2-[(tert-Butyldimethylsilyl)oxy]ethyl}(methyl)amino)-1-benzofuran-2-yl]pyridine-3-carbonitrile

[5-({2-[(tert-Butyldimethylsilyl)oxy]ethyl}(methyl)amino)-1-benzofuran-2-yl]boronic acid (70 mg, 0.2 mmol), 4-iodopyridine-3-carbonitrile (55 mg, 0.24 mmol) and 2 M sodium carbonate (220 µL, 0.441 mmol) were suspended in N,N-dimethylformamide (3 mL) and sonicated under a flow of nitrogen for 5 minutes. Tetrakis(triphenylphosphine)palladium(0) (12 mg, 0.01 mmol) was added and the reaction heated to 70° C. for 16 hours. The reaction was cooled to room temperature and the solvents removed in vacuo. The residue was sonicated with ethyl acetate (10 mL) and filtered through a celite pad. The pad was washed with ethyl acetate (40 mL). The filtrate was diluted with water (20 mL), the aqueous extracted with ethyl acetate (2×20 mL) and the combined organic extracts washed with brine (10 mL), dried over sodium sulphate, filtered and concentrated. Purification by FCC (silica, 0-30% ethyl acetate in heptane) gave the title compound 26 mg (27% yield) as a pale yellow gum. $\delta_H$ NMR (500 MHz, chloroform) 8.88 (s, 1H), 8.77 (d, J=5.0 Hz, 1H), 7.92 (d, J=5.4 Hz, 1H), 7.84 (s, 1H), 7.39 (s, 1H), 6.95 (s, 1H), 6.86 (s, 1H), 3.80 (s, 2H), 3.49 (t, J=5.9 Hz, 2H), 3.01 (s, 3H), 0.86 (s, 9H), 0.00 (s, 6H).

Step 5, Method 26: 4-{5-[(2-Hydroxyethyl)(methyl)amino]-1-benzofuran-2-yl}pyridine-3-carbonitrile 4-[5-({2-[(tert-Butyldimethylsilyl)oxy]ethyl}(methyl)amino)-1-benzofuran-2-yl]pyridine-3-carbonitrile (85%, 26 mg, 0.05 mmol) was dissolved in tetrahydrofuran (2 mL). 3 M hydrochloric acid (0.18 mL) was added and the reaction was stirred at room temperature for 1.5 hours. The reaction mixture was diluted with ethyl acetate (20 mL) and water (10 mL), the aqueous extracted with ethyl acetate (2×20 mL), the combined organic extracts washed with brine (5 mL), dried over sodium sulphate, filtered and concentrated. Purification by FCC (silica, 20-80% ethyl acetate in heptane) gave a solid. The solid was dissolved in ethanol (1 mL) using heat and sonication and stood for 15 hours, then the supernatant decanted. The solid was triturated with heptane (1 mL) and stood for 5 minutes, then the supernatant decanted. The solid was dissolved in acetonitrile:water (1:1; 1 mL) and concentrated to give the title compound 2 mg (12% yield) as a yellow powder.

Example 1, Method 26: 4-{5-[(2-Hydroxyethyl)(methyl)amino]-1-benzofuran-2-yl}pyridine-3-carbonitrile $\delta_H$ NMR (500 MHz, DMSO) 9.08 (s, 1H), 8.89 (d, J=5.4 Hz, 1H), 8.03 (d, J=5.4 Hz, 1H), 7.85 (s, 1H), 7.52 (d, J=8.8 Hz, 1H), 7.04-6.95 (m, 2H), 4.66 (t, J=5.1 Hz, 1H), 3.58 (q, J=5.9 Hz, 2H), 3.42 (t, J=6.2 Hz, 2H), 2.96 (s, 3H). Tr(MET-uHPLC-AB-101)=1.54 min, (ES$^+$) (M+H)$^+$ 294.

The following example was prepared using Method 26 described above:

TABLE 27

| Example | Structure | Mol. Weight | IUPAC Name | LCMS data |
|---------|-----------|-------------|------------|-----------|
| 1 | 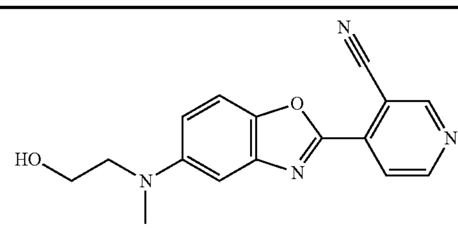 | 293.32 | 4-{5-[(2-Hydroxyethyl)(methyl)amino]-1-benzofuran-2-yl}pyridine-3-carbonitrile | Tr(MET-uHPLC-AB-101) = 1.54 min, (ES$^+$) (M + H)$^+$ 294 |

Method 27

Scheme for Method 27

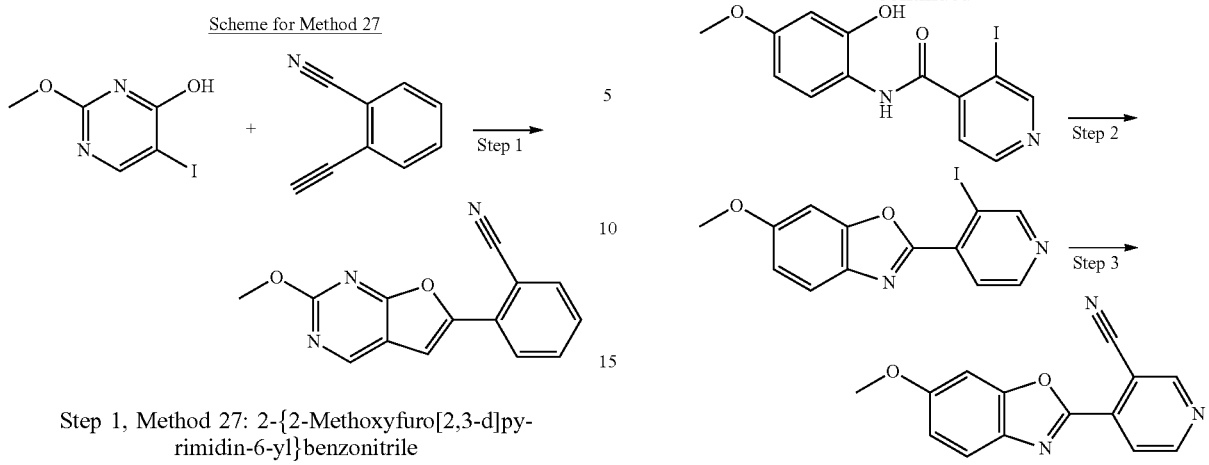

Step 1, Method 27: 2-{2-Methoxyfuro[2,3-d]py-rimidin-6-yl}benzonitrile

A mixture of 5-iodo-2-methoxypyrimidin-4-ol (100 mg, 0.4 mmol, described in WO/2008/070908), 2-ethynylbenzonitrile (76 mg, 0.6 mmol) and copper(I) iodide (22 mg, 0.11 mmol) in piperidine (1.5 mL) was stirred under a stream of nitrogen for 10 minutes. Tetrakis(triphenylphosphine)palladium(0) (46 mg, 0.04 mmol) was added and the mixture was stirred overnight at 60° C. in a sealed tube in the dark. After cooling to room temperature the volatiles were removed in vacuo. Purification by FCC (silica, 5-70% ethyl acetate in heptane) and preparative HPLC (acetonitile-water-0.2% ammonium hydroxide) followed by recrystallisation from methanol (2 mL) gave the title compound 2 mg (2% yield) as a white, crystalline solid.

Example 1, Method 27: 2-{2-Methoxyfuro[2,3-d]pyrimidin-6-yl}benzonitrile $\delta_H$ NMR (500 MHz, methanol) 8.93 (s, 1H), 8.12 (d, J=7.8 Hz, 1H), 7.91 (d, J=7.8 Hz, 1H), 7.84 (td, J=8.0, 1.2 Hz, 1H), 7.74 (s, 1H), 7.61 (td, J=7.7, 1.0 Hz, 1H), 4.10 (s, 3H). Tr(MET-uHPLC-AB-101)=2.93 min, (ES⁺) (M+H)⁺ 252.

The following example was prepared using Method 27 described above:

Step 1, Method 28: N-(2-Hydroxy-4-methoxyphenyl)-3-iodopyridine-4-carboxamide

3-Iodopyridine-4-carboxylic acid (250 mg, 1 mmol), 2-amino-5-methoxyphenol hydrochloride (194 mg, 1.1 mmol), N-ethyl-N-(propan-2-yl)propan-2-amine (521 μL, 3.01 mmol) and 1-[bis(dimethylamino)methylene]-1H-1,2,3-triazolo[4,5-b]pyridinium 3-oxide hexafluorophosphate (420 mg, 1.1 mmol) were dissolved in dichloromethane (20 mL) and N,N-dimethylformamide (2 mL) was added. The reaction was stirred at room temperature in a nitrogen atmosphere for 16 hours then heated at 50° C. for 4 hours. The reaction mixture was concentrated and the residue partitioned between dichloromethane (30 mL) and water (20 mL). The phases were separated and the aqueous phase extracted with dichloromethane (2×30 mL). The combined organic extracts were washed with brine (20 mL), dried over sodium sulphate, filtered and concentrated. Purification by FCC (silica, 20-80% ethyl acetate in heptane) gave the title compound, 85 mg (23% yield) as an off-white solid. $\delta_H$ NMR (500 MHz, DMSO) 8.96 (s, 1H), 8.61 (d, J=4.8 Hz,

TABLE 28

| Example | Structure | Mol. Weight | IUPAC Name | LCMS data |
|---|---|---|---|---|
| 1 | 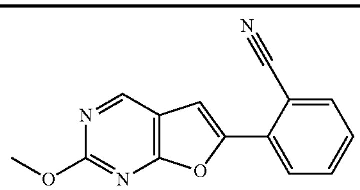 | 251.24 | 2-{2-Methoxyfuro[2,3-d]pyrimidin-6-yl}benzonitrile | Tr(MET-uHPLC-AB-101) = 2.9. min, (ES⁺) (M + H)⁺ 252 |

Method 28

1H), 7.54 (d, J=8.7 Hz, 1H), 7.51 (d, J=4.8 Hz, 1H), 6.45 (d, J=2.4 Hz, 1H), 6.40 (d, J=8.5 Hz, 1H), 3.70 (s, 3H).

Step 2, Method 28: 2-(3-Iodopyridin-4-yl)-6-methoxy-1,3-benzoxazole

Scheme for Method 28

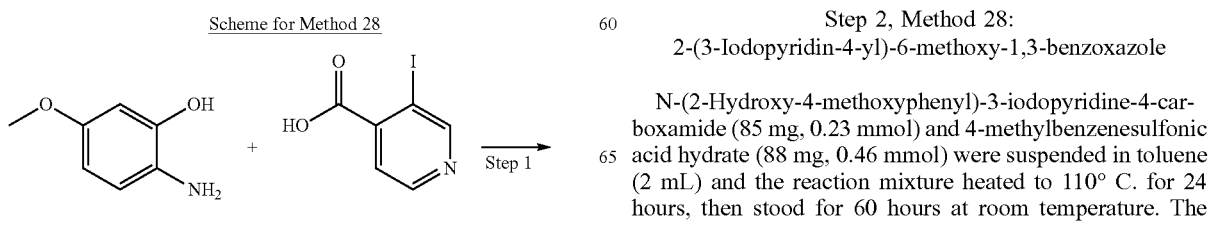

N-(2-Hydroxy-4-methoxyphenyl)-3-iodopyridine-4-carboxamide (85 mg, 0.23 mmol) and 4-methylbenzenesulfonic acid hydrate (88 mg, 0.46 mmol) were suspended in toluene (2 mL) and the reaction mixture heated to 110° C. for 24 hours, then stood for 60 hours at room temperature. The reaction was heated to 100° C. for 20 hours. The solvents were removed in vacuo and the residue partitioned between dichloromethane (50 mL) and saturated aqueous sodium bicarbonate (20 mL). Solid sodium bicarbonate was added until the pH was ~8. The aqueous was extracted with dichloromethane (2×30 mL), the combined organics dried over sodium sulphate, filtered and concentrated in vacuo. Purification by FCC (silica, 0-100% ethyl acetate in heptane) gave the title compound, 37 mg (46% yield) as a pale pink solid. $\delta_H$ NMR (250 MHz, chloroform) 9.21 (s, 1H), 8.67 (s, 1H), 8.00 (s, 1H), 7.76 (d, J=8.8 Hz, 1H), 7.15 (d, J=2.3 Hz, 1H), 7.04 (dd, J=8.8, 2.4 Hz, 1H), 3.91 (s, 3H).

Step 3, Method 28: 4-(6-Methoxy-1,3-benzoxazol-2-yl)pyridine-3-carbonitrile 2-(3-Iodopyridin-4-yl)-6-methoxy-1,3-benzoxazole (37 mg, 0.11 mmol), zinc(II) cyanide (14 mg, 0.12 mmol) and tetrakis(triphenylphosphine)palladium(0) (6 mg, 0.01 mmol) were suspended in N,N-dimethylacetamide (1 mL) and heated using microwave irradiation at 180° C. for 10 minutes. The solvents were removed in vacuo and the reaction mixture diluted with ethyl acetate (10 mL) and water (10 mL) and the aqueous extracted with ethyl acetate (2×5 mL). The combined organic extracts were washed with water (5×3 mL), brine (3 mL), dried over sodium sulphate, filtered and concentrated. Purification by FCC (silica, 20-80% ethyl acetate in heptane) gave the title compound 12.7 mg (48% yield) as a white solid.

Example 1, Method 28: 4-(6-Methoxy-1,3-benzoxazol-2-yl)pyridine-3-carbonitrile $\delta_H$ NMR (250 MHz, DMSO) 9.24 (d, J=0.7 Hz, 1H), 9.05 (d, J=5.3 Hz, 1H), 8.24 (dd, J=5.3, 0.7 Hz, 1H), 7.86 (d, J=8.9 Hz, 1H), 7.52 (d, J=2.3 Hz, 1H), 7.12 (dd, J=8.9, 2.4 Hz, 1H), 3.89 (s, 3H). Tr(MET-uHPLC-AB-101)=2.8 min, (ES$^+$) (M+H)$^+$ 252.

The following example was prepared using Method 28 described above:

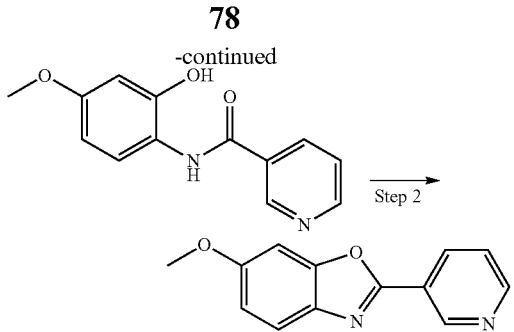

Step 1, Method 29: N-(2-Hydroxy-4-methoxyphenyl)pyridine-3-carboxamide

Nicotinoyl chloride hydrochloride (0.51 g, 2.85 mmol) was added portion-wise to a stirred solution of 2-amino-5-methoxyphenol hydrochloride (0.5 g, 2.85 mmol) in pyridine (6 mL) with ice cooling. The mixture was stirred at room temperature for 16 hours. The mixture was concentrated, the residue diluted with water (80 mL) and extracted with ethyl acetate (2×80 mL). The combined organic extracts were dried over sodium sulphate, filtered and concentrated to give the title compound 626 mg (90% yield) as a brown solid. $\delta_H$ NMR (500 MHz, DMSO) 9.72 (s, 1H), 9.63 (s, 1H), 9.11 (s, 1H), 8.74 (d, J=3.7 Hz, 1H), 8.30 (d, J=7.9 Hz, 1H), 7.54 (dd, J=7.7, 5.0 Hz, 1H), 7.36 (d, J=8.8 Hz, 1H), 6.49 (d, J=2.7 Hz, 1H), 6.43 (dd, J=8.7, 2.7 Hz, 1H), 3.72 (s, 3H). Tr(METCR1278)=1.19 min, (ES$^+$) (M+H)$^+$ 245, 84%.

Step 2, Method 29: 6-Methoxy-2-(pyridin-3-yl)-1,3-benzoxazole

N-(2-Hydroxy-4-methoxyphenyl)pyridine-3-carboxamide (70 mg, 0.29 mmol) in acetic acid (1 mL) was heated at 200° C. in a microwave for 30 minutes. The procedure was then repeated in 3 batches with N-(2-hydroxy-4-methoxy-

TABLE 29

| Example | Structure | Mol. Weight | IUPAC Name | LCMS data |
|---|---|---|---|---|
| 1 | 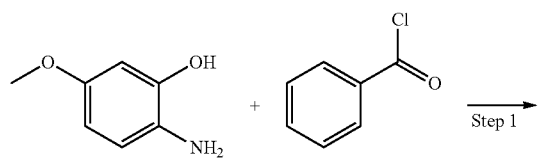 | 251.24 | 4-(6-Methoxy-1,3-benzoxazol-2-yl)pyridine-3-carbonitrile | Tr(MET-uHPLC-AB-101) = 2.8 min, (ES$^+$) (M + H)$^+$ 252 |

Method 29

Scheme for Method 29 phenyl)pyridine-3-carboxamide (3×183 mg, 2.25 mmol) in acetic acid (3×3 mL). Each mixture was heated in a microwave at 200° C. for 40 minutes. All reaction mixtures were then combined and concentrated. Purification by FCC (silica, 25-60% ethyl acetate in heptane) gave the title compound 314 mg (55% yield) as an orange powder.

Example 1, Method 29: 6-Methoxy-2-(pyridin-3-yl)-1,3-benzoxazole $\delta_H$ NMR (250 MHz, DMSO) 9.30 (dd, J=2.2, 0.8 Hz, 1H), 8.78 (dd, J=4.8, 1.6 Hz, 1H), 8.53-8.42 (m, 1H), 7.73 (d, J=8.8 Hz, 1H), 7.64 (ddd, J=8.0, 4.8, 0.9 Hz, 1H), 7.46 (d, J=2.3 Hz, 1H), 7.04 (dd, J=8.8, 2.4 Hz, 1H), 3.86 (s, 3H). Tr(MET-uHPLC-AB-101)=2.52 min, (ES⁺) (M+H)⁺ 227.

The following example was prepared using Method 29 described above:

TABLE 30

| Example | Structure | Mol. Weight | IUPAC Name | LCMS data |
|---------|-----------|-------------|------------|-----------|
| 1 | 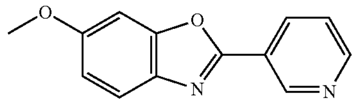 [SMILES: COc1ccc2nc(-c3cccnc3)oc2c1] | 226.23 | 6-Methoxy-2-(pyridin-3-yl)-1,3-benzoxazole | Tr(MET-uHPLC-AB-101) = 2.52 min, (ES⁺) (M + H)⁺ 227 |

Method 30

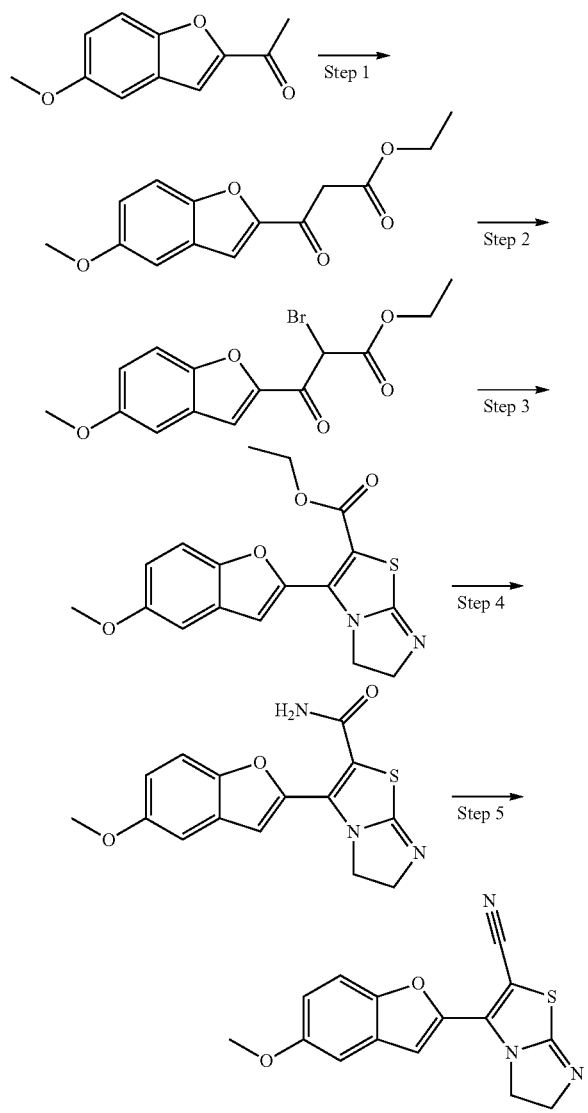

Scheme for Method 30

Step 1, Method 30: Ethyl 3-(5-methoxy-1-benzofuran-2-yl)-3-oxopropanoate

To a solution of 1-(5-methoxy-1-benzofuran-2-yl)ethan-1-one (2.0 g, 10.52 mmol) in diethyl carbonate (50 mL, 413 mmol) was added sodium hydride (60% in mineral oil, 840 mg, 21.0 mmol). After stirring for 10 minutes at room temperature the mixture was heated to 100° C. for 18 hours. The volatiles were removed in vacuo and the residue partitioned between ethyl acetate (400 mL), water (100 mL) and acetic acid (2 mL). The organic layer was separated, washed with brine (50 mL), dried over magnesium sulphate, filtered and concentrated. Purification by FCC (silica, 0-20% ethyl acetate in heptane) gave the title compound 1.85 g (67% yield) as an off-white solid. $\delta_H$ NMR (500 MHz, chloroform) 7.55-7.50 (m, 1H), 7.46 (d, J=9.0 Hz, 1H), 7.15-7.07 (m, 2H), 4.22 (q, J=7.1 Hz, 2H), 3.96 (s, 2H), 3.86 (s, 3H), 1.26 (t, J=7.1 Hz, 3H). Tr(METCR1278)=1.87 min, (ES⁺) (M+H)⁺ 263.

Step 2, Method 30: Ethyl 2-bromo-3-(5-methoxy-1-benzofuran-2-yl)-3-oxopropanoate To a solution of ethyl 3-(5-methoxy-1-benzofuran-2-yl)-3-oxopropanoate (1.5 g, 5.72 mmol) in tetrahydrofuran (100 mL) was added phenyltrimethylammonium tribromide (2.24 g, 5.96 mmol) and the mixture stirred at room temperature for 18 hours. After dilution with ethyl acetate (100 mL) the mixture was filtered and the filtrate concentrated in vacuo. The residue was taken up in ethyl acetate (200 mL), washed with 10% aqueous sodium thiosulphate (50 mL) and brine (50 mL), dried over magnesium sulphate, filtered and absorbed onto a small amount of silica. Purification by FCC (silica, 0-20% ethyl acetate in heptane) gave the title compound 1.65 g (85% yield) as a yellow oil. $\delta_H$ NMR (250 MHz, DMSO) 8.07 (d, J=0.8 Hz, 1H), 7.67 (d, J=9.1 Hz, 1H), 7.37 (d, J=2.5 Hz, 1H), 7.22 (dd, J=9.1, 2.7 Hz, 1H), 6.47 (s, 1H), 4.23 (q, J=7.1 Hz, 2H), 3.83 (s, 3H), 1.17 (t, J=7.1 Hz, 3H). Tr(METCR1278)=2.05 min, (ES⁺) (M+H)⁺ 341/343.

Step 3, Method 30: Ethyl 3-(5-methoxy-1-benzofuran-2-yl)-5H,6H-imidazo[2,1-b][1,3]thiazole-2-carboxylate hydrobromide A mixture of ethyl 2-bromo-3-(5-methoxy-1-benzofuran-2-yl)-3-oxopropanoate (1.62 g, 4.75 mmol) and imidazolidine-2-thione (485 mg, 4.75 mmol) in ethanol (20 mL) and acetic acid (10 mL) was stirred under reflux for 12 hours. The solvent was removed in vacuo and the residue triturated with a mixture of ethyl acetate and acetonitrile (10 mL, 1:1). The material was collected by filtration and dried under high vacuum to give the title compound 1.48 g (73% yield) as an off-white solid. $\delta_H$ NMR (250 MHz, DMSO) 10.07 (s, 1H), 8.05 (d, J=0.9 Hz, 1H), 7.63 (d, J=9.0 Hz, 1H), 7.36 (d, J=2.5 Hz, 1H), 7.13 (dd, J=9.1, 2.7 Hz, 1H), 4.74 (dd, J=11.1, 7.9 Hz, 2H), 4.40-4.24 (m, 4H), 3.82 (s, 3H), 1.27 (t, J=7.1 Hz, 3H). Tr(MET-uHPLC-AB-101)=1.97 min, (ES⁺) (M+H)⁺ 345.

Step 4, Method 30: 3-(5-Methoxy-1-benzofuran-2-yl)-5H,6H-imidazo[2,1-b][1,3]thiazole-2-carboxamide A solution of ethyl 3-(5-methoxy-1-benzofuran-2-yl)-5H,6H-imidazo[2,1-b][1,3]thiazole-2-carboxylate hydrobromide (100 mg, 0.29 mmol) in 7 M ammonia in methanol (6 mL) and tetrahydrofuran (2 mL) was stirred in a pressure tube at 80° C. for 3 days. After cooling to room temperature the volatiles were removed in vacuo and the residue taken up in tetrahydrofuran and absorbed onto a small amount of silica. Purification by FCC (silica, 0-10% methanol in dichloromethane) gave the title compound 24 mg (26% yield) as a yellow solid. $\delta_H$ NMR (500 MHz, DMSO) 7.55 (d, J=9.0 Hz, 1H), 7.52 (d, J=0.7 Hz, 1H), 7.33 (br. s, 2H), 7.24 (d, J=2.6 Hz, 1H), 7.01 (dd, J=9.0, 2.6 Hz, 1H), 4.09 (dd, J=9.7, 6.3 Hz, 2H), 4.02 (dd, J=9.6, 6.3 Hz, 2H), 3.80 (s, 3H). Tr(MET-uHPLC-AB-101)=1.23 min, (ES$^+$) (M+H)$^+$ 316.

Step 5, Method 30: 3-(5-Methoxy-1-benzofuran-2-yl)-5H,6H-imidazo[2,1-b][1,3]thiazole-2-carbonitrile To a solution of 3-(5-methoxy-1-benzofuran-2-yl)-5H,6H-imidazo[2,1-b][1,3]thiazole-2-carboxamide (73 mg, 0.23 mmol) and pyridine (50 µL, 0.62 mmol) in tetrahydrofuran (10 mL) at 0° C. was added trifluoroacetic anhydride (150 µL, 1.06 mmol). After stirring for 5 minutes the mixture was added to saturated aqueous sodium bicarbonate and extracted with ethyl acetate (3×50 mL). The combined organic extracts were washed with brine (50 mL), dried over magnesium sulphate, filtered and absorbed onto a small amount of silica. Purification by FCC (silica, 0-5% methanol in dichloromethane) followed by trituration with ethyl acetate (5 mL) gave the title compound 21 mg (31% yield) as a yellow solid.

Example 1, Method 30: 3-(5-Methoxy-1-benzofuran-2-yl)-5H,6H-imidazo[2,1-b][1,3]thiazole-2-carbonitrile $\delta_H$ NMR (500 MHz, DMSO) 7.62 (s, 1H), 7.60 (d, J=9.1 Hz, 1H), 7.30 (d, J=2.6 Hz, 1H), 7.09 (dd, J=9.0, 2.6 Hz, 1H), 4.35-4.18 (m, 4H), 3.81 (s, 3H). Tr(MET-uHPLC-AB-101)=1.61 min, (ES$^+$) (M+H)$^+$ 298.

The following example was prepared using Method 30 described above:

Method 31

Scheme for Method 31

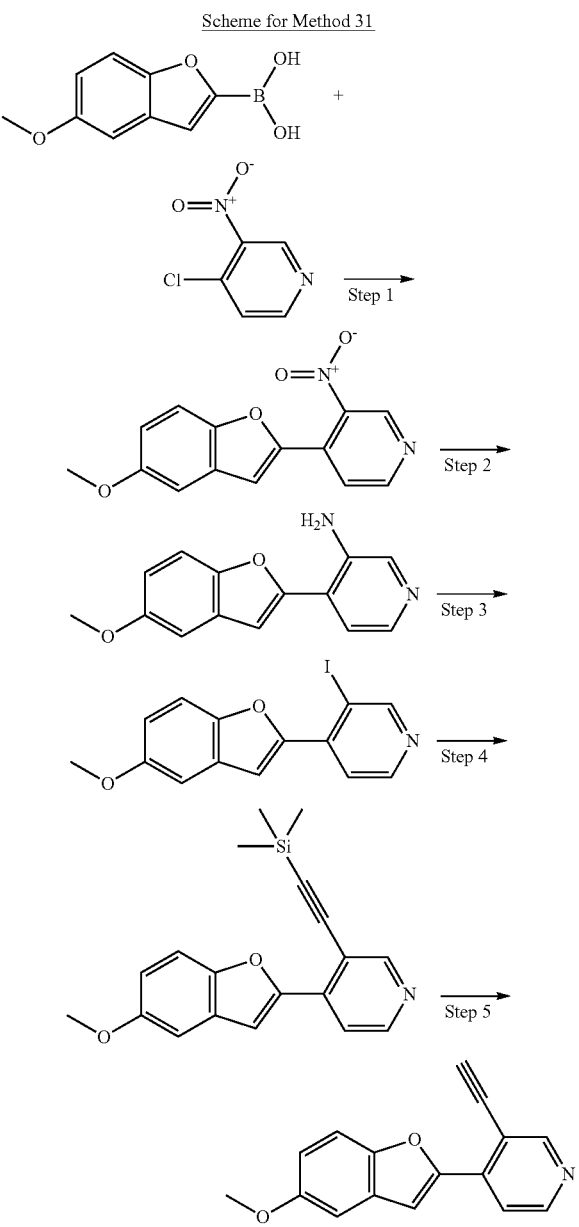

TABLE 31

| Example | Structure | Mol. Weight | IUPAC Name | LCMS data |
|---------|-----------|-------------|------------|-----------|
| 1 | 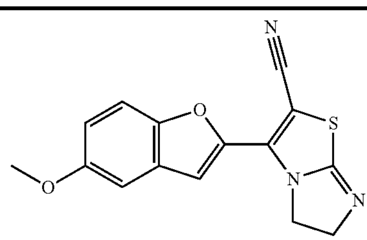 | 297.33 | 3-(5-Methoxy-1-benzofuran-2-yl)-5H,6H-imidazo[2,1-b][1,3]thiazole-2-carbonitrile | Tr(MET-uHPLC-AB-101) = 1.61 min, (ES$^+$) (M + H)$^+$ 298 |

Step 1, Method 31:
4-(5-Methoxy-1-benzofuran-2-yl)-3-nitropyridine (5-Methoxy-1-benzofuran-2-yl)boronic acid (200 mg, 0.99 mmol, prepared by Method 3) and 4-chloro-3-nitropyridine (95%, 182 mg, 1.09 mmol) were suspended in anhydrous 1,4-dioxane (10 mL), 2 M sodium carbonate (1 mL) was added and the mixture sonicated under a flow of nitrogen for 5 minutes. Tetrakis(triphenylphosphine)palladium(0) (57 mg, 0.05 mmol) was added and the reaction heated to 70° C. for 16 hours. The reaction was cooled to room temperature and concentrated. The residue was partitioned between ethyl acetate and water (1:1; 100 mL) and passed through a celite pad, eluting with ethyl acetate (20 mL). The layers were separated and the aqueous extracted with ethyl acetate (2×30 mL). The combined organic extracts were washed with brine (10 mL), dried over sodium sulphate, filtered and concentrated. Purification by FCC (silica, 0-65% ethyl acetate in heptane) gave the title compound 166 mg (61% yield) as a yellow powder. $\delta_H$ NMR (500 MHz, chloroform) 8.95 (s, 1H), 8.82 (s, 1H), 7.88 (d, J=5.0 Hz, 1H), 7.43 (d, J=9.0 Hz, 1H), 7.24 (d, J=0.7 Hz, 1H), 7.07 (d, J=2.5 Hz, 1H), 7.03 (dd, J=9.0, 2.6 Hz, 1H), 3.86 (s, 3H).

Step 2, Method 31:
4-(5-Methoxy-1-benzofuran-2-yl)pyridin-3-amine 4-(5-Methoxy-1-benzofuran-2-yl)-3-nitropyridine (160 mg, 0.59 mmol) and ammonium formate (146 mg, 2.37 mmol) were suspended in ethanol (25 mL). 10% Palladium on carbon (95 mg, 0.09 mmol) was added portion-wise and the reaction mixture stirred at room temperature in a nitrogen atmosphere for 16 hours then heated to 80° C. for 24 hours. The reaction mixture was cooled to room temperature, filtered through celite and concentrated. The residue was suspended in ethanol (25 mL), ammonium formate (146 mg, 2.37 mmol) and 10% palladium on carbon (95 mg, 0.09 mmol) were added and the reaction heated to reflux for 2 hours under a nitrogen atmosphere. The reaction was cooled to room temperature, filtered through a celite pad and concentrated. Purification by SCX gave the title compound 110 mg (72% yield) as a beige powder. Tr(METCR1278)=1.29 min, (ES$^+$) (M+H)$^+$ 241.

Step 3, Method 31:
3-Iodo-4-(5-methoxy-1-benzofuran-2-yl)pyridine 4-(5-Methoxy-1-benzofuran-2-yl)pyridin-3-amine (254 mg, 1.06 mmol) was suspended in diiodomethane (3 mL, 37 mmol) and tetrahydrofuran (3 mL) and stirred for 1 minute at room temperature. 3-methylbutyl nitrite (3 mL, 22.33 mmol) was added slowly and the reaction mixture heated to 80° C. for 2 hours in a sealed tube. The solvents were removed in vacuo. The residue was dissolved in dichloromethane (2 mL) and loaded onto a heptane-equilibrated silica pad. The pad was eluted with heptane (6 column volumes), then flushed with ethyl acetate. The ethyl acetate flush was concentrated. Purification by FCC (silica, 0-40% ethyl acetate in heptane) gave the title compound, 200 mg (52% yield) as a pale orange solid. Tr(METCR1278)=2.26 min, (ES$^+$) (M+H)$^+$ 352, 90%.

Step 4, Method 31: 4-(5-Methoxy-1-benzofuran-2-yl)-3-[2-(trimethylsilyl)ethynyl]pyridine 3-Iodo-4-(5-methoxy-1-benzofuran-2-yl)pyridine (90%, 100 mg, 0.26 mmol), bis(triphenylphosphine)palladium(II) dichloride (9 mg, 0.01 mmol) and copper(I) iodide (5 mg, 0.03 mmol) were suspended in diisopropylethylamine (3 mL). Ethynyl(trimethyl)silane (40 μL, 0.28 mmol) was added and the reaction mixture heated to 70° C. for 6 hours, then stood at room temperature overnight. The reaction mixture was concentrated and purified by FCC (silica, 0-40% ethyl acetate in heptane) to give the title compound, 81 mg (94% yield) as an orange glass. Tr(METCR1278) =2.67 min, (ES$^+$) (M+H)$^+$ 322.

Step 5, Method 31:
3-Ethynyl-4-(5-methoxy-1-benzofuran-2-yl)pyridine 4-(5-Methoxy-1-benzofuran-2-yl)-3-[2-(trimethylsilyl)ethynyl]pyridine (81 mg, 0.25 mmol) and potassium carbonate (70 mg, 0.5 mmol) were suspended in ethanol (2 mL) at room temperature for 5 minutes. The solvents were removed in vacuo and the solid partitioned between ethyl acetate (10 mL) and water (10 mL). The layers were separated and the aqueous extracted with ethyl acetate (2×10 mL). The combined organic extracts were washed with brine (10 mL), dried over sodium sulphate, filtered and concentrated. Trituration with ethanol and FCC (silica, 0-40% ethyl acetate in heptane) gave the title compound 6.9 mg (11% yield) as an off-white solid.

Example 1, Method 31:
3-Ethynyl-4-(5-methoxy-1-benzofuran-2-yl)pyridine $\delta_H$ NMR (500 MHz, chloroform) 8.81 (s, 1H), 8.62 (d, J=5.4 Hz, 1H), 8.06-7.85 (m, 1H), 7.89 (d, J=5.4 Hz, 1H), 7.44 (d, J=9.0 Hz, 1H), 7.10 (d, J=2.6 Hz, 1H), 7.00 (dd, J=9.0, 2.6 Hz, 1H), 3.87 (s, 3H), 3.66 (s, 1H). Tr(MET-uHPLC-AB-101)=3.36 min, (ES$^+$) (M+H)$^+$ 250.

The following examples were prepared using Method 31 described above:

TABLE 32

| Example | Structure | Mol. Weight | IUPAC Name | LCMS data |
|---|---|---|---|---|
| 1 | 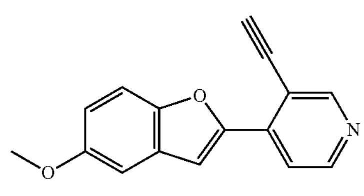 [SMILES: C#Cc1cnccc1-c1cc2cc(OC)ccc2o1] | 249.26 | 3-Ethynyl-4-(5-methoxy-1-benzofuran-2-yl)pyridine | Tr(MET-uHPLC-AB-101) = 3.36 min, (ES$^+$) (M + H)$^+$ 250 |

TABLE 32-continued

| Example | Structure | Mol. Weight | IUPAC Name | LCMS data |
|---|---|---|---|---|
| 2 | 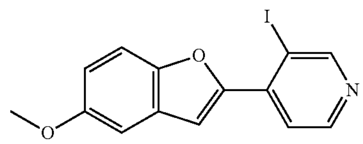 [SMILES: COc1ccc2oc(-c3ccncc3I)cc2c1] | 351.14 | 3-Iodo-4-(5-methoxy-1-benzofuran-2-yl)pyridine | Tr(MET-uHPLC-AB-101) = 3.8 min, (ES$^+$) (M + H)$^+$ 352 |

Method 32

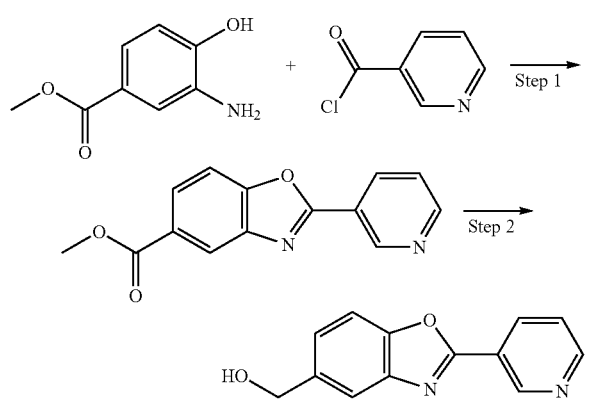

Scheme for Method 32

Step 1, Method 32: Methyl 2-(pyridin-3-yl)-1,3-benzoxazole-5-carboxylate

Methyl 3-amino-4-hydroxybenzoate (200 mg, 1.2 mmol) was suspended in 1,4-dioxane (3 mL), pyridine-3-carbonyl chloride hydrochloride (234 mg, 1.32 mmol) was added and the mixture heated to 200° C. in a microwave for 15 minutes. This procedure was performed 5 times. All reaction mixtures were combined then partitioned between ethyl acetate (100 mL) and saturated aqueous sodium bicarbonate (80 mL). The organic extract was dried over sodium sulphate, filtered and concentrated. Purification by FCC (silica, 20-100% ethyl acetate in heptane) gave the title compound 560 mg (37% yield) as a light brown solid. $\delta_H$ NMR (500 MHz, DMSO) 9.37 (d, J=1.7 Hz, 1H), 8.84 (dd, J=4.8, 1.6 Hz, 1H), 8.56 (dt, J=8.0, 1.9 Hz, 1H), 8.37 (d, J=1.4 Hz, 1H), 8.09 (dd, J=8.6, 1.7 Hz, 1H), 7.97 (d, J=8.6 Hz, 1H), 7.68 (ddd, J=8.0, 4.8, 0.7 Hz, 1H), 3.91 (s, 3H). Tr(METCR1278)=1.74 min, (ES$^+$) (M+H)$^+$ 255.

Step 2, Method 32: [2-(Pyridin-3-yl)-1,3-benzoxazol-5-yl]methanol

Lithium aluminum hydride (4 M in tetrahydrofuran, 0.25 mL, 1.00 mmol) was added to a stirred solution of methyl 2-(pyridin-3-yl)-1,3-benzoxazole-5-carboxylate (340 mg, 1.34 mmol) in anhydrous tetrahydrofuran (12 mL) under nitrogen. The mixture was stirred at 0° C. for 30 minutes. The mixture was quenched by cautious addition of water (1 mL) followed by saturated ammonium chloride solution (0.5 mL). The mixture was stirred at 0° C. for 20 minutes. The mixture was diluted with water (15 mL) and extracted with ethyl acetate (2×15 mL). The organic extracts were dried over sodium sulphate, filtered and concentrated. Purification by FCC (silica, 0-15% methanol in dichloromethane) gave the title compound 197 mg (65% yield) as an off-white solid.

Example 1, Method 32: [2-(Pyridin-3-yl)-1,3-benzoxazol-5-yl]methanol $\delta_H$ NMR (500 MHz, DMSO) 9.35 (d, J=1.6 Hz, 1H), 8.81 (dd, J=4.8, 1.6 Hz, 1H), 8.54 (dt, J=8.0, 1.9 Hz, 1H), 7.77 (d, J=8.3 Hz, 2H), 7.66 (ddd, J=8.0, 4.8, 0.7 Hz, 1H), 7.46-7.40 (m, 1H), 5.35 (t, J=5.7 Hz, 1H), 4.63 (d, J=5.5 Hz, 2H); Tr(MET-uHPLC-AB-101)=1.7 min, (ES$^+$) (M+H)$^+$ 227.

The following examples were prepared using Method 32 described above:

TABLE 33

| Example | Structure | Mol. Weight | IUPAC Name | LCMS data |
|---|---|---|---|---|
| 1 | 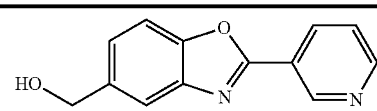 | 226.23 | [2-(Pyridin-3-yl)-1,3-benzoxazol-5-yl]methanol | Tr(MET-uHPLC-AB-101) = 1.7 min, (ES$^+$) (M + H)$^+$ 227 |

Method 33

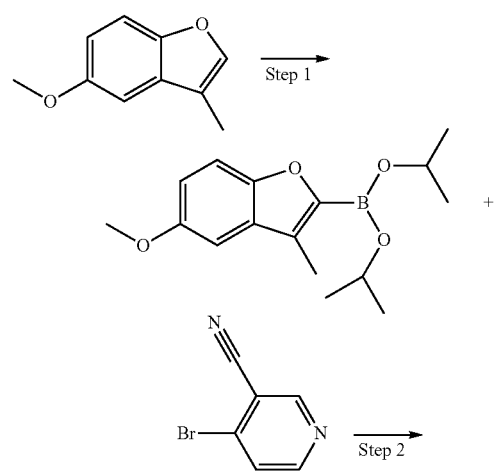

Scheme for Method 33

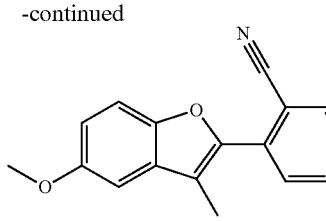

Method 34

Scheme for Method 34

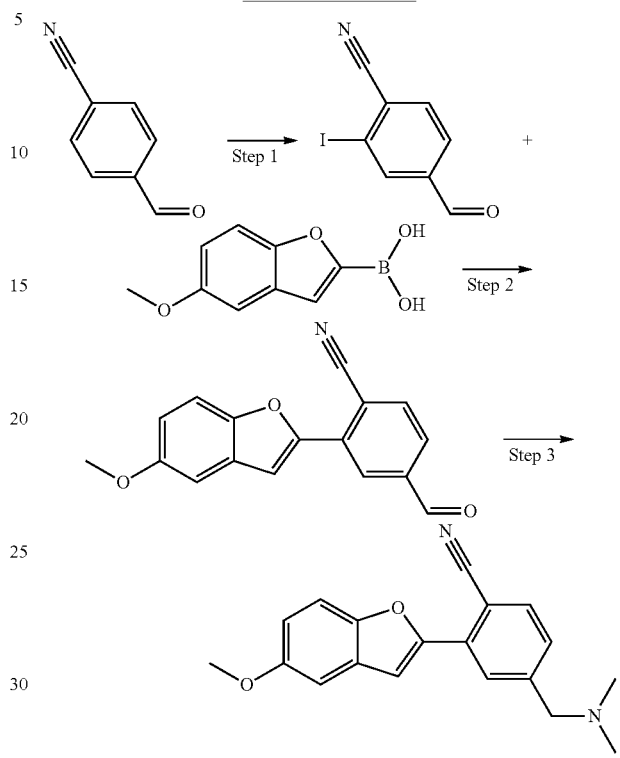

Step 1, Method 33: bis(Propan-2-yl) (5-methoxy-3-methyl-1-benzofuran-2-yl)boronate 1.6 M n-Butyllithium in hexanes (0.87 mL, 1.4 mmol) was added drop-wise to a solution of 5-methoxy-3-methyl-1-benzofuran (150 mg, 0.92 mmol) in anhydrous tetrahydrofuran (5 mL) at −78° C. The resulting mixture was stirred at −78° C. for 20 minutes and treated with triisopropyl borate (0.32 mL, 1.39 mmol). The reaction mixture was allowed to warm up slowly to room temperature and stirred overnight. The mixture was used directly in the next step.

Step 2, Method 33: 4-(5-Methoxy-3-methyl-1-benzofuran-2-yl)pyridine-3-carbonitrile Bis(propan-2-yl) (5-methoxy-3-methyl-1-benzofuran-2-yl)boronate (268 mg, 0.92 mmol) as a solution in tetrahydrofuran, 4-bromopyridine-3-carbonitrile (203 mg, 1.11 mmol) and 2 M sodium carbonate (1.02 mL, 2.03 mmol) were suspended in anhydrous N,N-dimethylformamide (5 mL) and stirred under a flow of nitrogen for 5 minutes. Tetrakis(triphenylphosphine)palladium(0) (53 mg, 0.05 mmol) was added and the reaction was heated to 70° C. for 16 hours in a sealed tube. The mixture was cooled to room temperature, water (5 mL) was added and the mixture stirred for 5 minutes. The mixture was filtered and the solid washed with water (10 mL), methanol (5 mL) and heptane (10 mL) and dried in a vacuum oven at 40° C. to give the title compound 165 mg (68% yield) as a white crystalline solid.

Example 1, Method 33: 4-(5-Methoxy-3-methyl-1-benzofuran-2-yl)pyridine-3-carbonitrile $\delta_H$ NMR (500 MHz, DMSO) 9.15 (s, 1H), 8.94 (d, J=5.3 Hz, 1H), 7.88 (d, J=5.3 Hz, 1H), 7.57 (d, J=8.9 Hz, 1H), 7.29 (d, J=2.5 Hz, 1H), 7.06 (dd, J=9.0, 2.6 Hz, 1H), 3.85 (s, 3H), 2.46 (s, 3H). Tr(MET-uHPLC-AB-101)=3.23 min, (ES$^+$) (M+H)$^+$ 265.

The following example was prepared using Method 33 described above:

Step 1, Method 34: 4-Formyl-2-iodobenzonitrile

4-Formylbenzonitrile (2 g, 15.25 mmol), N-iodosuccinimide (3.77 g, 16.78 mmol), palladium(II) acetate (0.34 g, 1.53 mmol) and 4-methylbenzenesulfonic acid hydrate (1.45 g, 7.63 mmol) were suspended in anhydrous 1,2-dichloroethane (30 mL) and the reaction mixture was heated in a sealed tube at 70° C. for 16 hours. The reaction mixture was cooled to room temperature and filtered through a celite pad, eluting with dichloromethane (3×20 mL) and the filtrate was concentrated. Purification by FCC (silica, 0-25% ethyl acetate in heptane) gave the title compound 160 mg (4% yield) as a white solid. Tr(METCR1278)=1.73 min, no ionisation.

Step 2, Method 34: 4-Formyl-2-(5-methoxy-1-benzofuran-2-yl)benzonitrile

5-Methoxy benzofuran 2-boronic acid (115 mg, 0.57 mmol, prepared by Method 3), 4-formyl-2-iodobenzonitrile

TABLE 34

| Example | Structure | Mol. Weight | IUPAC Name | LCMS data |
|---|---|---|---|---|
| 1 | 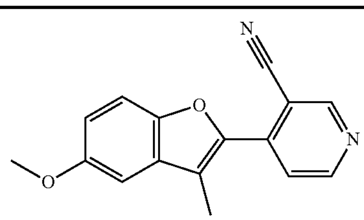 | 264.28 | 4-(5-Methoxy-3-methyl-1-benzofuran-2-yl)pyridine-3-carbonitrile | Tr(MET-uHPLC-AB-101) = 3.23 min, (ES$^+$) (M + H)$^+$ 265 |

(161 mg, 0.63 mmol) and 2 M sodium carbonate (0.57 mL, 1.14 mmol) were suspended in anhydrous N,N-dimethylformamide (5 mL) and sonicated under a flow of nitrogen for 5 minutes. Tetrakis(triphenylphosphine)palladium(0) (33 mg, 0.03 mmol) was added and the reaction heated to 70° C. for 16 hours. The mixture was cooled to room temperature and the solvents removed in vacuo. The residue was partitioned between ethyl acetate and water (1:1; 100 mL) and the aqueous layer extracted with ethyl acetate (2×30 mL). The combined organic extracts were washed with brine (20 mL), dried over sodium sulphate, filtered and concentrated. Purification by FCC (silica, 0-30% ethyl acetate in heptane) gave the title compound 100 mg (55% yield) as a yellow powder. Tr(METCR1278)=2.21 min, (ES⁺) (M+H)⁺ 278.

Step 3, Method 34: 4-[(Dimethylamino)methyl]-2-(5-methoxy-1-benzofuran-2-yl)benzonitrile 4-Formyl-2-(5-methoxy-1-benzofuran-2-yl)benzonitrile (100 mg 0.36 mmol) was dissolved in dichloromethane (5 mL) and 5.6 M dimethylamine in ethanol (77.28 μL, 0.43 mmol) added and stirred for 5 minutes. Sodium tricetoxyborohydride (115 mg, 0.54 mmol) was added and the reaction stirred for 4 hours at room temperature in a nitrogen atmosphere. The reaction was diluted with dichloromethane (10 mL) and saturated aqueous sodium bicarbonate (20 mL) and the aqueous layer extracted with dichloromethane (3×10 mL). The combined organic extracts were washed with brine (2×10 mL), dried over sodium sulphate, filtered and concentrated. Purification by preparative HPLC (acetonitrile-water-0.2% ammonium hydroxide) gave the title compound 28.5 mg (26% yield) as a yellow gum.

Example 1, Method 34: 4-[(Dimethylamino)methyl]-2-(5-methoxy-1-benzofuran-2-yl)benzonitrile $\delta_H$ NMR (500 MHz, chloroform) 8.07-7.98 (m, 1H), 7.71 (d, J=7.9 Hz, 1H), 7.66 (s, 1H), 7.44 (d, J=8.9 Hz, 1H), 7.39 (dd, J=7.9, 1.2 Hz, 1H), 7.09 (d, J=2.6 Hz, 1H), 6.96 (dd, J=8.9, 2.6 Hz, 1H), 3.87 (s, 3H), 3.54 (s, 2H), 2.30 (s, 6H). Tr(MET-uHPLC-AB-101)=1.88 min, (ES⁺) (M+H)⁺ 307.

The following example was prepared using Method 34 described above:

Step 1, Method 35: 2-Bromo-6-(5-methoxy-1-benzofuran-2-yl)benzonitrile

A mixture of (5-methoxy-1-benzofuran-2-yl)boronic acid (156 mg, 0.813 mmol, prepared by Method 3), 2-bromo-6-iodobenzonitrile (250 mg, 0.81 mmol) and 2 M sodium carbonate (0.82 mL, 1.64 mmol) in N,N-dimethylformamide (10 mL) was sonicated under a stream of nitrogen for 20 minutes. [1,1'-Bis(diphenylphosphino)ferrocene]dichloropalladium(II) complex with dichloromethane (50 mg, 0.14 mmol) was added and the mixture stirred at 70° C. for 2 hours. After cooling the mixture was added to water (100 mL) and brine (100 mL). The mixture was extracted with ethyl acetate (3×100 mL), the combined extracts were washed with brine (50 mL), dried over magnesium sulphate, filtered and concentrated. Purification by FCC (silica, 0-50%

TABLE 35

| Example | Structure | Mol. Weight | IUPAC Name | LCMS data |
|---|---|---|---|---|
| 1 | 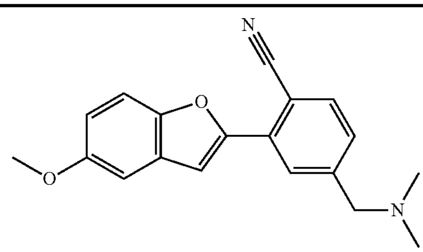 | 306.36 | 4-[(Dimethylamino)methyl]-2-(5-methoxy-1-benzofuran-2-yl)benzonitrile | Tr(MET-uHPLC-AB-101) = 1.88 min, (ES⁺) (M + H)⁺ 307 |

Method 35

Scheme for Method 35

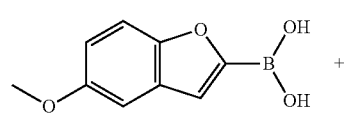

ethyl acetate in heptane) gave the title compound 168 mg (37% yield, 82% pure by LCMS) as an off-white solid, which was taken on directly into the next step. A sample was purified by preparative HPLC (acetonitrile-water-0.1% formic acid). $\delta_H$ NMR (500 MHz, DMSO) 8.09 (d, J=8.0 Hz, 1H), 7.93 (d, J=8.0 Hz, 1H), 7.76 (t, J=8.1 Hz, 1H), 7.70 (s, 1H), 7.58 (d, J=9.0 Hz, 1H), 7.32 (d, J=2.6 Hz, 1H), 7.02 (dd, J=9.0, 2.6 Hz, 1H), 3.81 (s, 3H). Tr(MET-uHPLC-AB-101)=5.45 min, (ES⁺) (M+H)⁺ 328/330.

Step 2, Method 35: 2-[(Dimethylamino)methyl]-6-(5-methoxy-1-benzofuran-2-yl)benzonitrile A mixture of 2-bromo-6-(5-methoxy-1-benzofuran-2-yl)benzonitrile (82%, 120 mg, 0.3 mmol), potassium [(dimethylamino)methyl](trifluoro)borate (60 mg, 0.36 mmol), caesium carbonate (300 mg, 0.92 mmol) and dicyclohexyl[2,4,6-tri(propan-2-yl)phenyl]phosphane (60 mg, 0.15 mmol) in tetrahydrofuran (3 mL) and water (0.3 mL) was sonicated under a stream of nitrogen for 20 minutes. Palladium(II) acetate (20 mg, 0.09 mmol) was added and the mixture stirred at 80° C. for 18 hours. After cooling to room temperature the mixture was added to water (100 mL) and extracted with ethyl acetate (3×100 mL). The combined organic extracts were washed with brine (50 mL), dried over magnesium sulphate, filtered and absorbed onto a small amount of silica. Purification by FCC (silica, 0-100% ethyl acetate in heptane) gave title compound 28 mg (31% yield) as an off-white, crystalline solid.

Example 1, Method 35: 2-[(Dimethylamino)methyl]-6-(5-methoxy-1-benzofuran-2-yl)benzonitrile $\delta_H$ NMR (500 MHz, DMSO) 7.99 (d, J=7.8 Hz, 1H), 7.80 (t, J=7.8 Hz, 1H), 7.65 (s, 1H), 7.61 (d, J=7.6 Hz, 1H), 7.57 (d, J=9.0 Hz, 1H), 7.31 (d, J=2.6 Hz, 1H), 7.00 (dd, J=8.9, 2.6 Hz, 1H), 3.81 (s, 3H), 3.64 (s, 2H), 2.23 (s, 6H). Tr(MET-uHPLC-AB-101)=1.89 min, (ES$^+$) (M+H)$^+$ 307.

The following examples were prepared using Method 35 described above:

Method 36

Scheme for Method 36:

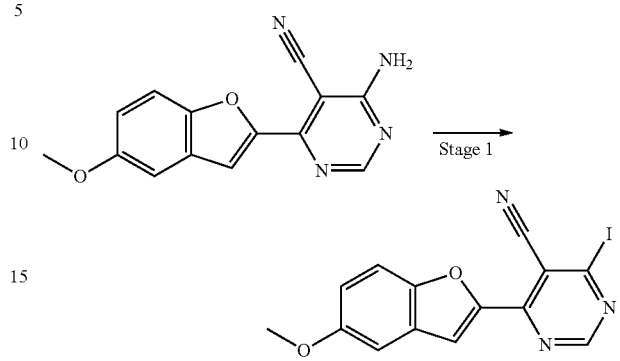

Step 1, Method 36: 4-Iodo-6-(5-methoxy-1-benzofuran-2-yl)pyrimidine-5-carbonitrile 4-Amino-6-(5-methoxy-1-benzofuran-2-yl)pyrimidine-5-carbonitrile (80%, 50 mg, 0.15 mmol, prepared by Method 3) was suspended in diiodomethane (0.5 mL, 6.21 mmol) and tetrahydrofuran (0.5 mL). After stirring for 1 minute at room temperature, 3-methylbutyl nitrite (0.5 mL, 3.72 mmol) was added and the mixture heated to 80° C. in a sealed tube for 5 hours. The reaction mixture was diluted with dichloromethane (10 mL) and concentrated to dryness. The residue was dissolved in dichloromethane (10 mL) and

TABLE 36

| Example | Structure | Mol. Weight | IUPAC Name | LCMS data |
|---|---|---|---|---|
| 1 | 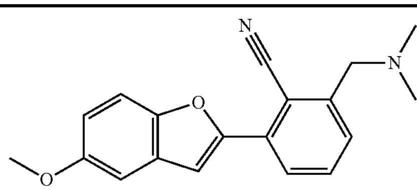 | 306.36 | 2-[(Dimethylamino)methyl]-6-(5-methoxy-1-benzofuran-2-yl)benzonitrile | Tr(MET-uHPLC-AB-101) = 1.89 min, (ES$^+$) (M + H)$^+$ 307 |
| 2 | 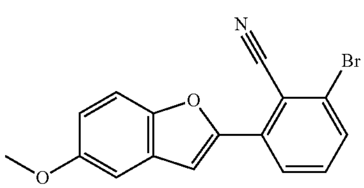 | 328.16 | 2-Bromo-6-(5-methoxy-1-benzofuran-2-yl)benzonitrile | Tr(MET-uHPLC-AB-101) = 5.45 min, (ES$^+$) (M + H)$^+$ 328/330 |
| 3 | | 328.16 | 5-Bromo-2-(5-methoxy-1-benzofuran-2-yl)benzonitrile | Tr(MET-uHPLC-AB-101) = 4.4 min, (ES$^+$) (M + H)$^+$ 328/330 | purified by FCC (silica, heptane then ethyl acetate) and preparative HPLC (acetonitrile-water-0.1% formic acid) to give the title compound 1.7 mg (3% yield) as a yellow powder.

Step 1, Method 36: 4-Iodo-6-(5-methoxy-1-benzofuran-2-yl)pyrimidine-5-carbonitrile $\delta_H$ NMR (500 MHz, chloroform) 8.90 (s, 1H), 8.07 (d, J=0.9 Hz, 1H), 7.57 (m, 1H), 7.16-7.10 (m, 2H), 3.88 (s, 3H). Tr(MET-uHPLC-AB-101)=3.65 min, (ES$^+$) (M+H)$^+$ 378.

The following example was prepared using Method 36 described above:

TABLE 37

| Example | Structure | Mol. Weight | IUPAC Name | LCMS data |
|---|---|---|---|---|
| 1 | 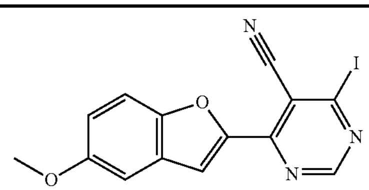 | 377.14 | 4-Iodo-6-(5-methoxy-1-benzofuran-2-yl)pyrimidine-5-carbonitrile | Tr(MET-uHPLC-AB-101) = 3.65 min, (ES$^+$) (M + H)$^+$ 378 |

Method 37

Scheme for Method 37

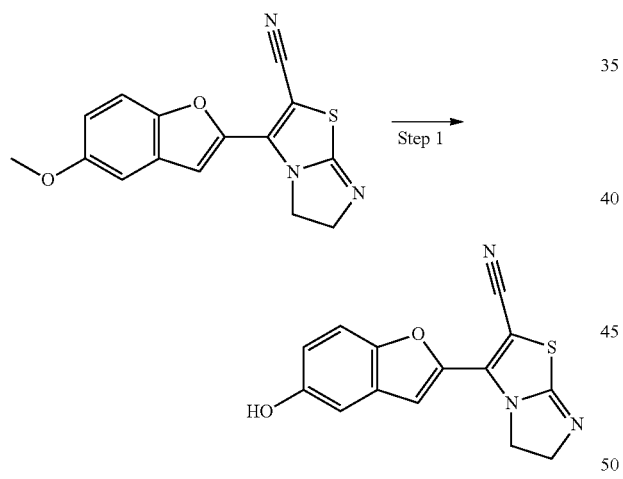

Step 1, Method 37: 3-(5-Hydroxy-1-benzofuran-2-yl)-5H,6H-imidazo[2,1-b][1,3]thiazole-2-carbonitrile To a solution of 3-(5-methoxy-1-benzofuran-2-yl)-5H,6H-imidazo[2,1-b][1,3]thiazole-2-carbonitrile (100 mg, 0.34 mmol, prepared by Method 30) in dry dichloromethane (15 mL) at 0° C. was added 1 M boron tribromide in dichloromethane (1.4 mL, 1.4 mmol). The cooling bath was removed and the mixture stirred at room temperature for 2 days before being added to saturated aqueous sodium bicarbonate (200 mL). The mixture was extracted with ethyl acetate (3×100 mL) and the combined extracts washed with brine (50 mL), dried over magnesium sulphate, filtered and concentrated. Purification by FCC (silica, 0-10% methanol in dichloromethane) and trituration with methanol (3 mL) gave the title compound 56 mg (57% yield) as a yellow solid.

Example 1, Method 37: 3-(5-Hydroxy-1-benzofuran-2-yl)-5H,6H-imidazo[2,1-b][1,3]thiazole-2-carbonitrile $\delta_H$ NMR (500 MHz, DMSO) 9.53 (s, 1H), 7.57 (s, 1H), 7.48 (d, J=8.9 Hz, 1H), 7.08 (s, 1H), 6.94 (d, J=8.6 Hz, 1H), 4.40-4.11 (m, 4H). Tr(MET-uHPLC-AB-101)=1.16 min, (ES$^+$) (M+H)$^+$ 284.

The following example was prepared using Method 37 described above:

TABLE 38

| Example | Structure | Mol. Weight | IUPAC Name | LCMS data |
|---|---|---|---|---|
| 1 | 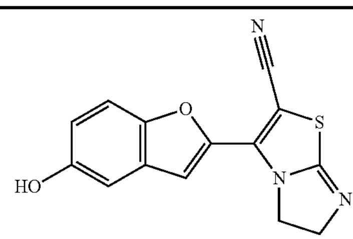 | 283.31 | 3-(5-Hydroxy-1-benzofuran-2-yl)-5H,6H-imidazo[2,1-b][1,3]thiazole-2-carbonitrile | Tr(MET-uHPLC-AB-101) = 1.16 min, (ES$^+$) (M + H)$^+$ 284 |

Biology Examples

Q46 Radioligand Binding Assay

For radioligand binding assays (RBA) GST-Q46 protein was generated based on a previous publication (Scherzinger et al. Cell, Vol. 90, 549-558, Aug. 8, 1997). For experiments 33 μM GST-Q46 was incubated with 150 μg/mL thrombin in assay buffer (150 mM NaCl, 50 mM Tris pH 8.0) and 2 mM $CaCl_2$ for 16 hr at 37° C. Aggregated Q46 was pelleted by centrifugation for 5 min at 13,000 rpm in a bench top centrifuge and re-dissolved in the same volume of assay buffer. Test compounds were prepared by titration in DMSO at 11 concentrations from 33 μM to 1 nM. For the RBA, Q46 protein aggregates and test compounds were pre-incubated in assay buffer for 20 min at room temperature, in 140 μL/well in a 96-well plate (pp, round bottom). Then, ligand was added in 10 μL/well and incubated for 60 min at 37° C. Final assay concentrations were 1 μM to 30 pM test compound, 5 μM Q46 protein (equivalent monomer concentration) and 10 nM ligand [$^3H_3$]MK-3328 (Harrision et al., *ACS Med. Chem. Lett.*, 2 (2011), pp 498-502). Samples were transferred onto GF/B filter plates and washed 2× with 200 μL PBS using a Filtermate Harvester. After drying filter plates for 1 hr at 37° C., the back of the plates was sealed with foil and 30 μL/well scintillation fluid (Packard MicroScint 40) was added, incubated for incubated for 15 min in the dark and counted in a TopCount reader. For analysis, replicate data from independent assay plates were normalized towards 0% and 100% inhibition using control wells of vehicle (0% inhibition) and 3 μM unlabelled MK-3328 (100% inhibition). $IC_{50}$ values were determined with a sigmoidal inhibition model with four variables (top, bottom, slope, $IC_{50}$) in a global fit using the normalized replicate data.

| Structure | IUPAC Name | Activity |
|---|---|---|
| RBA $IC_{50}$ activity summary: <100 nM +++, 100-500 nM ++, >500 nM + | | |
| 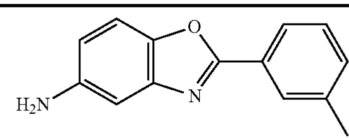 | 2-(3-methylphenyl)-1,3-benzoxazol-5-amine | ++ |
| 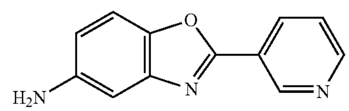 | 2-(pyridin-3-yl)-1,3-benzoxazol-5-amine | + |
| 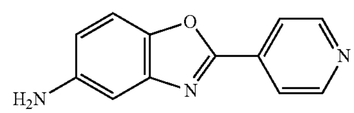 [SMILES: Nc1ccc2oc(-c3ccncc3)nc2c1] | 2-(pyridin-4-yl)-1,3-benzoxazol-5-amine | + |
| 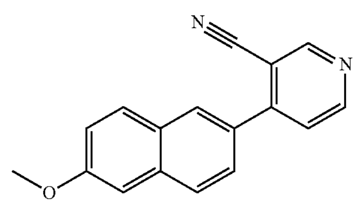 [SMILES: COc1ccc2cc(-c3ccncc3C#N)ccc2c1] | 4-(6-methoxynaphthalen-2-yl)pyridine-3-carbonitrile | ++ |
| 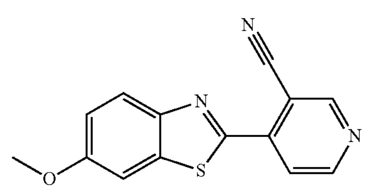 [SMILES: COc1ccc2nc(-c3ccncc3C#N)sc2c1] | 4-(6-methoxy-1,3-benzothiazol-2-yl)pyridine-3-carbonitrile | ++ |
| 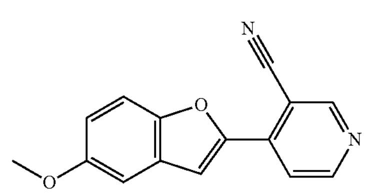 [SMILES: COc1ccc2oc(-c3ccncc3C#N)cc2c1] | 4-(5-methoxy-1-benzofuran-2-yl)pyridine-3-carbonitrile | +++ |
| 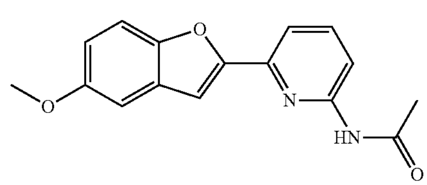 [SMILES: COc1ccc2oc(-c3cccc(NC(C)=O)n3)cc2c1] | N-[6-(5-methoxy-1-benzofuran-2-yl)pyridin-2-yl]acetamide | +++ |

-continued

| RBA IC$_{50}$ activity summary: <100 nM +++, 100-500 nM ++, >500 nM + | | |
|---|---|---|
| Structure | IUPAC Name | Activity |
| | 6-(5-methoxy-1-benzofuran-2-yl)pyridine-3-carbonitrile | +++ |
| | 4-(1,3-benzothiazol-2-yl)pyridine-3-carbonitrile | + |
| | 2-(6-methoxy-1,3-benzothiazol-2-yl)benzonitrile | +++ |
| | 2-(3-bromopyridin-4-yl)-6-methoxy-1,3-benzothiazole | +++ |
| | 2-(3-bromopyridin-4-yl)-1,3-benzothiazol-6-ol | ++ |
| | 2-(3-bromopyridin-2-yl)-6-methoxy-1,3-benzothiazole | +++ |
| | 2-(6-methoxy-1,3-benzothiazol-2-yl)pyridine-3-carbonitrile | +++ |
| | 2-(3-fluoropyridin-4-yl)-6-methoxy-1,3-benzothiazole | +++ |
| | 6-methoxy-2-(2-methoxyphenyl)-1,3-benzothiazole | ++ |

-continued

| Structure | IUPAC Name | Activity |
|---|---|---|
| 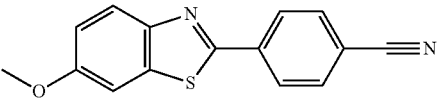 [SMILES: COc1ccc2nc(-c3ccc(C#N)cc3)sc2c1] | 4-(6-methoxy-1,3-benzothiazol-2-yl)benzonitrile | +++ |
| 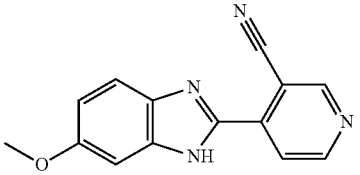 [SMILES: COc1ccc2nc(-c3ccncc3C#N)[nH]c2c1] | 4-(6-methoxy-1H-1,3-benzodiazol-2-yl)pyridine-3-carbonitrile | + |
| 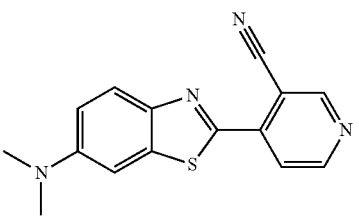 [SMILES: CN(C)c1ccc2nc(-c3ccncc3C#N)sc2c1] | 4-[6-(dimethylamino)-1,3-benzothiazol-2-yl]pyridine-3-carbonitrile | +++ |
| 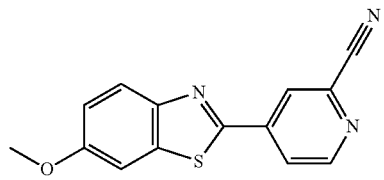 [SMILES: COc1ccc2nc(-c3ccnc(C#N)c3)sc2c1] | 4-(6-methoxy-1,3-benzothiazol-2-yl)pyridine-2-carbonitrile | +++ |
| 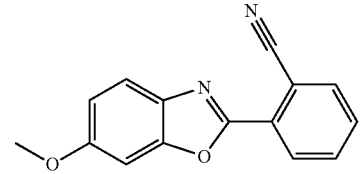 [SMILES: COc1ccc2nc(-c3ccccc3C#N)oc2c1] | 2-(6-methoxy-1,3-benzoxazol-2-yl)benzonitrile | +++ |
| 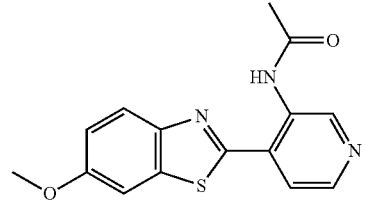 [SMILES: COc1ccc2nc(-c3ccncc3NC(C)=O)sc2c1] | N-[4-(6-methoxy-1,3-benzothiazol-2-yl)pyridin-3-yl]acetamide | +++ |
| 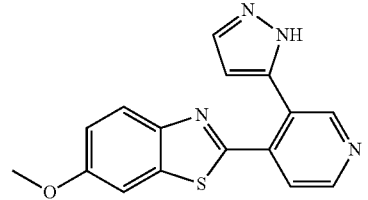 [SMILES: COc1ccc2nc(-c3ccncc3-c3ccn[nH]3)sc2c1] | 6-methoxy-2-[3-(1H-pyrazol-5-yl)pyridin-4-yl]-1,3-benzothiazole | ++ |
| 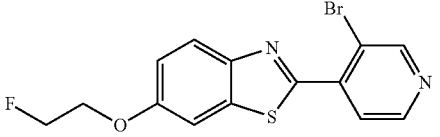 | 2-(3-bromopyridin-4-yl)-6-(2-fluoroethoxy)-1,3-benzothiazole | +++ |

RBA IC$_{50}$ activity summary: <100 nM +++, 100-500 nM ++, >500 nM +

-continued

RBA IC$_{50}$ activity summary: <100 nM +++, 100-500 nM ++, >500 nM +

| Structure | IUPAC Name | Activity |
|---|---|---|
| 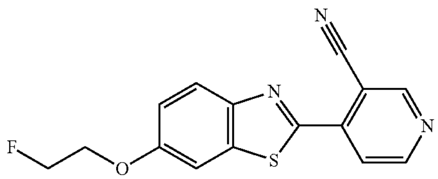 [SMILES: N#Cc1cnccc1-c1nc2ccc(OCCF)cc2s1] | 4-[6-(2-fluoroethoxy)-1,3-benzothiazol-2-yl]pyridine-3-carbonitrile | +++ |
| 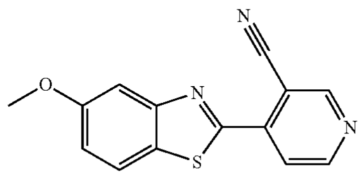 [SMILES: COc1ccc2sc(-c3ccncc3C#N)nc2c1] | 4-(5-methoxy-1,3-benzothiazol-2-yl)pyridine-3-carbonitrile | ++ |
| 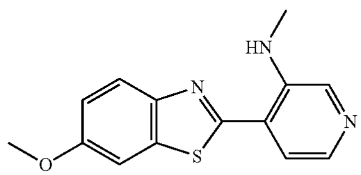 [SMILES: CNc1cnccc1-c1nc2ccc(OC)cc2s1] | 4-(6-methoxy-1,3-benzothiazol-2-yl)-N-methylpyridin-3-amine | ++ |
| 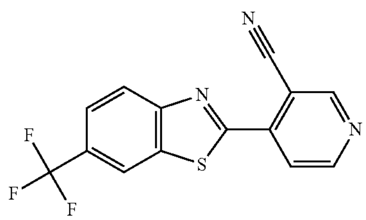 [SMILES: N#Cc1cnccc1-c1nc2ccc(C(F)(F)F)cc2s1] | 4-[6-(trifluoromethyl)-1,3-benzothiazol-2-yl]pyridine-3-carbonitrile | +++ |
| 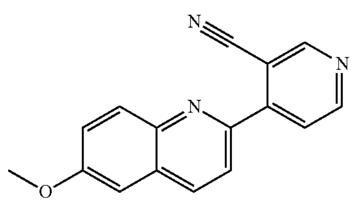 [SMILES: COc1ccc2nc(-c3ccncc3C#N)ccc2c1] | 4-(6-methoxyquinolin-2-yl)pyridine-3-carbonitrile | ++ |
| 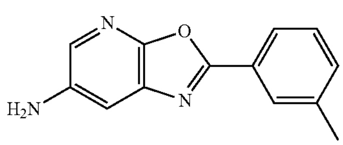 [SMILES: Cc1cccc(-c2nc3cc(N)cnc3o2)c1] | 2-(3-methylphenyl)-[1,3]oxazolo[5,4-b]pyridin-6-amine | + |
| 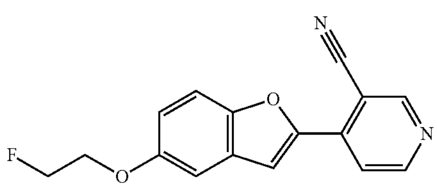 [SMILES: N#Cc1cnccc1-c1cc2cc(OCCF)ccc2o1] | 4-[5-(2-fluoroethoxy)-1-benzofuran-2-yl]pyridine-3-carbonitrile | +++ |
| 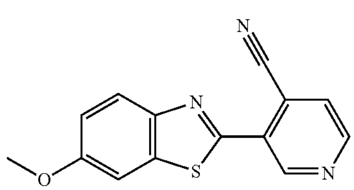 | 3-(6-methoxy-1,3-benzothiazol-2-yl)pyridine-4-carbonitrile | +++ |

-continued

| Structure | IUPAC Name | Activity |
|---|---|---|
| 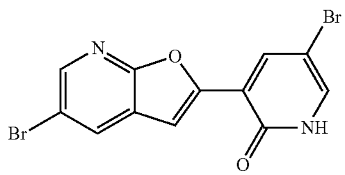 [SMILES: O=c1[nH]cc(Br)cc1-c1cc2cc(Br)cnc2o1] | 5-bromo-3-{5-bromofuro[2,3-b]pyridin-2-yl}-1,2-dihydropyridin-2-one | +++ |
| 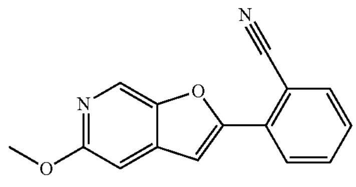 [SMILES: COc1cc2cc(-c3ccccc3C#N)oc2cn1] | 2-{5-methoxyfuro[2,3-c]pyridin-2-yl}benzonitrile | +++ |
| 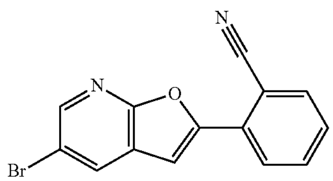 [SMILES: N#Cc1ccccc1-c1cc2cc(Br)cnc2o1] | 2-{5-bromofuro[2,3-b]pyridin-2-yl}benzonitrile | +++ |
| 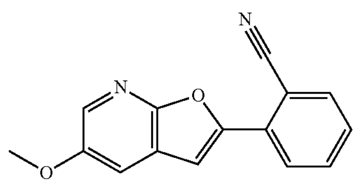 [SMILES: COc1cnc2oc(-c3ccccc3C#N)cc2c1] | 2-{5-methoxyfuro[2,3-b]pyridin-2-yl}benzonitrile | +++ |
| 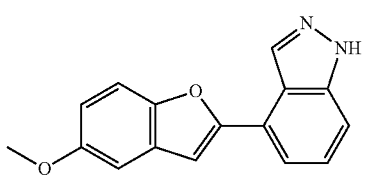 [SMILES: COc1ccc2oc(-c3cccc4[nH]ncc34)cc2c1] | 4-(5-methoxy-1-benzofuran-2-yl)-1H-indazole | +++ |
| 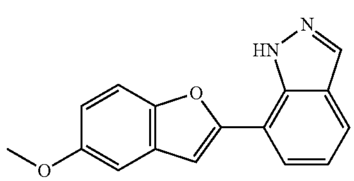 [SMILES: COc1ccc2oc(-c3cccc4cn[nH]c34)cc2c1] | 7-(5-methoxy-1-benzofuran-2-yl)-1H-indazole | +++ |
| 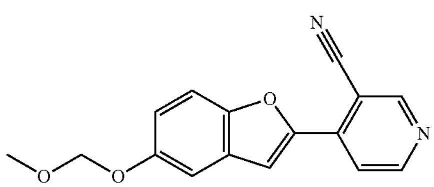 | 4-[5-(methoxymethoxy)-1-benzofuran-2-yl]pyridine-3-carbonitrile | +++ |
| 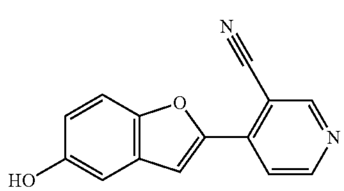 | 4-(5-hydroxy-1-benzofuran-2-yl)pyridine-3-carbonitrile | +++ |

RBA IC$_{50}$ activity summary: <100 nM +++, 100-500 nM ++, >500 nM +

-continued

RBA IC$_{50}$ activity summary: <100 nM +++, 100-500 nM ++, >500 nM +

| Structure | IUPAC Name | Activity |
|---|---|---|
| 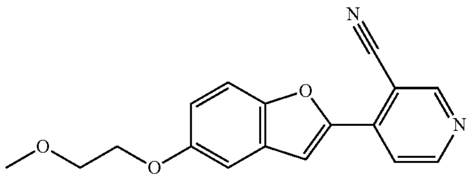 [SMILES: COCCOc1ccc2oc(-c3ccncc3C#N)cc2c1] | 4-[5-(2-methoxyethoxy)-1-benzofuran-2-yl]pyridine-3-carbonitrile | +++ |
| 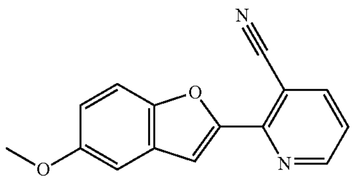 [SMILES: COc1ccc2oc(-c3ncccc3C#N)cc2c1] | 2-(5-methoxy-1-benzofuran-2-yl)pyridine-3-carbonitrile | +++ |
| 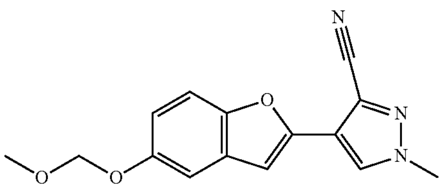 | 4-[5-(methoxymethoxy)-1-benzofuran-2-yl]-1-methyl-1H-pyrazole-3-carbonitrile | +++ |
| 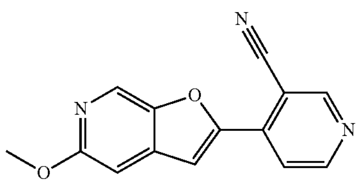 [SMILES: COc1cc2cc(-c3ccncc3C#N)oc2cn1] | 4-{5-methoxyfuro[2,3-c]pyridin-2-yl}pyridine-3-carbonitrile | +++ |
| 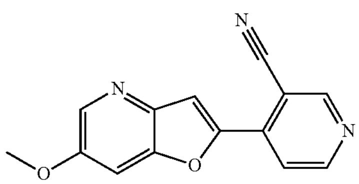 [SMILES: COc1cnc2cc(-c3ccncc3C#N)oc2c1] | 4-{6-methoxyfuro[3,2-b]pyridin-2-yl}pyridine-3-carbonitrile | +++ |
| 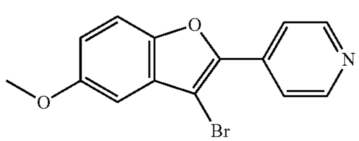 | 4-(3-bromo-5-methoxy-1-benzofuran-2-yl)pyridine | +++ |
| 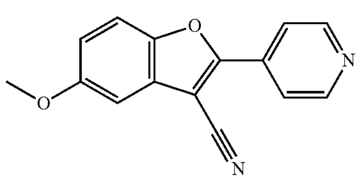 [SMILES: COc1ccc2oc(-c3ccncc3)c(C#N)c2c1] | 5-methoxy-2-(pyridin-4-yl)-1-benzofuran-3-carbonitrile | +++ |
| 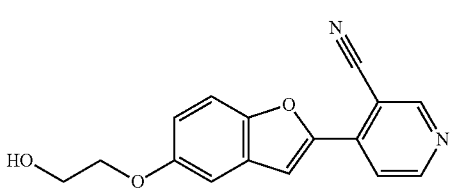 [SMILES: N#Cc1cnccc1-c1cc2cc(OCCO)ccc2o1] | 4-[5-(2-hydroxyethoxy)-1-benzofuran-2-yl]pyridine-3-carbonitrile | ++ |

-continued

RBA IC$_{50}$ activity summary: <100 nM +++, 100-500 nM ++, >500 nM +

| Structure | IUPAC Name | Activity |
|---|---|---|
| 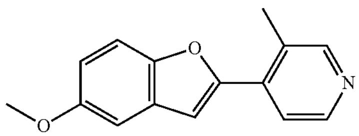 [SMILES: COc1ccc2oc(-c3ccncc3C)cc2c1] | 4-(5-methoxy-1-benzofuran-2-yl)-3-methylpyridine | ++ |
| 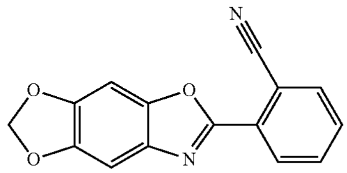 [SMILES: N#Cc1ccccc1-c1nc2cc3c(cc2o1)OCO3] | 2-{4,6,10-trioxa-12-azatricyclo[7.3.0.0$^{3,7}$]dodeca-1(9),2,7,11-tetraen-11-yl}benzonitrile | +++ |
| 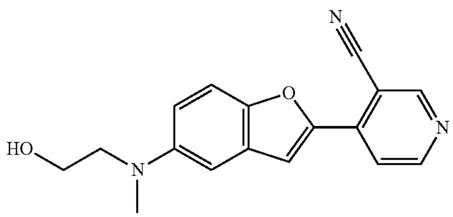 [SMILES: CN(CCO)c1ccc2oc(-c3ccncc3C#N)cc2c1] | 4-{5-[(2-hydroxyethyl)(methyl)amino]-1-benzofuran-2-yl}pyridine-3-carbonitrile | +++ |
| 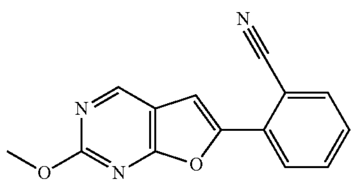 [SMILES: COc1ncc2cc(-c3ccccc3C#N)oc2n1] | 2-{2-methoxyfuro[2,3-d]pyrimidin-6-yl}benzonitrile | +++ |
| 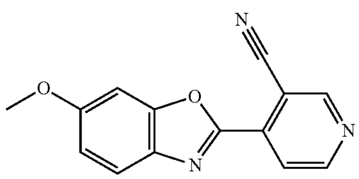 [SMILES: COc1ccc2nc(-c3ccncc3C#N)oc2c1] | 4-(6-methoxy-1,3-benzoxazol-2-yl)pyridine-3-carbonitrile | +++ |
| 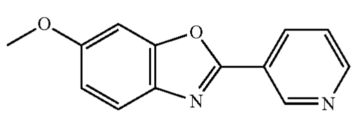 | 6-methoxy-2-(pyridin-3-yl)-1,3-benzoxazole | ++ |
| 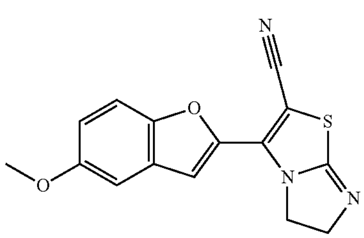 [SMILES: COc1ccc2oc(C3=C(C#N)SC4=NCCN43)cc2c1] | 3-(5-methoxy-1-benzofuran-2-yl)-5H,6H-imidazo[2,1-b][1,3]thiazole-2-carbonitrile | +++ |
| 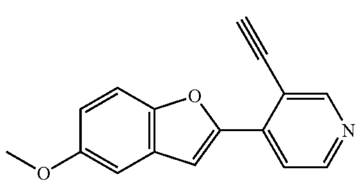 | 3-ethynyl-4-(5-methoxy-1-benzofuran-2-yl)pyridine | +++ |

-continued

| Structure | IUPAC Name | Activity |
|---|---|---|
| 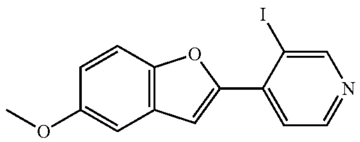 | 3-iodo-4-(5-methoxy-1-benzofuran-2-yl)pyridine | ++ |
| 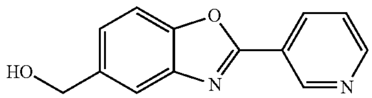 [SMILES: OCc1ccc2oc(-c3cccnc3)nc2c1] | [2-(pyridin-3-yl)-1,3-benzoxazol-5-yl]methanol | + |
| 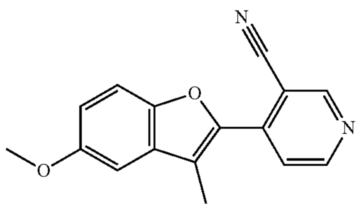 [SMILES: COc1ccc2oc(-c3ccncc3C#N)c(C)c2c1] | 4-(5-methoxy-3-methyl-1-benzofuran-2-yl)pyridine-3-carbonitrile | +++ |
| 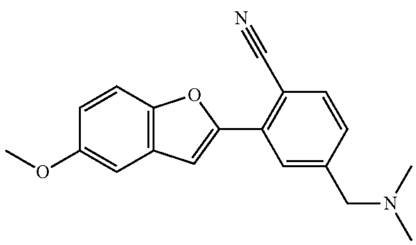 | 4-[(dimethylamino)methyl]-2-(5-methoxy-1-benzofuran-2-yl)benzonitrile | +++ |
| 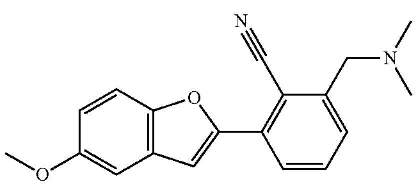 | 2-[(dimethylamino)methyl]-6-(5-methoxy-1-benzofuran-2-yl)benzonitrile | ++ |
| 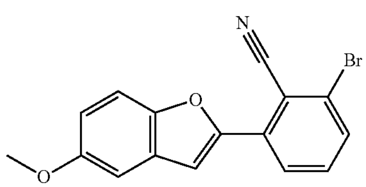 [SMILES: COc1ccc2oc(-c3cccc(Br)c3C#N)cc2c1] | 2-bromo-6-(5-methoxy-1-benzofuran-2-yl)benzonitrile | +++ |
| 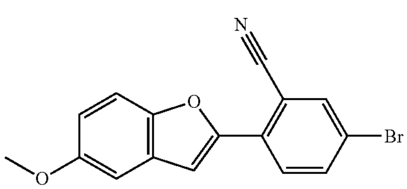 [SMILES: COc1ccc2oc(-c3ccc(Br)cc3C#N)cc2c1] | 5-bromo-2-(5-methoxy-1-benzofuran-2-yl)benzonitrile | +++ |
| 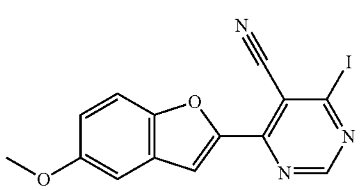 | 4-iodo-6-(5-methoxy-1-benzofuran-2-yl)pyrimidine-5-carbonitrile | + |

RBA IC$_{50}$ activity summary: <100 nM +++, 100-500 nM ++, >500 nM +

| RBA IC$_{50}$ activity summary: <100 nM +++, 100-500 nM ++, >500 nM + | | |
|---|---|---|
| Structure | IUPAC Name | Activity |
| | 3-(5-hydroxy-1-benzofuran-2-yl)-5H,6H-imidazo[2,1-b][1,3]thiazole-2-carbonitrile | +++ |
| | 3-(5-Hydroxy-1-benzofuran-2-yl)-5H,6H-imidazo[2,1-b][1,3]thiazole-2-carbonitrile | +++ |

Various modifications, additions, substitutions, and variations to the illustrative examples set forth herein will be apparent to those skilled in the art from the foregoing description. Such modifications are also intended to fall within the scope of the appended claims.

What is claimed is:

1. An imaging agent comprising a compound:
4-[5-(methoxymethoxy)-1-benzofuran-2-yl]-1-methyl-1H-pyrazole-3-carbonitrile;
2-[(dimethylamino)methyl]-6-(5-methoxy-1-benzofuran-2-yl)benzonitrile;
2-bromo-6-(5-methoxy-1-benzofuran-2-yl)benzonitrile;
5-bromo-2-(5-methoxy-1-benzofuran-2-yl)benzonitrile;
4-iodo-6-(5-methoxy- 1-benzofuran-2-yl)pyrimidine-5-carbonitrile;
3-(5-hydroxy-1-benzofuran-2-yl)-5H,6H-imidazo[2,1-b][1,3]thiazole-2-carbonitrile;
4-(6-methoxynaphthalen-2-yl)pyridine-3-carbonitrile;
4-(6-methoxy-1H-1,3-benzodiazol-2-yl)pyridine-3-carbonitrile;
6-methoxy-2-[3-(1H-pyrazol-5-yl)pyridin-4-yl]-1,3-benzothiazole;
4-(6-methoxyquinolin-2-yl)pyridine-3-carbonitrile;
4-(6-methoxy-1,3-benzothiazol-2-yl)pyridine-3-carbonitrile;
4-(5-methoxy-1-benzofuran-2-yl)pyridine-3-carbonitrile;
6-(5-methoxy-1-benzofuran-2-yl)pyridine-3-carbonitrile;
4-(1,3-benzothiazol-2-yl)pyridine-3-carbonitrile;
2-(6-methoxy-1,3-benzothiazol-2-yl)benzonitrile;
2-(6-methoxy-1,3-benzothiazol-2-yl)pyridine-3-carbonitrile;
4-[6-(dimethylamino)-1,3-benzothiazol-2-yl]pyridine-3-carbonitrile;
4-(6-methoxy-1,3-benzothiazol-2-yl)pyridine-2-carbonitrile;
2-(6-methoxy-1,3-benzoxazol-2-yl)benzonitrile;
4-[6-(2-fluoroethoxy)-1,3-benzothiazol-2-yl]pyridine-3-carbonitrile;
4-(5-methoxy-1,3-benzothiazol-2-yl)pyridine-3-carbonitrile;
4-[6-(trifluoromethyl)-1,3-benzothiazol-2-yl]pyridine-3-carbonitrile;
4-[5-(2-fluoroethoxy)-1-benzofuran-2-yl]pyridine-3-carbonitrile;
3-(6-methoxy-1,3-benzothiazol-2-yl)pyridine-4-carbonitrile;
5-bromo-3 -{5-bromofuro[2,3-b]pyridin-2-yl}-1,2-dihydropyridin-2-one;
2-{5-methoxyfuro[2,3-c]pyridin-2-yl}benzonitrile;
2-{5-bromofuro[2,3-b]pyridin-2-yl}benzonitrile;
2-{5-methoxyfuro[2,3-b]pyridin-2-yl}benzonitrile;
4-[5-(methoxymethoxy)-1-benzofuran-2-yl]pyridine-3-carbonitrile;
4-(5-hydroxy-1-benzofuran-2-yl)pyridine-3-carbonitrile;
4-[5-(2-methoxyethoxy)-1-benzofuran-2-yl]pyridine-3-carbonitrile;
2-(5-methoxy-1-benzofuran-2-yl)pyridine-3-carbonitrile;
4-{ 5-methoxyfuro [2,3-]pyridin-2-yl}pyridine-3-carbonitrile;
4-{6-methoxyfuro[3,2-b]pyridin-2-yl}pyridine-3-carbonitrile;
5-methoxy-2-(pyridin-4-yl)-1-benzofuran-3-carbonitrile;
4-[5-(2-hydroxyethoxy)-1-benzofuran-2-yl]pyridine-3-carbonitrile;
2-{4,6,10-trioxa-12-azatricyclo[7.3.0.0$^{3,7}$]dodeca-1(9),2,7,11-tetraen-11-yl }benzonitrile;
4-{5-[(2-hydroxyethyl)(methyl)amino]-1-benzofuran-2-yl}pyridine-3-carbonitrile;
2-{2-methoxyfuro[2,3-d]pyrimidin-6-yl}benzonitrile;
4-(6-methoxy-1,3-benzoxazol-2-yl)pyridine-3-carbonitrile;
3-(5-methoxy-1-benzofuran-2-yl)-5H,6H-imidazo[2,1-b][1,3]thiazole-2-carbonitrile;
3-ethynyl-4-(5-methoxy-1-benzofuran-2-yl)pyridine;
4-(5-methoxy-3-methyl-1-benzofuran-2-yl)pyridine-3-carbonitrile; or
4-[(dimethylamino)methyl]-2-(5-methoxy-1-benzofuran-2-yl)benzonitrile;
or a pharmaceutically acceptable salt thereof, wherein the compound is labeled with one or more positron-emitting radionuclides.

2. The imaging agent of claim 1, wherein said one or more positron-emitting radionuclides are selected from: $^{11}$C, $^{13}$N, $^{15}$O, $^{18}$F, $^{76}$Br, and $^{124}$I.

3. A method of generating diagnostic images in an individual comprising administering an effective amount of an imaging agent of claim 1 to an individual, and generating an image of at least a part of said individual.

4. The method of claim 3, wherein generating an image of at least a part of said individual comprises generating an image to detect the presence or absence of huntingtin protein (HTT protein) aggregates in the brain of said individual; and detecting the presence or absence of a pathologic process.

5. The method of claim 4, wherein said HTT protein aggregates are present in the basal ganglia of said brain of said individual.

6. The method of claim 4, wherein the pathologic process is a neurodegenerative disease.

7. The method of claim 6, wherein the neurodegenerative disease is chosen from Alzheimer's disease, amyotrophic lateral sclerosis, Huntington's disease, Parkinson's disease, Prion disease and spinocerebellar ataxias.

8. The method of claim 7, wherein the neurodegenerative disease is Huntington's disease (HD).

9. The method of claim 3, wherein said effective amount of said imaging agent comprises from about 0.1 to about 20 mCi.

10. The method of claim 3, wherein said generating an image comprises positron emission tomography (PET) imaging, PET with concurrent computed tomography imaging (PET/CT), PET with concurrent magnetic resonance imaging (PET/MRI), or a combination thereof.

11. The method of claim 10, wherein said generating an image comprises PET imaging.

12. A compound, or a pharmaceutically acceptable salt thereof, wherein the compound is selected from:
- 4-[5-(methoxymethoxy)-1-benzofuran-2-yl]-1-methyl-1H-pyrazole-3-carbonitrile;
- 2-[(dimethylamino)methyl]-6-(5-methoxy-1-benzofuran-2-yl)benzonitrile;
- 2-bromo-6-(5-methoxy-1-benzofuran-2-yl)benzonitrile;
- 5-bromo-2-(5-methoxy-1-benzofuran-2-yl)benzonitrile;
- 4-iodo-6-(5-methoxy-1-benzofuran-2-yl)pyrimidine-5-carbonitrile;
- 3-(5-hydroxy-1-benzofuran-2-yl)-5H,6H-imidazo[2,1-b][1,3]thiazole-2-carbonitrile;
- 4-(6-methoxynaphthalen-2-yl)pyridine-3-carbonitrile;
- 4-(6-methoxy-1H-1,3-benzodiazol-2-yl)pyridine-3-carbonitrile;
- 6-methoxy-2-[3-(1H-pyrazol-5-yl)pyridin-4-yl]-1,3-benzothiazole;
- 4-(6-methoxyquinolin-2-yl)pyridine-3-carbonitrile;
- 4-(6-methoxy-1,3-benzothiazol-2-yl)pyridine-3-carbonitrile;
- 4-(5-methoxy-1-benzofuran-2-yl)pyridine-3-carbonitrile;
- 6-(5-methoxy-1-benzofuran-2-yl)pyridine-3-carbonitrile;
- 4-(1,3-benzothiazol-2-yl)pyridine-3-carbonitrile;
- 2-(6-methoxy-1,3-benzothiazol-2-yl)benzonitrile;
- 2-(6-methoxy-1,3-benzothiazol-2-yl)pyridine-3-carbonitrile;
- 4-[6-(dimethylamino)-1,3-benzothiazol-2-yl]pyridine-3-carbonitrile;
- 4-(6-methoxy-1,3-benzothiazol-2-yl)pyridine-2-carbonitrile;
- 2-(6-methoxy-1,3-benzoxazol-2-yl)benzonitrile;
- 4-[6-(2-fluoroethoxy)-1,3-benzothiazol-2-yl]pyridine-3-carbonitrile;
- 4-(5-methoxy-1,3-benzothiazol-2-yl)pyridine-3-carbonitrile;
- 4-[6-(trifluoromethyl)-1,3-benzothiazol-2-yl]pyridine-3-carbonitrile;
- 4-[5-(2-fluoroethoxy)-1-benzofuran-2-yl]pyridine-3-carbonitrile;
- 3-(6-methoxy-1,3-benzothiazol-2-yl)pyridine-4-carbonitrile;
- 5-bromo-3-{5-bromofuro[2,3-b]pyridin-2-yl}-1,2-dihydropyridin-2-one;
- 2-{5-methoxyfuro[2,3-c]pyridin-2-yl}benzonitrile;
- 2-{5-bromofuro[2,3-b]pyridin-2-yl}benzonitrile;
- 2-{5-methoxyfuro[2,3-b]pyridin-2-yl}benzonitrile;
- 4-[5-(methoxymethoxy)-1-benzofuran-2-yl]pyridine-3-carbonitrile;
- 4-(5-hydroxy-1-benzofuran-2-yl)pyridine-3-carbonitrile;
- 4-[5-(2-methoxyethoxy)-1-benzofuran-2-yl]pyridine-3-carbonitrile;
- 2-(5-methoxy-1-benzofuran-2-yl)pyridine-3-carbonitrile;
- 4-{5-methoxyfuro[2,3-c]pyridin-2-yl}pyridine-3-carbonitrile;
- 4-{6-methoxyfuro[3,2-b]pyridin-2-yl}pyridine-3-carbonitrile;
- 5-methoxy-2-(pyridin-4-yl)-1-benzofuran-3-carbonitrile;
- 4-[5-(2-hydroxyethoxy)-1-benzofuran-2-yl]pyridine-3-carbonitrile;
- 2-{4,6,10-trioxa-12-azatricyclo[7.3.0.0$^{3,7}$]dodeca-1(9),2,7,11-tetraen-11-yl}benzonitrile;
- 4-{5-[(2-hydroxyethyl)(methyl)amino]-1-benzofuran-2-yl}pyridine-3-carbonitrile;
- 2-{2-methoxyfuro[2,3-d]pyrimidin-6-yl}benzonitrile;
- 4-(6-methoxy-1,3-benzoxazol-2-yl)pyridine-3-carbonitrile;
- 3-(5-methoxy-1-benzofuran-2-yl)-5H,6H-imidazo[2,1-b][1,3]thiazole-2-carbonitrile;
- 3-ethynyl-4-(5-methoxy-1-benzofuran-2-yl)pyridine;
- 4-(5-methoxy-3-methyl-1-benzofuran-2-yl)pyridine-3-carbonitrile; or
- 4-[(dimethylamino)methyl]-2-(5-methoxy-1-benzofuran-2-yl)benzonitrile.

* * * * *

UNITED STATES PATENT AND TRADEMARK OFFICE
CERTIFICATE OF CORRECTION

| | |
|---|---|
| PATENT NO. | : 10,907,197 B2 |
| APPLICATION NO. | : 15/507217 |
| DATED | : February 2, 2021 |
| INVENTOR(S) | : Celia Dominguez et al. |

It is certified that error appears in the above-identified patent and that said Letters Patent is hereby corrected as shown below:

In the Claims

In Claim 1, Column 111, Lines 39-40, please replace "4-iodo-6-(5-methoxy- 1-benzofuran-2-yl)pyrimidine-5-carbonitrile" with --4-iodo-6-(5-methoxy-1-benzofuran-2-yl)pyrimidine-5-carbonitrile--.

In Claim 1, Column 112, Lines 30-31, please replace "5-bromo-3 -{5-bromofuro[2,3-b]pyridin-2-yl}-1,2-dihydropyridin-2-one" with --5-bromo-3-{5-bromofuro[2,3-b]pyridin-2-yl}-1,2-dihydropyridin-2-one--.

In Claim 1, Column 112, Lines 41-42, please replace "4-{ 5-methoxyfuro [2,3-]pyridin-2-yl}pyridine-3-carbonitrile" with --4-{5-methoxyfuro[2,3-c]pyridin-2-yl}pyridine-3-carbonitrile--.

In Claim 1, Column 112, Lines 48-49, please replace "2-{4,6,10-trioxa-12-azatricyclo[7.3.0.0$^{3,7}$]dodeca-1(9),2,7,11-tetraen-11-yl }benzonitrile" with --2-{4,6,10-trioxa-12-azatricyclo[7.3.0.0$^{3,7}$]dodeca-1(9),2,7,11-tetraen-11-yl}benzonitrile--.

Signed and Sealed this
Twenty-first Day of March, 2023

Katherine Kelly Vidal
*Director of the United States Patent and Trademark Office*